United States Patent
Demoulin et al.

(10) Patent No.: US 11,897,924 B2
(45) Date of Patent: Feb. 13, 2024

(54) ANTICOAGULANT FUSION PROTEINS AND USES THEREOF

(71) Applicant: BIOXODES, Marche-en-Famenne (BE)

(72) Inventors: Stéphanie Demoulin, Antheit (BE); Edmond Godfroid, Brussels (BE); Michel Guyaux, Woluwe-Saint-Pierre (BE); Joël Tassignon, Roux (BE)

(73) Assignee: BIOXODES, Marche-en-Famenne (BE)

( * ) Notice: Subject to any disclaimer, the term of this patent is extended or adjusted under 35 U.S.C. 154(b) by 0 days.

(21) Appl. No.: 16/982,966

(22) PCT Filed: Mar. 28, 2019

(86) PCT No.: PCT/EP2019/057914
§ 371 (c)(1),
(2) Date: Sep. 21, 2020

(87) PCT Pub. No.: WO2019/185828
PCT Pub. Date: Oct. 3, 2019

(65) Prior Publication Data
US 2021/0070817 A1    Mar. 11, 2021

(30) Foreign Application Priority Data

Mar. 28, 2018 (EP) ..................... 18164570

(51) Int. Cl.
| | | |
|---|---|---|
| *C07K 14/435* | (2006.01) | |
| *A61P 7/04* | (2006.01) | |
| *C07K 14/765* | (2006.01) | |
| *A61K 38/00* | (2006.01) | |

(52) U.S. Cl.
CPC .......... *C07K 14/43527* (2013.01); *A61P 7/04* (2018.01); *C07K 14/765* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,876,969 A | * | 3/1999 | Fleer ............... | A61K 38/21 514/14.2 |
| 8,277,818 B2 | * | 10/2012 | Coffin ............... | A61P 35/00 424/199.1 |
| 10,301,629 B2 | * | 5/2019 | Littman ............ | A61K 47/645 |
| 2013/0129741 A1 | | 5/2013 | Godfroid et al. | |
| 2016/0046728 A1 | | 2/2016 | Godfroid et al. | |
| 2021/0070817 A1 | * | 3/2021 | Demoulin ......... | C07K 14/8114 |

FOREIGN PATENT DOCUMENTS

| | | |
|---|---|---|
| WO | 00/77198 | 12/2000 |
| WO | 2009/141382 | 11/2009 |
| WO | 2019/149906 | 8/2019 |

OTHER PUBLICATIONS

Darbousset et al. "Tissue factor-positive neutrophils bind to injured endothelial wall and initiate thrombus formation" Blood. 2012; 120(10):2133-2143.
Decrem et al. "Ir-CPI, a coagulation contact phase inhibitor from the tick *Ixodes ricinus*, inhibits thrombus formation without impairing hemostasis", J. Exp. Med. vol. 206 No. 11, 2009, pp. 2381-2395.
Kontos et al. "Improving protein pharmacokinetics by engineering erythrocyte affinity", Molecul. Pharm. vol. 7 No. 6, 2010, pp. 2141-2147.
Leboulle et al. "Isolation of Ixodes ricinus salivary gland mRNA encoding factors induced during blood feeding", Am. J. Trop. Med. Hyg., 66(3), 2002, pp. 225-233.
Li et al. "Construction of a linker library with widely controllable flexibility for fusion protein design", Applied Microbiology And Biotechnology, 2015; 100(1):215-225.
Metzner et al. "Extending the pharmacokinetic half-life of coagulation factors by fusion to recombinant albumin", Thromb Haemost 2013; 110: pp. 931-939.
Sheffield et al. "Fusion to Human Serum Albumin Extends the Circulatory Half-Life and Duration of Antithrombotic Action of the Kunitz Protease Inhibitor Domain of Protease Nexin 2", Cell Physiol Biochem 2018;45:772-782.
Sheffield et al. "Prolonged in vivo anticoagulant activity of a hirudin-albumin fusion protein secreted from Pichia Pastoris", Blood Coagul Fibrinolysis 2001, 12:433-443.
Zhao et al. "Increasing the homogeneity, stability and activity of human serum albumin and interferon-a2b fusion protein by linker engineering" Prot. Express. Purif. vol. 61, 2008, pp. 73-77.
Database Uniprot [Online] Subname: Full=Uncharacterized protein {ECO:0000313|EMBL:CAB55816.1}, Database accession No. Q9GP15, Oct. 25, 2017.
European Search Report issued in European Patent Application No. EP18164570.6 dated Aug. 20, 2018.
International Search Report for PCT/EP2019/057914 dated May 14, 2019, 7 pages.
Written Opinion of the ISA for PCT/EP2019/057914 dated May 14, 2019, 9 pages.

* cited by examiner

*Primary Examiner* — Hope A Robinson
(74) *Attorney, Agent, or Firm* — NIXON & VANDERHYE

(57) ABSTRACT

Disclosed is a fusion protein including an *Ixodes ricinus* salivary gland polypeptide. In particular, it relates to a fusion protein including at least one *Ixodes ricinus* salivary gland polypeptide, at least one serum albumin polypeptide and at least one linker peptide. Also disclosed is the use of such a fusion protein for preventing or treating thrombus formation and/or thrombus growth, as well as pharmaceutical compositions, medicaments and methods including such a fusion protein.

7 Claims, 10 Drawing Sheets

Specification includes a Sequence Listing.

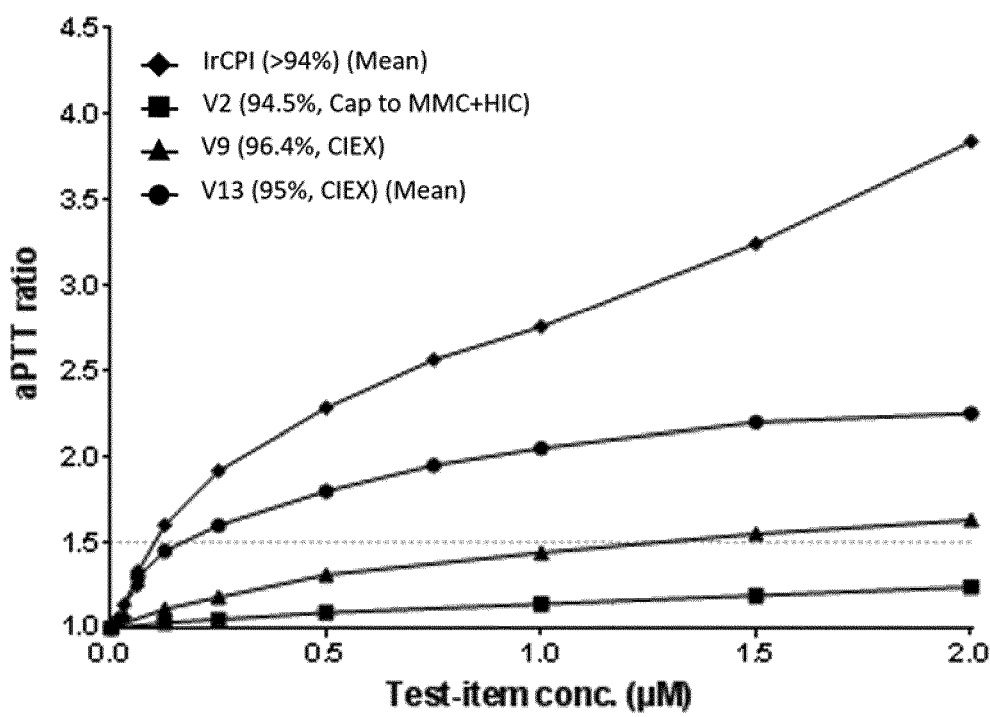
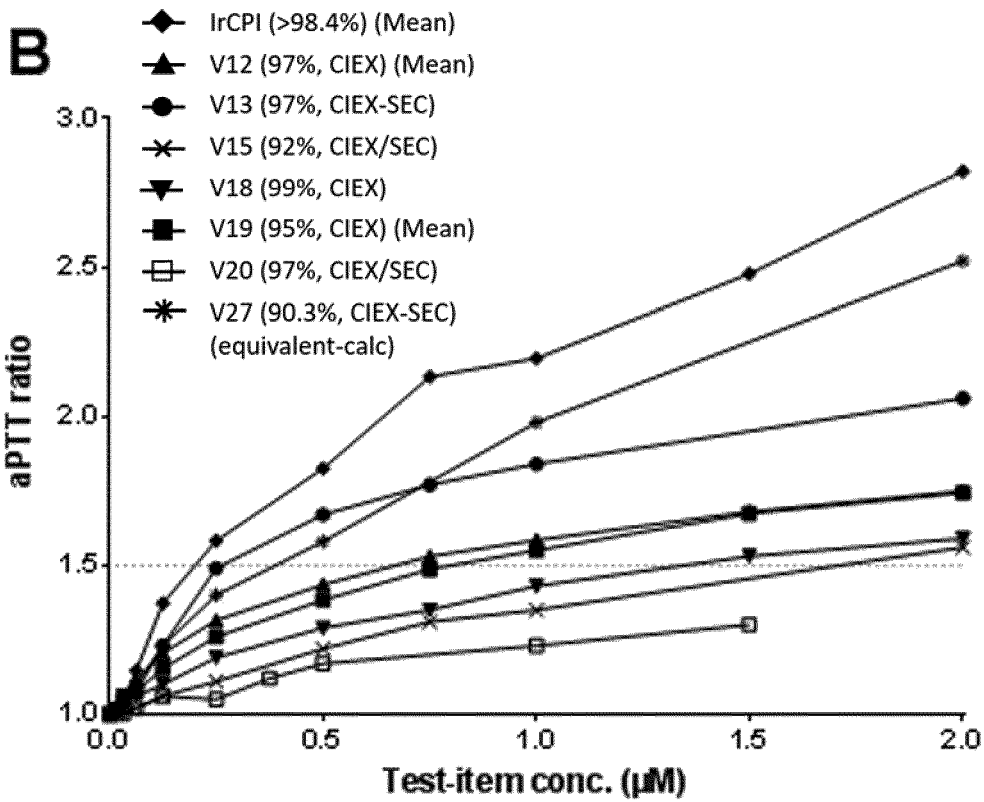
FIG. 2A-B

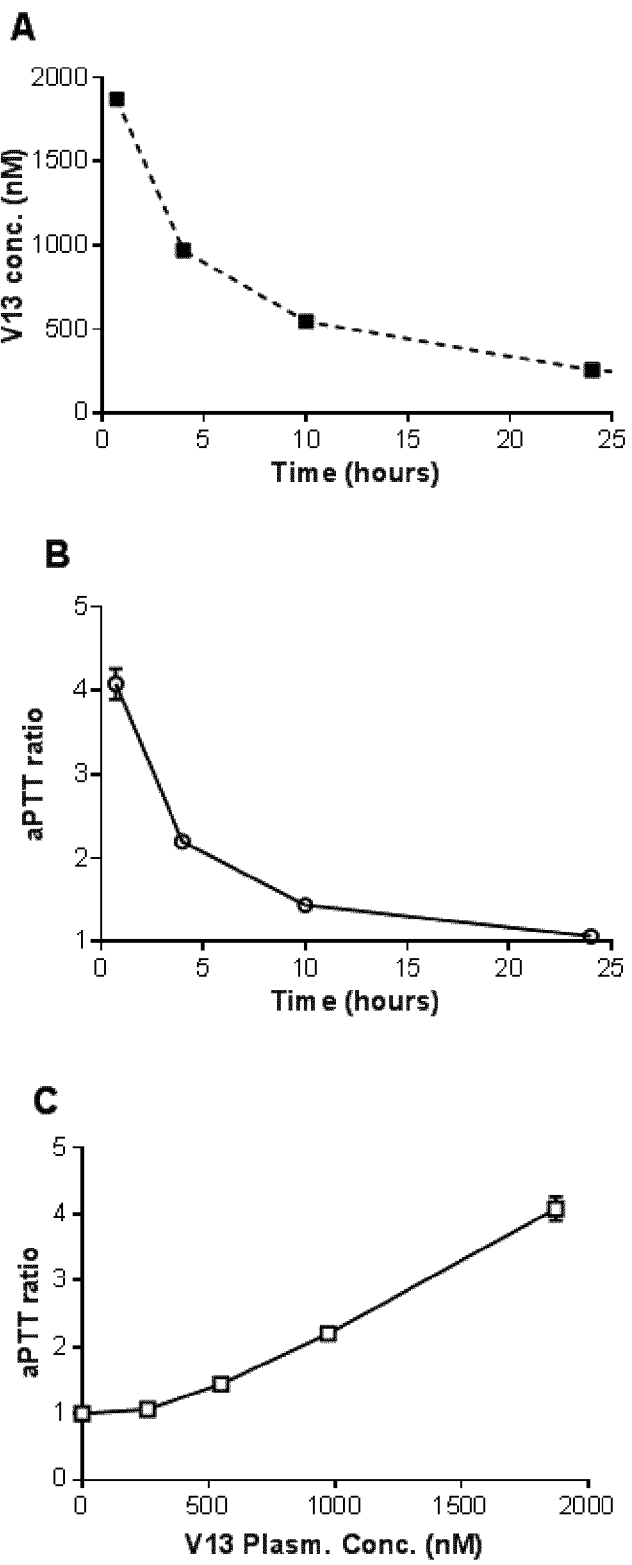
FIG. 3A-C

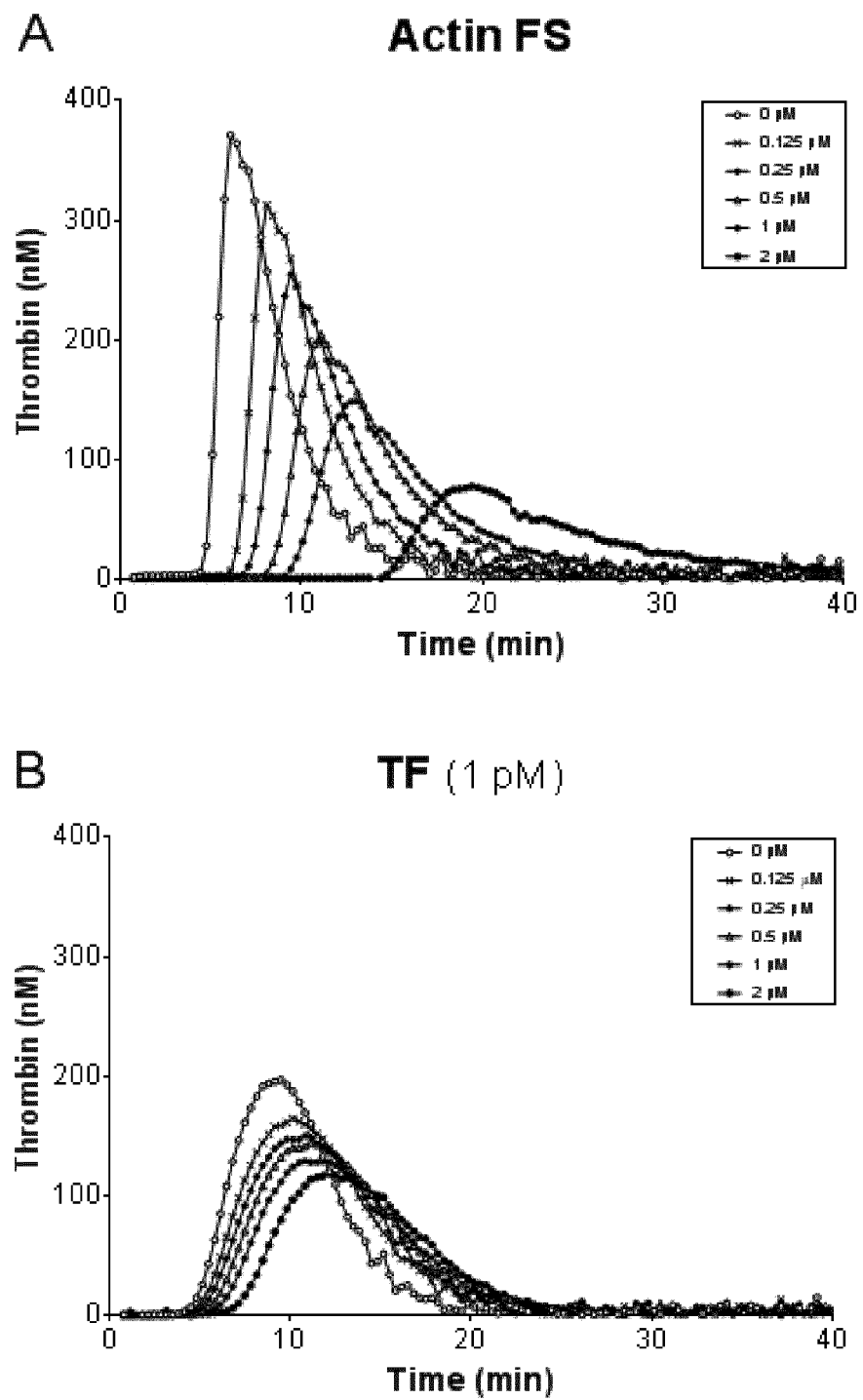
FIG. 7A-B

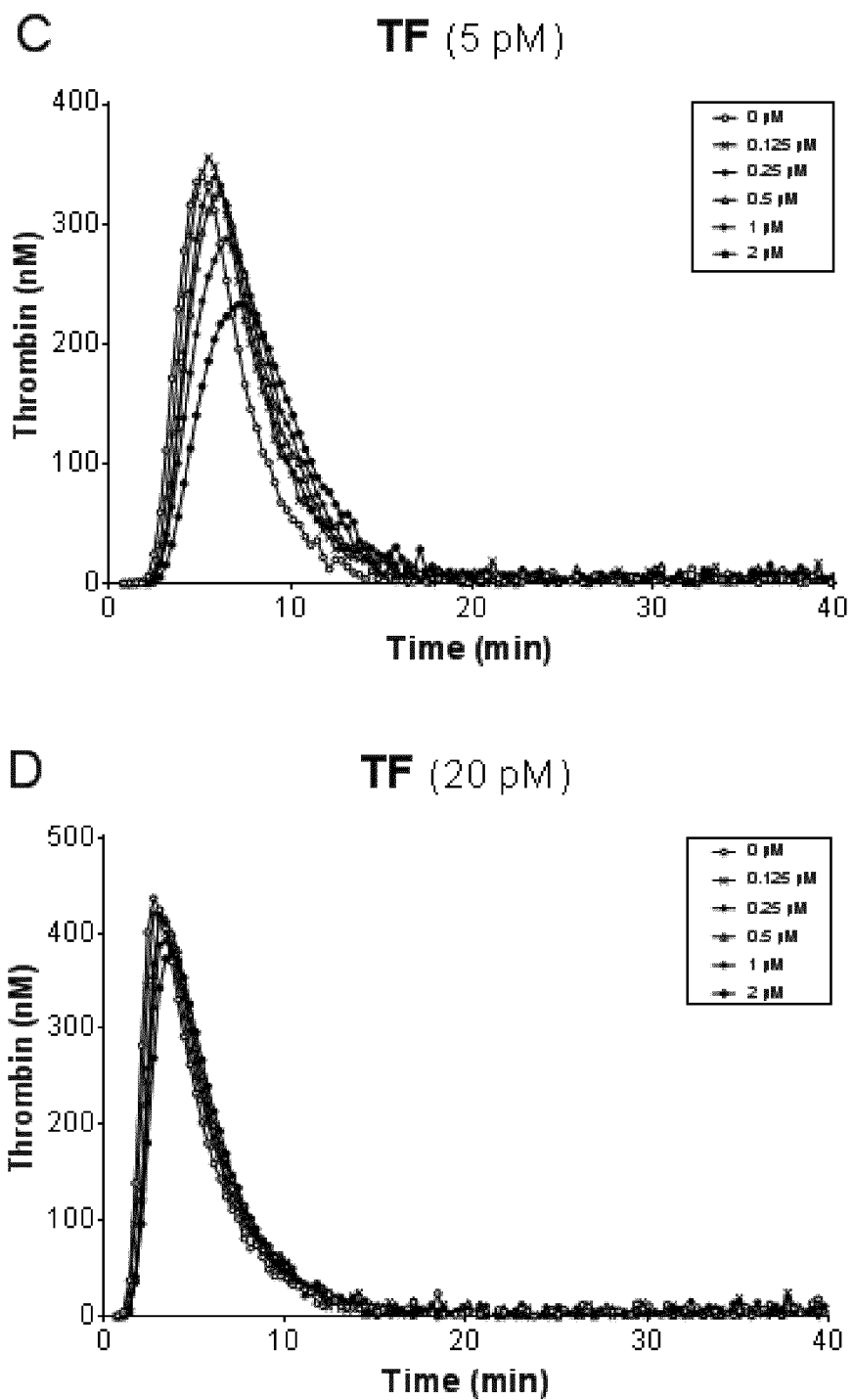
FIG. 7C-D

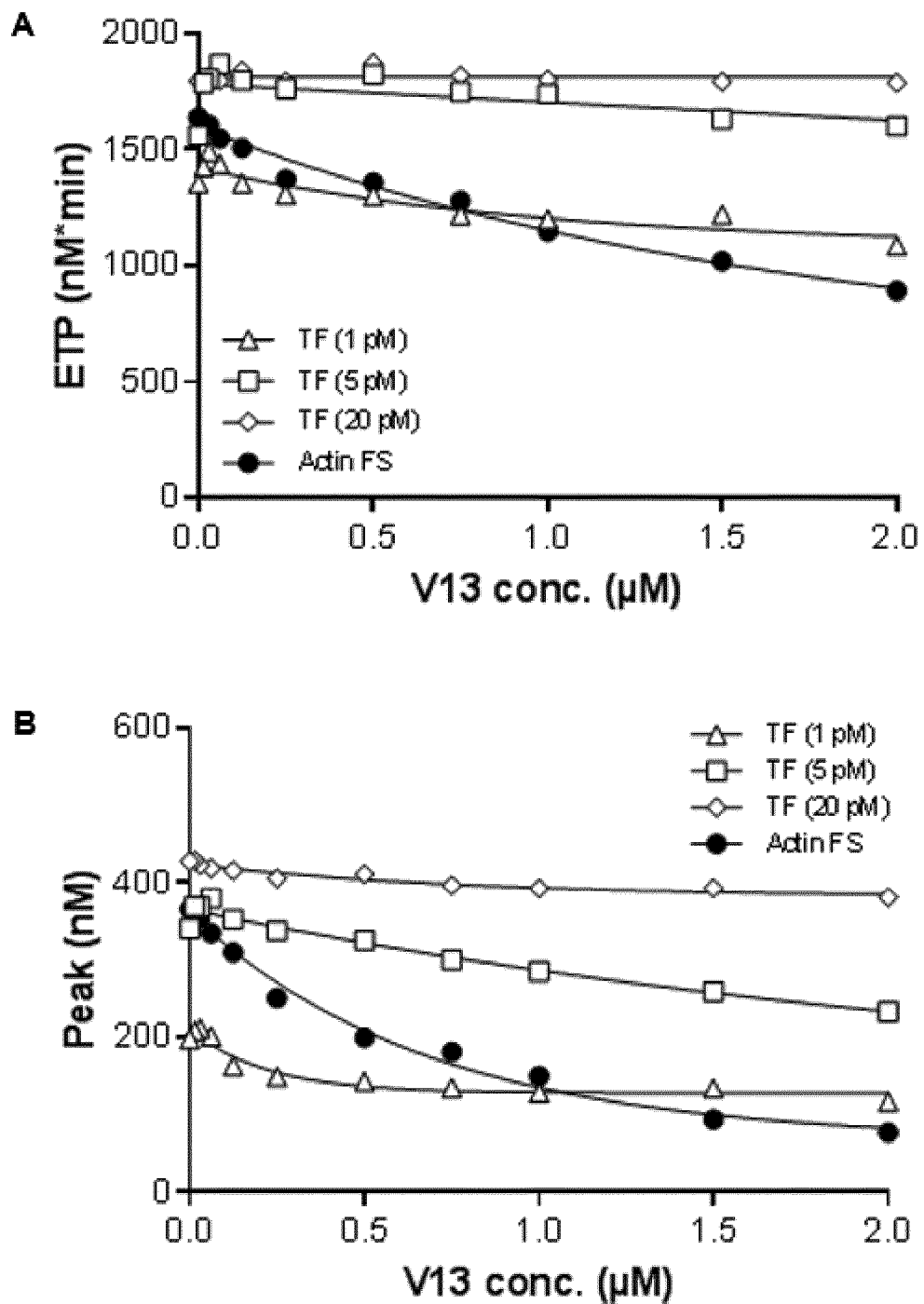
FIG. 8A-B

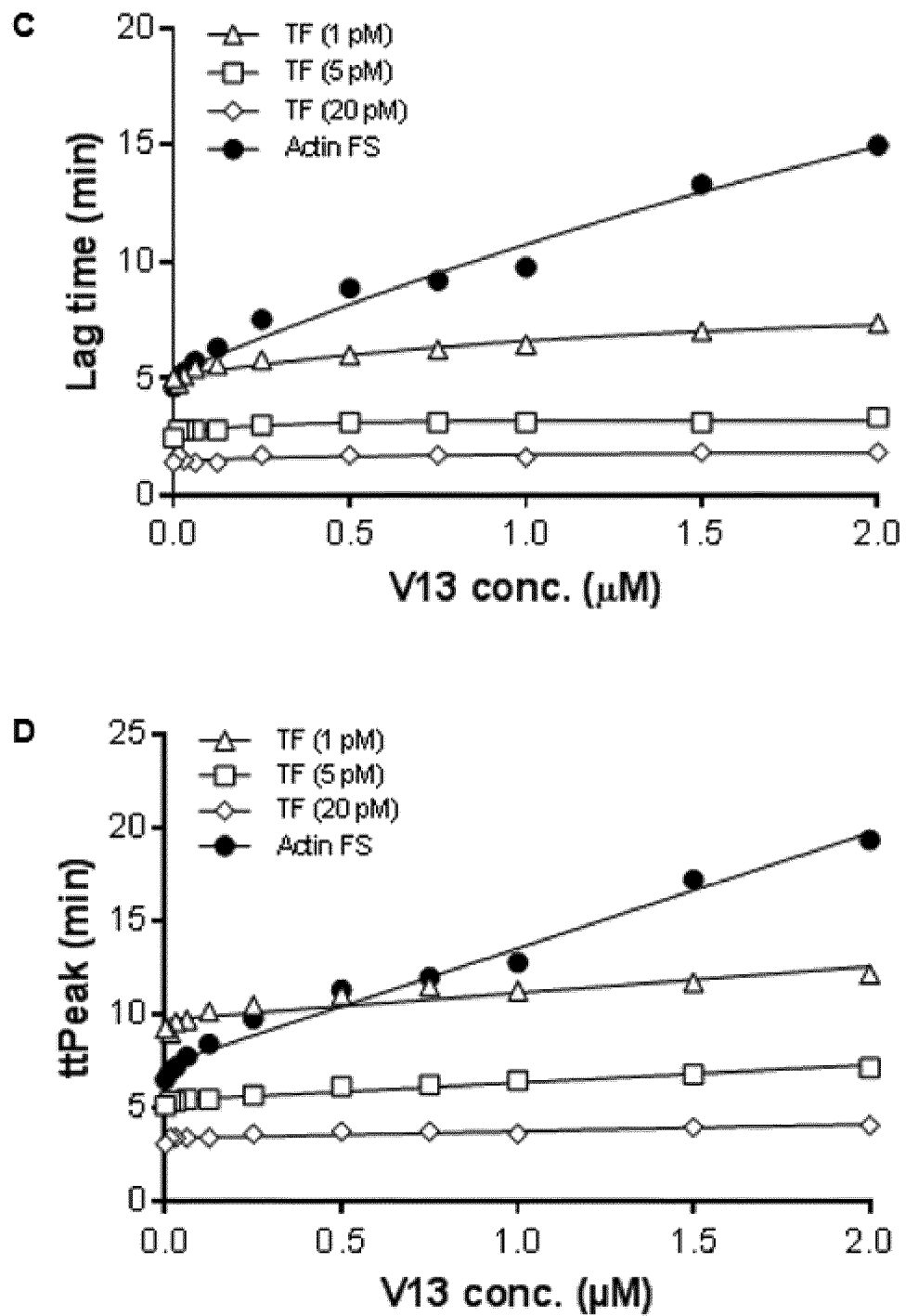
FIG. 8C-D

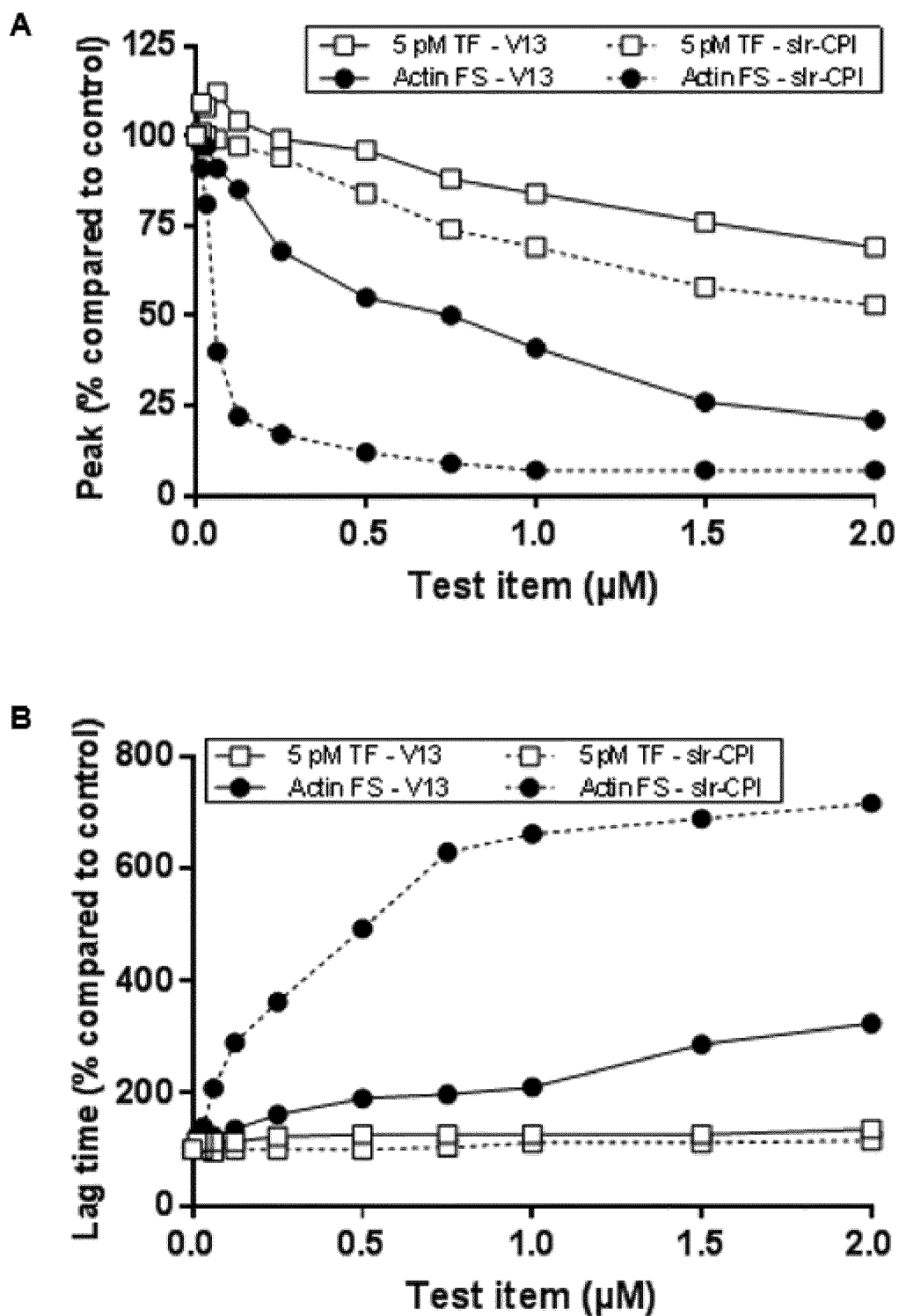
FIG. 9A-B

```
                        SEQUENCE LISTING

<160> NUMBER OF SEQ ID NOS: 52

<210> SEQ ID NO 1
<211> LENGTH: 67
<212> TYPE: PRT
<213> ORGANISM: Ixodes ricinus

<400> SEQUENCE: 1

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Asn Ile Thr Thr Cys Gln Glu Glu Cys Arg Ala
    50                  55                  60

Lys Lys Val
65

<210> SEQ ID NO 2
<211> LENGTH: 67
<212> TYPE: PRT
<213> ORGANISM: Artificial Sequence
<220> FEATURE:
<223> OTHER INFORMATION: variant

<400> SEQUENCE: 2

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Glu Cys Arg Ala
    50                  55                  60

Lys Lys Val
65

<210> SEQ ID NO 3
<211> LENGTH: 585
<212> TYPE: PRT
<213> ORGANISM: Homo sapiens
<220> FEATURE:
<223> OTHER INFORMATION: HSA polypeptide

<400> SEQUENCE: 3

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 4
<211> LENGTH: 652
<212> TYPE: PRT
<213> ORGANISM: Artificial Sequence
<220> FEATURE:
<223> OTHER INFORMATION: fusion protein

<400> SEQUENCE: 4

Ala Asn His Lys Gly Arg Gly Arg Pro Ala Lys Cys Lys Leu Pro Pro
1               5                   10                  15
Asp Asp Gly Pro Cys Arg Ala Arg Ile Pro Ser Tyr Tyr Phe Asp Arg
            20                  25                  30
Lys Thr Lys Thr Cys Lys Glu Phe Met Tyr Gly Gly Cys Glu Gly Asn
        35                  40                  45
Glu Asn Asn Phe Glu Gln Ile Thr Thr Cys Gln Glu Glu Cys Arg Ala
    50                  55                  60
Lys Lys Val Asp Ala His Lys Ser Glu Val Ala His Arg Phe Lys Asp
65                  70                  75                  80
Leu Gly Glu Glu Asn Phe Lys Ala Leu Val Leu Ile Ala Phe Ala Gln
                85                  90                  95
Tyr Leu Gln Gln Cys Pro Phe Glu Asp His Val Lys Leu Val Asn Glu
            100                 105                 110
Val Thr Glu Phe Ala Lys Thr Cys Val Ala Asp Glu Ser Ala Glu Asn
        115                 120                 125
Cys Asp Lys Ser Leu His Thr Leu Phe Gly Asp Lys Leu Cys Thr Val
    130                 135                 140
Ala Thr Leu Arg Glu Thr Tyr Gly Glu Met Ala Asp Cys Cys Ala Lys
145                 150                 155                 160
Gln Glu Pro Glu Arg Asn Glu Cys Phe Leu Gln His Lys Asp Asp Asn
                165                 170                 175
Pro Asn Leu Pro Arg Leu Val Arg Pro Glu Val Asp Val Met Cys Thr
            180                 185                 190
Ala Phe His Asp Asn Glu Glu Thr Phe Leu Lys Lys Tyr Leu Tyr Glu
        195                 200                 205
Ile Ala Arg Arg His Pro Tyr Phe Tyr Ala Pro Glu Leu Leu Phe Phe
    210                 215                 220
Ala Lys Arg Tyr Lys Ala Ala Phe Thr Glu Cys Cys Gln Ala Ala Asp
225                 230                 235                 240
Lys Ala Ala Cys Leu Leu Pro Lys Leu Asp Glu Leu Arg Asp Glu Gly
                245                 250                 255
Lys Ala Ser Ser Ala Lys Gln Arg Leu Lys Cys Ala Ser Leu Gln Lys
            260                 265                 270
```

Phe Gly Glu Arg Ala Phe Lys Ala Trp Ala Val Ala Arg Leu Ser Gln
            275                 280                 285

Arg Phe Pro Lys Ala Glu Phe Ala Glu Val Ser Lys Leu Val Thr Asp
        290                 295                 300

Leu Thr Lys Val His Thr Glu Cys Cys His Gly Asp Leu Leu Glu Cys
305                 310                 315                 320

Ala Asp Asp Arg Ala Asp Leu Ala Lys Tyr Ile Cys Glu Asn Gln Asp
                325                 330                 335

Ser Ile Ser Ser Lys Leu Lys Glu Cys Cys Glu Lys Pro Leu Leu Glu
            340                 345                 350

Lys Ser His Cys Ile Ala Glu Val Glu Asn Asp Glu Met Pro Ala Asp
        355                 360                 365

Leu Pro Ser Leu Ala Ala Asp Phe Val Glu Ser Lys Asp Val Cys Lys
370                 375                 380

Asn Tyr Ala Glu Ala Lys Asp Val Phe Leu Gly Met Phe Leu Tyr Glu
385                 390                 395                 400

Tyr Ala Arg Arg His Pro Asp Tyr Ser Val Val Leu Leu Leu Arg Leu
                405                 410                 415

Ala Lys Thr Tyr Glu Thr Thr Leu Glu Lys Cys Cys Ala Ala Ala Asp
            420                 425                 430

Pro His Glu Cys Tyr Ala Lys Val Phe Asp Glu Phe Lys Pro Leu Val
        435                 440                 445

Glu Glu Pro Gln Asn Leu Ile Lys Gln Asn Cys Glu Leu Phe Glu Gln
        450                 455                 460

Leu Gly Glu Tyr Lys Phe Gln Asn Ala Leu Leu Val Arg Tyr Thr Lys
465                 470                 475                 480

Lys Val Pro Gln Val Ser Thr Pro Thr Leu Val Glu Val Ser Arg Asn
                485                 490                 495

Leu Gly Lys Val Gly Ser Lys Cys Cys Lys His Pro Glu Ala Lys Arg
            500                 505                 510

Met Pro Cys Ala Glu Asp Tyr Leu Ser Val Val Leu Asn Gln Leu Cys
        515                 520                 525

Val Leu His Glu Lys Thr Pro Val Ser Asp Arg Val Thr Lys Cys Cys
530                 535                 540

Thr Glu Ser Leu Val Asn Arg Arg Pro Cys Phe Ser Ala Leu Glu Val
545                 550                 555                 560

Asp Glu Thr Tyr Val Pro Lys Glu Phe Asn Ala Glu Thr Phe Thr Phe
                565                 570                 575

His Ala Asp Ile Cys Thr Leu Ser Glu Lys Glu Arg Gln Ile Lys Lys
            580                 585                 590

Gln Thr Ala Leu Val Glu Leu Val Lys His Lys Pro Lys Ala Thr Lys
        595                 600                 605

Glu Gln Leu Lys Ala Val Met Asp Asp Phe Ala Ala Phe Val Glu Lys
610                 615                 620

Cys Cys Lys Ala Asp Asp Lys Glu Thr Cys Phe Ala Glu Glu Gly Lys
625                 630                 635                 640

Lys Leu Val Ala Ala Ser Gln Ala Ala Leu Gly Leu
                645                 650

<210> SEQ ID NO 5
<211> LENGTH: 652
<212> TYPE: PRT
<213> ORGANISM: Artificial Sequence
<220> FEATURE:
<223> OTHER INFORMATION: fusion protein

<400> SEQUENCE: 5

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
```

```
            405                 410                 415
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Asn His Lys Gly Arg Gly
            580                 585                 590

Arg Pro Ala Lys Cys Lys Leu Pro Pro Asp Asp Gly Pro Cys Arg Ala
            595                 600                 605

Arg Ile Pro Ser Tyr Tyr Phe Asp Arg Lys Thr Lys Thr Cys Lys Glu
    610                 615                 620

Phe Met Tyr Gly Gly Cys Glu Gly Asn Glu Asn Asn Phe Glu Gln Ile
625                 630                 635                 640

Thr Thr Cys Gln Glu Glu Cys Arg Ala Lys Lys Val
                645                 650

<210> SEQ ID NO 6
<211> LENGTH: 719
<212> TYPE: PRT
<213> ORGANISM: Artificial Sequence
<220> FEATURE:
<223> OTHER INFORMATION: fusion protein

<400> SEQUENCE: 6

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Glu Cys Arg Ala
    50                  55                  60

Lys Lys Val Ala Asn His Lys Gly Arg Gly Arg Pro Ala Lys Cys Lys
65                  70                  75                  80

Leu Pro Pro Asp Asp Gly Pro Cys Arg Ala Arg Ile Pro Ser Tyr Tyr
                85                  90                  95

Phe Asp Arg Lys Thr Lys Thr Cys Lys Glu Phe Met Tyr Gly Gly Cys
            100                 105                 110

Glu Gly Asn Glu Asn Asn Phe Glu Gln Ile Thr Thr Cys Gln Glu Glu
```

```
            115                 120                 125
Cys Arg Ala Lys Lys Val Asp Ala His Lys Ser Glu Val Ala His Arg
130                 135                 140

Phe Lys Asp Leu Gly Glu Glu Asn Phe Lys Ala Leu Val Leu Ile Ala
145                 150                 155                 160

Phe Ala Gln Tyr Leu Gln Gln Cys Pro Phe Glu Asp His Val Lys Leu
                165                 170                 175

Val Asn Glu Val Thr Glu Phe Ala Lys Thr Cys Val Ala Asp Glu Ser
                180                 185                 190

Ala Glu Asn Cys Asp Lys Ser Leu His Thr Leu Phe Gly Asp Lys Leu
                195                 200                 205

Cys Thr Val Ala Thr Leu Arg Glu Thr Tyr Gly Glu Met Ala Asp Cys
210                 215                 220

Cys Ala Lys Gln Glu Pro Glu Arg Asn Glu Cys Phe Leu Gln His Lys
225                 230                 235                 240

Asp Asp Asn Pro Asn Leu Pro Arg Leu Val Arg Pro Glu Val Asp Val
                245                 250                 255

Met Cys Thr Ala Phe His Asp Asn Glu Glu Thr Phe Leu Lys Lys Tyr
                260                 265                 270

Leu Tyr Glu Ile Ala Arg Arg His Pro Tyr Phe Tyr Ala Pro Glu Leu
                275                 280                 285

Leu Phe Phe Ala Lys Arg Tyr Lys Ala Ala Phe Thr Glu Cys Cys Gln
                290                 295                 300

Ala Ala Asp Lys Ala Ala Cys Leu Leu Pro Lys Leu Asp Glu Leu Arg
305                 310                 315                 320

Asp Glu Gly Lys Ala Ser Ser Ala Lys Gln Arg Leu Lys Cys Ala Ser
                325                 330                 335

Leu Gln Lys Phe Gly Glu Arg Ala Phe Lys Ala Trp Ala Val Ala Arg
                340                 345                 350

Leu Ser Gln Arg Phe Pro Lys Ala Glu Phe Ala Glu Val Ser Lys Leu
                355                 360                 365

Val Thr Asp Leu Thr Lys Val His Thr Glu Cys Cys His Gly Asp Leu
370                 375                 380

Leu Glu Cys Ala Asp Asp Arg Ala Asp Leu Ala Lys Tyr Ile Cys Glu
385                 390                 395                 400

Asn Gln Asp Ser Ile Ser Ser Lys Leu Lys Glu Cys Cys Glu Lys Pro
                405                 410                 415

Leu Leu Glu Lys Ser His Cys Ile Ala Glu Val Glu Asn Asp Glu Met
                420                 425                 430

Pro Ala Asp Leu Pro Ser Leu Ala Ala Asp Phe Val Glu Ser Lys Asp
                435                 440                 445

Val Cys Lys Asn Tyr Ala Glu Ala Lys Asp Val Phe Leu Gly Met Phe
450                 455                 460

Leu Tyr Glu Tyr Ala Arg Arg His Pro Asp Tyr Ser Val Val Leu Leu
465                 470                 475                 480

Leu Arg Leu Ala Lys Thr Tyr Glu Thr Thr Leu Glu Lys Cys Cys Ala
                485                 490                 495

Ala Ala Asp Pro His Glu Cys Tyr Ala Lys Val Phe Asp Glu Phe Lys
                500                 505                 510

Pro Leu Val Glu Glu Pro Gln Asn Leu Ile Lys Gln Asn Cys Glu Leu
                515                 520                 525

Phe Glu Gln Leu Gly Glu Tyr Lys Phe Gln Asn Ala Leu Leu Val Arg
530                 535                 540
```

Tyr Thr Lys Lys Val Pro Gln Val Ser Thr Pro Thr Leu Val Glu Val
545                 550                 555                 560

Ser Arg Asn Leu Gly Lys Val Gly Ser Lys Cys Cys Lys His Pro Glu
            565                 570                 575

Ala Lys Arg Met Pro Cys Ala Glu Asp Tyr Leu Ser Val Val Leu Asn
        580                 585                 590

Gln Leu Cys Val Leu His Glu Lys Thr Pro Val Ser Asp Arg Val Thr
            595                 600                 605

Lys Cys Cys Thr Glu Ser Leu Val Asn Arg Arg Pro Cys Phe Ser Ala
        610                 615                 620

Leu Glu Val Asp Glu Thr Tyr Val Pro Lys Glu Phe Asn Ala Glu Thr
625                 630                 635                 640

Phe Thr Phe His Ala Asp Ile Cys Thr Leu Ser Glu Lys Glu Arg Gln
                645                 650                 655

Ile Lys Lys Gln Thr Ala Leu Val Glu Leu Val Lys His Lys Pro Lys
            660                 665                 670

Ala Thr Lys Glu Gln Leu Lys Ala Val Met Asp Asp Phe Ala Ala Phe
        675                 680                 685

Val Glu Lys Cys Cys Lys Ala Asp Asp Lys Glu Thr Cys Phe Ala Glu
            690                 695                 700

Glu Gly Lys Lys Leu Val Ala Ala Ser Gln Ala Ala Leu Gly Leu
705                 710                 715

<210> SEQ ID NO 7
<211> LENGTH: 719
<212> TYPE: PRT
<213> ORGANISM: Artificial Sequence
<220> FEATURE:
<223> OTHER INFORMATION: fusion protein

<400> SEQUENCE: 7

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

```
Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Asn His Lys Gly Arg Gly
            580                 585                 590

Arg Pro Ala Lys Cys Lys Leu Pro Pro Asp Asp Gly Pro Cys Arg Ala
        595                 600                 605
```

```
Arg Ile Pro Ser Tyr Tyr Phe Asp Arg Lys Thr Lys Thr Cys Lys Glu
    610             615                 620

Phe Met Tyr Gly Gly Cys Glu Gly Asn Glu Asn Asn Phe Glu Gln Ile
625             630                 635                 640

Thr Thr Cys Gln Glu Glu Cys Arg Ala Lys Lys Val Ala Asn His Lys
            645                 650                 655

Gly Arg Gly Arg Pro Ala Lys Cys Lys Leu Pro Pro Asp Asp Gly Pro
            660                 665                 670

Cys Arg Ala Arg Ile Pro Ser Tyr Tyr Phe Asp Arg Lys Thr Lys Thr
            675                 680                 685

Cys Lys Glu Phe Met Tyr Gly Gly Cys Glu Gly Asn Glu Asn Asn Phe
    690             695                 700

Glu Gln Ile Thr Thr Cys Gln Glu Glu Cys Arg Ala Lys Lys Val
705             710                 715
```

```
<210> SEQ ID NO 8
<211> LENGTH: 4
<212> TYPE: PRT
<213> ORGANISM: Artificial Sequence
<220> FEATURE:
<221> NAME/KEY: REPEAT
<222> LOCATION: 1..4
<223> OTHER INFORMATION: n wherein n is a number from 1 to 10
<220> FEATURE:
<223> OTHER INFORMATION: linker

<400> SEQUENCE: 8

Gly Gly Gly Gly
1

<210> SEQ ID NO 9
<211> LENGTH: 4
<212> TYPE: PRT
<213> ORGANISM: Artificial Sequence
<220> FEATURE:
<221> NAME/KEY: REPEAT
<222> LOCATION: 1..4
<223> OTHER INFORMATION: n wherein n is a number from 1 to 10
<220> FEATURE:
<223> OTHER INFORMATION: linker

<400> SEQUENCE: 9

Ser Ser Ser Gly
1

<210> SEQ ID NO 10
<211> LENGTH: 5
<212> TYPE: PRT
<213> ORGANISM: Artificial Sequence
<220> FEATURE:
<221> NAME/KEY: REPEAT
<222> LOCATION: 1..5
<223> OTHER INFORMATION: m wherein m is a number from 1 to 10
<220> FEATURE:
<223> OTHER INFORMATION: linker

<400> SEQUENCE: 10

Gly Gly Gly Gly Ser
1               5

<210> SEQ ID NO 11
<211> LENGTH: 12
<212> TYPE: PRT
<213> ORGANISM: Artificial Sequence
<220> FEATURE:
<223> OTHER INFORMATION: linker
```

```
<400> SEQUENCE: 11

Gly Ser Ala Gly Ser Ala Ala Gly Ser Gly Glu Phe
1               5                   10

<210> SEQ ID NO 12
<211> LENGTH: 7
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: 3..5
<223> OTHER INFORMATION: n wherein n is a number from 1 to 20

<400> SEQUENCE: 12

Gly Ser Gly Gly Ser Gly Ser
1               5

<210> SEQ ID NO 13
<211> LENGTH: 751
<212> TYPE: PRT
<213> ORGANISM: Artificial Sequence
<220> FEATURE:
<223> OTHER INFORMATION: fusion protein

<400> SEQUENCE: 13

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
                20                  25                  30

Lys Thr Lys Thr Cys Lys Glu Phe Met Tyr Gly Gly Cys Glu Gly Asn
            35                  40                  45

Glu Asn Asn Phe Glu Gln Ile Thr Thr Cys Gln Glu Cys Arg Ala
        50                  55                  60

Lys Lys Val Gly Gly Gly Ser Gly Gly Gly Ser Gly Gly Gly
65              70                  75                  80

Gly Ser Ala Asp Ala His Lys Ser Glu Val Ala His Arg Phe Lys Asp
                85                  90                  95

Leu Gly Glu Glu Asn Phe Lys Ala Leu Val Leu Ile Ala Phe Ala Gln
            100                 105                 110

Tyr Leu Gln Gln Cys Pro Phe Glu Asp His Val Lys Leu Val Asn Glu
        115                 120                 125

Val Thr Glu Phe Ala Lys Thr Cys Val Ala Asp Glu Ser Ala Glu Asn
    130                 135                 140

Cys Asp Lys Ser Leu His Thr Leu Phe Gly Asp Lys Leu Cys Thr Val
145                 150                 155                 160

Ala Thr Leu Arg Glu Thr Tyr Gly Glu Met Ala Asp Cys Cys Ala Lys
                165                 170                 175

Gln Glu Pro Glu Arg Asn Glu Cys Phe Leu Gln His Lys Asp Asp Asn
            180                 185                 190

Pro Asn Leu Pro Arg Leu Val Arg Pro Glu Val Asp Val Met Cys Thr
        195                 200                 205

Ala Phe His Asp Asn Glu Glu Thr Phe Leu Lys Lys Tyr Leu Tyr Glu
    210                 215                 220

Ile Ala Arg Arg His Pro Tyr Phe Tyr Ala Pro Glu Leu Leu Phe Phe
225                 230                 235                 240

Ala Lys Arg Tyr Lys Ala Ala Phe Thr Glu Cys Cys Gln Ala Ala Asp
```

-continued

```
                245                 250                 255
Lys Ala Ala Cys Leu Leu Pro Lys Leu Asp Glu Leu Arg Asp Glu Gly
            260                 265                 270

Lys Ala Ser Ser Ala Lys Gln Arg Leu Lys Cys Ala Ser Leu Gln Lys
        275                 280                 285

Phe Gly Glu Arg Ala Phe Lys Ala Trp Ala Val Ala Arg Leu Ser Gln
290                 295                 300

Arg Phe Pro Lys Ala Glu Phe Ala Glu Val Ser Lys Leu Val Thr Asp
305                 310                 315                 320

Leu Thr Lys Val His Thr Glu Cys Cys His Gly Asp Leu Leu Glu Cys
                325                 330                 335

Ala Asp Asp Arg Ala Asp Leu Ala Lys Tyr Ile Cys Glu Asn Gln Asp
            340                 345                 350

Ser Ile Ser Ser Lys Leu Lys Glu Cys Cys Glu Lys Pro Leu Leu Glu
        355                 360                 365

Lys Ser His Cys Ile Ala Glu Val Glu Asn Asp Glu Met Pro Ala Asp
    370                 375                 380

Leu Pro Ser Leu Ala Ala Asp Phe Val Glu Ser Lys Asp Val Cys Lys
385                 390                 395                 400

Asn Tyr Ala Glu Ala Lys Asp Val Phe Leu Gly Met Phe Leu Tyr Glu
                405                 410                 415

Tyr Ala Arg Arg His Pro Asp Tyr Ser Val Val Leu Leu Leu Arg Leu
            420                 425                 430

Ala Lys Thr Tyr Glu Thr Thr Leu Glu Lys Cys Cys Ala Ala Ala Asp
        435                 440                 445

Pro His Glu Cys Tyr Ala Lys Val Phe Asp Glu Phe Lys Pro Leu Val
    450                 455                 460

Glu Glu Pro Gln Asn Leu Ile Lys Gln Asn Cys Glu Leu Phe Glu Gln
465                 470                 475                 480

Leu Gly Glu Tyr Lys Phe Gln Asn Ala Leu Leu Val Arg Tyr Thr Lys
                485                 490                 495

Lys Val Pro Gln Val Ser Thr Pro Thr Leu Val Glu Val Ser Arg Asn
            500                 505                 510

Leu Gly Lys Val Gly Ser Lys Cys Cys Lys His Pro Glu Ala Lys Arg
        515                 520                 525

Met Pro Cys Ala Glu Asp Tyr Leu Ser Val Val Leu Asn Gln Leu Cys
    530                 535                 540

Val Leu His Glu Lys Thr Pro Val Ser Asp Arg Val Thr Lys Cys Cys
545                 550                 555                 560

Thr Glu Ser Leu Val Asn Arg Arg Pro Cys Phe Ser Ala Leu Glu Val
                565                 570                 575

Asp Glu Thr Tyr Val Pro Lys Glu Phe Asn Ala Glu Thr Phe Thr Phe
            580                 585                 590

His Ala Asp Ile Cys Thr Leu Ser Glu Lys Glu Arg Gln Ile Lys Lys
        595                 600                 605

Gln Thr Ala Leu Val Glu Leu Val Lys His Lys Pro Lys Ala Thr Lys
    610                 615                 620

Glu Gln Leu Lys Ala Val Met Asp Asp Phe Ala Ala Phe Val Glu Lys
625                 630                 635                 640

Cys Cys Lys Ala Asp Asp Lys Glu Thr Cys Phe Ala Glu Glu Gly Lys
                645                 650                 655

Lys Leu Val Ala Ala Ser Gln Ala Ala Leu Gly Leu Gly Gly Gly Gly
            660                 665                 670
```

```
Ser Gly Gly Gly Ser Gly Gly Gly Ser Ala Ala Asn His Lys
        675             680             685

Gly Arg Gly Arg Pro Ala Lys Cys Lys Leu Pro Pro Asp Asp Gly Pro
    690             695             700

Cys Arg Ala Arg Ile Pro Ser Tyr Tyr Phe Asp Arg Lys Thr Lys Thr
705             710             715             720

Cys Lys Glu Phe Met Tyr Gly Gly Cys Glu Gly Asn Glu Asn Asn Phe
            725             730             735

Glu Gln Ile Thr Thr Cys Gln Glu Glu Cys Arg Ala Lys Lys Val
            740             745             750
```

<210> SEQ ID NO 14
<211> LENGTH: 5
<212> TYPE: PRT
<213> ORGANISM: Artificial Sequence
<220> FEATURE:
<221> NAME/KEY: REPEAT
<222> LOCATION: 1..5
<223> OTHER INFORMATION: n wherein n is a number from 1 to 10
<220> FEATURE:
<223> OTHER INFORMATION: linker

<400> SEQUENCE: 14

```
Glu Ala Ala Ala Lys
1               5
```

<210> SEQ ID NO 15
<211> LENGTH: 7
<212> TYPE: PRT
<213> ORGANISM: Artificial Sequence
<220> FEATURE:
<221> NAME/KEY: REPEAT
<222> LOCATION: 1..7
<223> OTHER INFORMATION: m wherein m is a number from 1 to 5
<220> FEATURE:
<223> OTHER INFORMATION: linker
<220> FEATURE:
<221> NAME/KEY: REPEAT
<222> LOCATION: 2..6
<223> OTHER INFORMATION: n wherein n is a number from 2 to 10

<400> SEQUENCE: 15

```
Ala Glu Ala Ala Ala Lys Ala
1               5
```

<210> SEQ ID NO 16
<211> LENGTH: 46
<212> TYPE: PRT
<213> ORGANISM: Artificial Sequence
<220> FEATURE:
<223> OTHER INFORMATION: linker

<400> SEQUENCE: 16

```
Ala Glu Ala Ala Ala Lys Glu Ala Ala Ala Lys Glu Ala Ala Ala Lys
1               5                   10                  15

Glu Ala Ala Ala Lys Ala Leu Glu Ala Ala Ala Lys Glu Ala
            20                  25                  30

Ala Ala Lys Glu Ala Ala Ala Lys Glu Ala Ala Ala Lys Ala
            35                  40                  45
```

<210> SEQ ID NO 17
<211> LENGTH: 775
<212> TYPE: PRT
<213> ORGANISM: Artificial Sequence
<220> FEATURE:

<223> OTHER INFORMATION: fusion protein

<400> SEQUENCE: 17

```
Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Cys Arg Ala
    50                  55                  60

Lys Lys Val Ala Pro Ala Pro Ala Pro Ala Pro Ala Pro Ala Pro Ala
65                  70                  75                  80

Pro Ala Pro Ala Pro Ala Pro Ala Pro Ala Pro Ala Pro Ala Pro Asp
                85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
        115                 120                 125

Cys Pro Phe Glu Asp His Val Lys Leu Val Asn Glu Val Thr Glu Phe
130                 135                 140

Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
                165                 170                 175

Glu Thr Tyr Gly Glu Met Ala Asp Cys Cys Ala Lys Gln Glu Pro Glu
            180                 185                 190

Arg Asn Glu Cys Phe Leu Gln His Lys Asp Asp Asn Pro Asn Leu Pro
        195                 200                 205

Arg Leu Val Arg Pro Glu Val Asp Val Met Cys Thr Ala Phe His Asp
210                 215                 220

Asn Glu Glu Thr Phe Leu Lys Lys Tyr Leu Tyr Glu Ile Ala Arg Arg
225                 230                 235                 240

His Pro Tyr Phe Tyr Ala Pro Glu Leu Leu Phe Phe Ala Lys Arg Tyr
                245                 250                 255

Lys Ala Ala Phe Thr Glu Cys Cys Gln Ala Ala Asp Lys Ala Ala Cys
            260                 265                 270

Leu Leu Pro Lys Leu Asp Glu Leu Arg Asp Glu Gly Lys Ala Ser Ser
        275                 280                 285

Ala Lys Gln Arg Leu Lys Cys Ala Ser Leu Gln Lys Phe Gly Glu Arg
290                 295                 300

Ala Phe Lys Ala Trp Ala Val Ala Arg Leu Ser Gln Arg Phe Pro Lys
305                 310                 315                 320

Ala Glu Phe Ala Glu Val Ser Lys Leu Val Thr Asp Leu Thr Lys Val
                325                 330                 335

His Thr Glu Cys Cys His Gly Asp Leu Leu Glu Cys Ala Asp Asp Arg
            340                 345                 350

Ala Asp Leu Ala Lys Tyr Ile Cys Glu Asn Gln Asp Ser Ile Ser Ser
        355                 360                 365

Lys Leu Lys Glu Cys Cys Glu Lys Pro Leu Leu Glu Lys Ser His Cys
370                 375                 380

Ile Ala Glu Val Glu Asn Asp Glu Met Pro Ala Asp Leu Pro Ser Leu
385                 390                 395                 400
```

```
Ala Ala Asp Phe Val Glu Ser Lys Asp Val Cys Lys Asn Tyr Ala Glu
            405                 410                 415
Ala Lys Asp Val Phe Leu Gly Met Phe Leu Tyr Glu Tyr Ala Arg Arg
        420                 425                 430
His Pro Asp Tyr Ser Val Val Leu Leu Leu Arg Leu Ala Lys Thr Tyr
    435                 440                 445
Glu Thr Thr Leu Glu Lys Cys Cys Ala Ala Asp Pro His Glu Cys
450                 455                 460
Tyr Ala Lys Val Phe Asp Glu Phe Lys Pro Leu Val Glu Glu Pro Gln
465                 470                 475                 480
Asn Leu Ile Lys Gln Asn Cys Glu Leu Phe Glu Gln Leu Gly Glu Tyr
                485                 490                 495
Lys Phe Gln Asn Ala Leu Leu Val Arg Tyr Thr Lys Lys Val Pro Gln
            500                 505                 510
Val Ser Thr Pro Thr Leu Val Glu Val Ser Arg Asn Leu Gly Lys Val
        515                 520                 525
Gly Ser Lys Cys Cys Lys His Pro Glu Ala Lys Arg Met Pro Cys Ala
    530                 535                 540
Glu Asp Tyr Leu Ser Val Val Leu Asn Gln Leu Cys Val Leu His Glu
545                 550                 555                 560
Lys Thr Pro Val Ser Asp Arg Val Thr Lys Cys Cys Thr Glu Ser Leu
                565                 570                 575
Val Asn Arg Arg Pro Cys Phe Ser Ala Leu Glu Val Asp Glu Thr Tyr
            580                 585                 590
Val Pro Lys Glu Phe Asn Ala Glu Thr Phe Thr Phe His Ala Asp Ile
        595                 600                 605
Cys Thr Leu Ser Glu Lys Glu Arg Gln Ile Lys Lys Gln Thr Ala Leu
    610                 615                 620
Val Glu Leu Val Lys His Lys Pro Lys Ala Thr Lys Glu Gln Leu Lys
625                 630                 635                 640
Ala Val Met Asp Asp Phe Ala Ala Phe Val Glu Lys Cys Cys Lys Ala
                645                 650                 655
Asp Asp Lys Glu Thr Cys Phe Ala Glu Glu Gly Lys Lys Leu Val Ala
            660                 665                 670
Ala Ser Gln Ala Ala Leu Gly Leu Ala Pro Ala Pro Ala Pro Ala Pro
        675                 680                 685
Ala Pro Ala Pro Ala Pro Ala Pro Ala Pro Ala Pro Ala Pro Ala Pro
    690                 695                 700
Ala Pro Ala Pro Ala Asn His Lys Gly Arg Gly Arg Pro Ala Lys Cys
705                 710                 715                 720
Lys Leu Pro Pro Asp Asp Gly Pro Cys Arg Ala Arg Ile Pro Ser Tyr
                725                 730                 735
Tyr Phe Asp Arg Lys Thr Lys Thr Cys Lys Glu Phe Met Tyr Gly Gly
            740                 745                 750
Cys Glu Gly Asn Glu Asn Asn Phe Glu Gln Ile Thr Thr Cys Gln Glu
        755                 760                 765
Glu Cys Arg Ala Lys Lys Val
770                 775

<210> SEQ ID NO 18
<211> LENGTH: 18
<212> TYPE: PRT
<213> ORGANISM: Artificial Sequence
<220> FEATURE:
<223> OTHER INFORMATION: linker
```

-continued

```
<400> SEQUENCE: 18

Lys Glu Ser Gly Ser Val Ser Ser Glu Gln Leu Ala Gln Phe Arg Ser
1               5                   10                  15

Leu Asp

<210> SEQ ID NO 19
<211> LENGTH: 14
<212> TYPE: PRT
<213> ORGANISM: Artificial Sequence
<220> FEATURE:
<223> OTHER INFORMATION: linker

<400> SEQUENCE: 19

Glu Gly Lys Ser Ser Gly Ser Gly Ser Glu Ser Lys Ser Thr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: linker

<400> SEQUENCE: 20

Ala Glu Ala Ala Ala Lys Glu Ala Ala Ala Lys Ala
1               5                   10

<210> SEQ ID NO 21
<211> LENGTH: 22
<212> TYPE: PRT
<213> ORGANISM: Artificial Sequence
<220> FEATURE:
<223> OTHER INFORMATION: linker

<400> SEQUENCE: 21

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 22
<211> LENGTH: 16
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: 2..6
<223> OTHER INFORMATION: n wherein n is a number from 1 to 10,
      preferably from 2 to 5
<220> FEATURE:
<221> NAME/KEY: REPEAT
<222> LOCATION: 11..15
<223> OTHER INFORMATION: m wherein m is a number from 1 to 10,
      preferably from 2 to 5

<400> SEQUENCE: 22

Ala Glu Ala Ala Ala Lys Ala Leu Glu Ala Glu Ala Ala Ala Lys Ala
1               5                   10                  15

<210> SEQ ID NO 23
<211> LENGTH: 5
<212> TYPE: PRT
<213> ORGANISM: Artificial Sequence
<220> FEATURE:
```

```
<223> OTHER INFORMATION: linker
<220> FEATURE:
<221> NAME/KEY: REPEAT
<222> LOCATION: 4..5
<223> OTHER INFORMATION: n wherein n is a number from 1 to 20

<400> SEQUENCE: 23

Pro Ala Pro Ala Pro
1               5

<210> SEQ ID NO 24
<211> LENGTH: 5
<212> TYPE: PRT
<213> ORGANISM: Artificial Sequence
<220> FEATURE:
<223> OTHER INFORMATION: linker

<400> SEQUENCE: 24

Pro Ala Pro Ala Pro
1               5

<210> SEQ ID NO 25
<211> LENGTH: 14
<212> TYPE: PRT
<213> ORGANISM: Artificial Sequence
<220> FEATURE:
<223> OTHER INFORMATION: linker

<400> SEQUENCE: 25

Ala Pro Ala Pro Ala Pro Ala Pro Ala Pro Ala Pro Ala Pro
1               5                   10

<210> SEQ ID NO 26
<211> LENGTH: 28
<212> TYPE: PRT
<213> ORGANISM: Artificial Sequence
<220> FEATURE:
<223> OTHER INFORMATION: linker

<400> SEQUENCE: 26

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro
            20                  25

<210> SEQ ID NO 27
<211> LENGTH: 16
<212> TYPE: PRT
<213> ORGANISM: Artificial Sequence
<220> FEATURE:
<223> OTHER INFORMATION: linker

<400> SEQUENCE: 27

Gly Gly Gly Gly Ser Gly Gly Gly Gly Ser Gly Gly Gly Gly Ser Ala
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: linker

<400> SEQUENCE: 28

Gly Ser Gly Gly Ser Gly Gly Ser Gly Gly Ser Gly Gly Ser Gly Ser
1               5                   10                  15
```

<210> SEQ ID NO 29
<211> LENGTH: 31
<212> TYPE: PRT
<213> ORGANISM: Artificial Sequence
<220> FEATURE:
<223> OTHER INFORMATION: linker

<400> SEQUENCE: 29

```
Gly Ser Gly Gly Ser Gly Gly Ser Gly Gly Ser Gly Gly Ser Gly Gly
1               5                   10                  15
Ser Gly Gly Ser Gly Gly Ser Gly Gly Ser Gly Gly Ser Gly Ser
                20                  25                  30
```

<210> SEQ ID NO 30
<211> LENGTH: 664
<212> TYPE: PRT
<213> ORGANISM: Artificial Sequence
<220> FEATURE:
<223> OTHER INFORMATION: fusion protein

<400> SEQUENCE: 30

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Glu Ala Ala Lys Glu
                580                 585                 590

Ala Ala Ala Lys Ala Ala Asn His Lys Gly Arg Gly Arg Pro Ala Lys
            595                 600                 605

Cys Lys Leu Pro Pro Asp Asp Gly Pro Cys Arg Ala Arg Ile Pro Ser
610                 615                 620

Tyr Tyr Phe Asp Arg Lys Thr Lys Thr Cys Lys Glu Phe Met Tyr Gly
625                 630                 635                 640

Gly Cys Glu Gly Asn Glu Asn Asn Phe Glu Gln Ile Thr Thr Cys Gln
                645                 650                 655

Glu Glu Cys Arg Ala Lys Lys Val
                660

<210> SEQ ID NO 31
<211> LENGTH: 666
<212> TYPE: PRT
<213> ORGANISM: Artificial Sequence
<220> FEATURE:

<223> OTHER INFORMATION: fusion protein

<400> SEQUENCE: 31

```
Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Cys Arg Ala
    50                  55                  60

Lys Lys Val Ala Pro Ala Pro Ala Pro Ala Pro Ala Pro Ala Pro Ala
65              70                  75                  80

Pro Asp Ala His Lys Ser Glu Val Ala His Arg Phe Lys Asp Leu Gly
            85                  90                  95

Glu Glu Asn Phe Lys Ala Leu Val Leu Ile Ala Phe Ala Gln Tyr Leu
            100                 105                 110

Gln Gln Cys Pro Phe Glu Asp His Val Lys Leu Val Asn Glu Val Thr
        115                 120                 125

Glu Phe Ala Lys Thr Cys Val Ala Asp Glu Ser Ala Glu Asn Cys Asp
130                 135                 140

Lys Ser Leu His Thr Leu Phe Gly Asp Lys Leu Cys Thr Val Ala Thr
145                 150                 155                 160

Leu Arg Glu Thr Tyr Gly Glu Met Ala Asp Cys Cys Ala Lys Gln Glu
            165                 170                 175

Pro Glu Arg Asn Glu Cys Phe Leu Gln His Lys Asp Asp Asn Pro Asn
        180                 185                 190

Leu Pro Arg Leu Val Arg Pro Glu Val Asp Val Met Cys Thr Ala Phe
    195                 200                 205

His Asp Asn Glu Glu Thr Phe Leu Lys Lys Tyr Leu Tyr Glu Ile Ala
210                 215                 220

Arg Arg His Pro Tyr Phe Tyr Ala Pro Glu Leu Leu Phe Phe Ala Lys
225                 230                 235                 240

Arg Tyr Lys Ala Ala Phe Thr Glu Cys Cys Gln Ala Ala Asp Lys Ala
            245                 250                 255

Ala Cys Leu Leu Pro Lys Leu Asp Glu Leu Arg Asp Glu Gly Lys Ala
        260                 265                 270

Ser Ser Ala Lys Gln Arg Leu Lys Cys Ala Ser Leu Gln Lys Phe Gly
    275                 280                 285

Glu Arg Ala Phe Lys Ala Trp Ala Val Ala Arg Leu Ser Gln Arg Phe
290                 295                 300

Pro Lys Ala Glu Phe Ala Glu Val Ser Lys Leu Val Thr Asp Leu Thr
305                 310                 315                 320

Lys Val His Thr Glu Cys Cys His Gly Asp Leu Leu Glu Cys Ala Asp
            325                 330                 335

Asp Arg Ala Asp Leu Ala Lys Tyr Ile Cys Glu Asn Gln Asp Ser Ile
        340                 345                 350

Ser Ser Lys Leu Lys Glu Cys Cys Glu Lys Pro Leu Leu Glu Lys Ser
    355                 360                 365

His Cys Ile Ala Glu Val Glu Asn Asp Glu Met Pro Ala Asp Leu Pro
370                 375                 380

Ser Leu Ala Ala Asp Phe Val Glu Ser Lys Asp Val Cys Lys Asn Tyr
385                 390                 395                 400
```

```
Ala Glu Ala Lys Asp Val Phe Leu Gly Met Phe Leu Tyr Glu Tyr Ala
            405                 410                 415

Arg Arg His Pro Asp Tyr Ser Val Val Leu Leu Leu Arg Leu Ala Lys
            420                 425                 430

Thr Tyr Glu Thr Thr Leu Glu Lys Cys Cys Ala Ala Ala Asp Pro His
            435                 440                 445

Glu Cys Tyr Ala Lys Val Phe Asp Glu Phe Lys Pro Leu Val Glu Glu
            450                 455                 460

Pro Gln Asn Leu Ile Lys Gln Asn Cys Glu Leu Phe Glu Gln Leu Gly
465                 470                 475                 480

Glu Tyr Lys Phe Gln Asn Ala Leu Leu Val Arg Tyr Thr Lys Lys Val
            485                 490                 495

Pro Gln Val Ser Thr Pro Thr Leu Val Glu Val Ser Arg Asn Leu Gly
            500                 505                 510

Lys Val Gly Ser Lys Cys Cys Lys His Pro Glu Ala Lys Arg Met Pro
            515                 520                 525

Cys Ala Glu Asp Tyr Leu Ser Val Val Leu Asn Gln Leu Cys Val Leu
            530                 535                 540

His Glu Lys Thr Pro Val Ser Asp Arg Val Thr Lys Cys Cys Thr Glu
545                 550                 555                 560

Ser Leu Val Asn Arg Arg Pro Cys Phe Ser Ala Leu Glu Val Asp Glu
            565                 570                 575

Thr Tyr Val Pro Lys Glu Phe Asn Ala Glu Thr Phe Thr Phe His Ala
            580                 585                 590

Asp Ile Cys Thr Leu Ser Glu Lys Glu Arg Gln Ile Lys Lys Gln Thr
            595                 600                 605

Ala Leu Val Glu Leu Val Lys His Lys Pro Lys Ala Thr Lys Glu Gln
            610                 615                 620

Leu Lys Ala Val Met Asp Asp Phe Ala Ala Phe Val Glu Lys Cys Cys
625                 630                 635                 640

Lys Ala Asp Asp Lys Glu Thr Cys Phe Ala Glu Glu Gly Lys Lys Leu
            645                 650                 655

Val Ala Ala Ser Gln Ala Ala Leu Gly Leu
            660                 665

<210> SEQ ID NO 32
<211> LENGTH: 664
<212> TYPE: PRT
<213> ORGANISM: Artificial Sequence
<220> FEATURE:
<223> OTHER INFORMATION: fusion protein

<400> SEQUENCE: 32

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
            35                  40                  45

Glu Asn Asn Phe Glu Gln Ile Thr Thr Cys Gln Glu Glu Cys Arg Ala
            50                  55                  60

Lys Lys Val Ala Glu Ala Ala Lys Glu Ala Ala Lys Ala Asp
65                  70                  75                  80

Ala His Lys Ser Glu Val Ala His Arg Phe Lys Asp Leu Gly Glu Glu
            85                  90                  95
```

```
Asn Phe Lys Ala Leu Val Leu Ile Ala Phe Ala Gln Tyr Leu Gln Gln
                100                 105                 110

Cys Pro Phe Glu Asp His Val Lys Leu Val Asn Glu Val Thr Glu Phe
            115                 120                 125

Ala Lys Thr Cys Val Ala Asp Glu Ser Ala Glu Asn Cys Asp Lys Ser
130                 135                 140

Leu His Thr Leu Phe Gly Asp Lys Leu Cys Thr Val Ala Thr Leu Arg
145                 150                 155                 160

Glu Thr Tyr Gly Glu Met Ala Asp Cys Cys Ala Lys Gln Glu Pro Glu
                165                 170                 175

Arg Asn Glu Cys Phe Leu Gln His Lys Asp Asp Asn Pro Asn Leu Pro
            180                 185                 190

Arg Leu Val Arg Pro Glu Val Asp Val Met Cys Thr Ala Phe His Asp
        195                 200                 205

Asn Glu Glu Thr Phe Leu Lys Lys Tyr Leu Tyr Glu Ile Ala Arg Arg
    210                 215                 220

His Pro Tyr Phe Tyr Ala Pro Glu Leu Leu Phe Phe Ala Lys Arg Tyr
225                 230                 235                 240

Lys Ala Ala Phe Thr Glu Cys Cys Gln Ala Ala Asp Lys Ala Ala Cys
                245                 250                 255

Leu Leu Pro Lys Leu Asp Glu Leu Arg Asp Glu Gly Lys Ala Ser Ser
            260                 265                 270

Ala Lys Gln Arg Leu Lys Cys Ala Ser Leu Gln Lys Phe Gly Glu Arg
        275                 280                 285

Ala Phe Lys Ala Trp Ala Val Ala Arg Leu Ser Gln Arg Phe Pro Lys
    290                 295                 300

Ala Glu Phe Ala Glu Val Ser Lys Leu Val Thr Asp Leu Thr Lys Val
305                 310                 315                 320

His Thr Glu Cys Cys His Gly Asp Leu Leu Glu Cys Ala Asp Asp Arg
                325                 330                 335

Ala Asp Leu Ala Lys Tyr Ile Cys Glu Asn Gln Asp Ser Ile Ser Ser
            340                 345                 350

Lys Leu Lys Glu Cys Cys Glu Lys Pro Leu Leu Glu Lys Ser His Cys
        355                 360                 365

Ile Ala Glu Val Glu Asn Asp Glu Met Pro Ala Asp Leu Pro Ser Leu
    370                 375                 380

Ala Ala Asp Phe Val Glu Ser Lys Asp Val Cys Lys Asn Tyr Ala Glu
385                 390                 395                 400

Ala Lys Asp Val Phe Leu Gly Met Phe Leu Tyr Glu Tyr Ala Arg Arg
                405                 410                 415

His Pro Asp Tyr Ser Val Val Leu Leu Leu Arg Leu Ala Lys Thr Tyr
            420                 425                 430

Glu Thr Thr Leu Glu Lys Cys Cys Ala Ala Ala Asp Pro His Glu Cys
        435                 440                 445

Tyr Ala Lys Val Phe Asp Glu Phe Lys Pro Leu Val Glu Glu Pro Gln
    450                 455                 460

Asn Leu Ile Lys Gln Asn Cys Glu Leu Phe Glu Gln Leu Gly Glu Tyr
465                 470                 475                 480

Lys Phe Gln Asn Ala Leu Leu Val Arg Tyr Thr Lys Lys Val Pro Gln
                485                 490                 495

Val Ser Thr Pro Thr Leu Val Glu Val Ser Arg Asn Leu Gly Lys Val
            500                 505                 510

Gly Ser Lys Cys Cys Lys His Pro Glu Ala Lys Arg Met Pro Cys Ala
```

-continued

```
               515                 520                 525

Glu Asp Tyr Leu Ser Val Val Leu Asn Gln Leu Cys Val Leu His Glu
530                 535                 540

Lys Thr Pro Val Ser Asp Arg Val Thr Lys Cys Cys Thr Glu Ser Leu
545                 550                 555                 560

Val Asn Arg Arg Pro Cys Phe Ser Ala Leu Glu Val Asp Glu Thr Tyr
                565                 570                 575

Val Pro Lys Glu Phe Asn Ala Glu Thr Phe Thr Phe His Ala Asp Ile
            580                 585                 590

Cys Thr Leu Ser Glu Lys Glu Arg Gln Ile Lys Lys Gln Thr Ala Leu
        595                 600                 605

Val Glu Leu Val Lys His Lys Pro Lys Ala Thr Lys Glu Gln Leu Lys
    610                 615                 620

Ala Val Met Asp Asp Phe Ala Ala Phe Val Glu Lys Cys Cys Lys Ala
625                 630                 635                 640

Asp Asp Lys Glu Thr Cys Phe Ala Glu Glu Gly Lys Lys Leu Val Ala
                645                 650                 655

Ala Ser Gln Ala Ala Leu Gly Leu
                660

<210> SEQ ID NO 33
<211> LENGTH: 674
<212> TYPE: PRT
<213> ORGANISM: Artificial Sequence
<220> FEATURE:
<223> OTHER INFORMATION: fusion protein

<400> SEQUENCE: 33

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Glu Cys Arg Ala
50                  55                  60

Lys Lys Val Ala Glu Ala Ala Lys Glu Ala Ala Lys Glu Ala
65                  70                  75                  80

Ala Ala Lys Glu Ala Ala Lys Ala Asp Ala His Lys Ser Glu Val
                85                  90                  95

Ala His Arg Phe Lys Asp Leu Gly Glu Glu Asn Phe Lys Ala Leu Val
            100                 105                 110

Leu Ile Ala Phe Ala Gln Tyr Leu Gln Gln Cys Pro Phe Glu Asp His
        115                 120                 125

Val Lys Leu Val Asn Glu Val Thr Glu Phe Ala Lys Thr Cys Val Ala
    130                 135                 140

Asp Glu Ser Ala Glu Asn Cys Asp Lys Ser Leu His Thr Leu Phe Gly
145                 150                 155                 160

Asp Lys Leu Cys Thr Val Ala Thr Leu Arg Glu Thr Tyr Gly Glu Met
                165                 170                 175

Ala Asp Cys Cys Ala Lys Gln Glu Pro Glu Arg Asn Glu Cys Phe Leu
            180                 185                 190

Gln His Lys Asp Asp Asn Pro Asn Leu Pro Arg Leu Val Arg Pro Glu
        195                 200                 205

Val Asp Val Met Cys Thr Ala Phe His Asp Asn Glu Glu Thr Phe Leu
```

-continued

```
            210                 215                 220
Lys Lys Tyr Leu Tyr Glu Ile Ala Arg Arg His Pro Tyr Phe Tyr Ala
225                 230                 235                 240

Pro Glu Leu Leu Phe Phe Ala Lys Arg Tyr Lys Ala Ala Phe Thr Glu
                    245                 250                 255

Cys Cys Gln Ala Ala Asp Lys Ala Ala Cys Leu Leu Pro Lys Leu Asp
                260                 265                 270

Glu Leu Arg Asp Glu Gly Lys Ala Ser Ser Ala Lys Gln Arg Leu Lys
            275                 280                 285

Cys Ala Ser Leu Gln Lys Phe Gly Glu Arg Ala Phe Lys Ala Trp Ala
        290                 295                 300

Val Ala Arg Leu Ser Gln Arg Phe Pro Lys Ala Glu Phe Ala Glu Val
305                 310                 315                 320

Ser Lys Leu Val Thr Asp Leu Thr Lys Val His Thr Glu Cys Cys His
                325                 330                 335

Gly Asp Leu Leu Glu Cys Ala Asp Asp Arg Ala Asp Leu Ala Lys Tyr
                340                 345                 350

Ile Cys Glu Asn Gln Asp Ser Ile Ser Ser Lys Leu Lys Glu Cys Cys
            355                 360                 365

Glu Lys Pro Leu Leu Glu Lys Ser His Cys Ile Ala Glu Val Glu Asn
        370                 375                 380

Asp Glu Met Pro Ala Asp Leu Pro Ser Leu Ala Ala Asp Phe Val Glu
385                 390                 395                 400

Ser Lys Asp Val Cys Lys Asn Tyr Ala Glu Ala Lys Asp Val Phe Leu
                405                 410                 415

Gly Met Phe Leu Tyr Glu Tyr Ala Arg Arg His Pro Asp Tyr Ser Val
                420                 425                 430

Val Leu Leu Leu Arg Leu Ala Lys Thr Tyr Glu Thr Thr Leu Glu Lys
            435                 440                 445

Cys Cys Ala Ala Ala Asp Pro His Glu Cys Tyr Ala Lys Val Phe Asp
        450                 455                 460

Glu Phe Lys Pro Leu Val Glu Glu Pro Gln Asn Leu Ile Lys Gln Asn
465                 470                 475                 480

Cys Glu Leu Phe Glu Gln Leu Gly Glu Tyr Lys Phe Gln Asn Ala Leu
                485                 490                 495

Leu Val Arg Tyr Thr Lys Lys Val Pro Gln Val Ser Thr Pro Thr Leu
                500                 505                 510

Val Glu Val Ser Arg Asn Leu Gly Lys Val Gly Ser Lys Cys Cys Lys
            515                 520                 525

His Pro Glu Ala Lys Arg Met Pro Cys Ala Glu Asp Tyr Leu Ser Val
        530                 535                 540

Val Leu Asn Gln Leu Cys Val Leu His Glu Lys Thr Pro Val Ser Asp
545                 550                 555                 560

Arg Val Thr Lys Cys Cys Thr Glu Ser Leu Val Asn Arg Arg Pro Cys
                565                 570                 575

Phe Ser Ala Leu Glu Val Asp Glu Thr Tyr Val Pro Lys Glu Phe Asn
                580                 585                 590

Ala Glu Thr Phe Thr Phe His Ala Asp Ile Cys Thr Leu Ser Glu Lys
            595                 600                 605

Glu Arg Gln Ile Lys Lys Gln Thr Ala Leu Val Glu Leu Val Lys His
        610                 615                 620

Lys Pro Lys Ala Thr Lys Glu Gln Leu Lys Ala Val Met Asp Asp Phe
625                 630                 635                 640
```

```
Ala Ala Phe Val Glu Lys Cys Cys Lys Ala Asp Asp Lys Glu Thr Cys
            645                 650                 655

Phe Ala Glu Glu Gly Lys Lys Leu Val Ala Ala Ser Gln Ala Ala Leu
            660                 665                 670

Gly Leu

<210> SEQ ID NO 34
<211> LENGTH: 674
<212> TYPE: PRT
<213> ORGANISM: Artificial Sequence
<220> FEATURE:
<223> OTHER INFORMATION: fusion protein

<400> SEQUENCE: 34

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320
```

```
Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Glu Ala Ala Ala Lys Glu
            580                 585                 590

Ala Ala Ala Lys Glu Ala Ala Ala Lys Glu Ala Ala Ala Lys Ala Ala
        595                 600                 605

Asn His Lys Gly Arg Gly Arg Pro Ala Lys Cys Lys Leu Pro Pro Asp
    610                 615                 620

Asp Gly Pro Cys Arg Ala Arg Ile Pro Ser Tyr Tyr Phe Asp Arg Lys
625                 630                 635                 640

Thr Lys Thr Cys Lys Glu Phe Met Tyr Gly Gly Cys Glu Gly Asn Glu
                645                 650                 655

Asn Asn Phe Glu Gln Ile Thr Thr Cys Gln Glu Cys Arg Ala Lys
            660                 665                 670

Lys Val

<210> SEQ ID NO 35
<211> LENGTH: 698
<212> TYPE: PRT
<213> ORGANISM: Artificial Sequence
<220> FEATURE:
<223> OTHER INFORMATION: fusion protein

<400> SEQUENCE: 35

Ala Asn His Lys Gly Arg Gly Arg Pro Ala Lys Cys Lys Leu Pro Pro
```

-continued

```
1               5                   10                  15
Asp Asp Gly Pro Cys Arg Ala Arg Ile Pro Ser Tyr Tyr Phe Asp Arg
                20                  25                  30
Lys Thr Lys Thr Cys Lys Glu Phe Met Tyr Gly Gly Cys Glu Gly Asn
                35                  40                  45
Glu Asn Asn Phe Glu Gln Ile Thr Thr Cys Gln Glu Glu Cys Arg Ala
            50                  55                  60
Lys Lys Val Ala Glu Ala Ala Lys Glu Ala Ala Lys Glu Ala
65                  70                  75                  80
Ala Ala Lys Glu Ala Ala Lys Ala Leu Glu Ala Glu Ala Ala
                85                  90                  95
Lys Glu Ala Ala Ala Lys Glu Ala Ala Ala Lys Glu Ala Ala Ala Lys
                100                 105                 110
Ala Asp Ala His Lys Ser Glu Val Ala His Arg Phe Lys Asp Leu Gly
                115                 120                 125
Glu Glu Asn Phe Lys Ala Leu Val Leu Ile Ala Phe Ala Gln Tyr Leu
                130                 135                 140
Gln Gln Cys Pro Phe Glu Asp His Val Lys Leu Val Asn Glu Val Thr
145                 150                 155                 160
Glu Phe Ala Lys Thr Cys Val Ala Asp Glu Ser Ala Glu Asn Cys Asp
                165                 170                 175
Lys Ser Leu His Thr Leu Phe Gly Asp Lys Leu Cys Thr Val Ala Thr
                180                 185                 190
Leu Arg Glu Thr Tyr Gly Glu Met Ala Asp Cys Cys Ala Lys Gln Glu
                195                 200                 205
Pro Glu Arg Asn Glu Cys Phe Leu Gln His Lys Asp Asp Asn Pro Asn
                210                 215                 220
Leu Pro Arg Leu Val Arg Pro Glu Val Asp Val Met Cys Thr Ala Phe
225                 230                 235                 240
His Asp Asn Glu Glu Thr Phe Leu Lys Lys Tyr Leu Tyr Glu Ile Ala
                245                 250                 255
Arg Arg His Pro Tyr Phe Tyr Ala Pro Glu Leu Leu Phe Phe Ala Lys
                260                 265                 270
Arg Tyr Lys Ala Ala Phe Thr Glu Cys Cys Gln Ala Ala Asp Lys Ala
                275                 280                 285
Ala Cys Leu Leu Pro Lys Leu Asp Glu Leu Arg Asp Glu Gly Lys Ala
                290                 295                 300
Ser Ser Ala Lys Gln Arg Leu Lys Cys Ala Ser Leu Gln Lys Phe Gly
305                 310                 315                 320
Glu Arg Ala Phe Lys Ala Trp Ala Val Ala Arg Leu Ser Gln Arg Phe
                325                 330                 335
Pro Lys Ala Glu Phe Ala Glu Val Ser Lys Leu Val Thr Asp Leu Thr
                340                 345                 350
Lys Val His Thr Glu Cys Cys His Gly Asp Leu Leu Glu Cys Ala Asp
                355                 360                 365
Asp Arg Ala Asp Leu Ala Lys Tyr Ile Cys Glu Asn Gln Asp Ser Ile
                370                 375                 380
Ser Ser Lys Leu Lys Glu Cys Cys Glu Lys Pro Leu Leu Glu Lys Ser
385                 390                 395                 400
His Cys Ile Ala Glu Val Glu Asn Asp Glu Met Pro Ala Asp Leu Pro
                405                 410                 415
Ser Leu Ala Ala Asp Phe Val Glu Ser Lys Asp Val Cys Lys Asn Tyr
                420                 425                 430
```

```
Ala Glu Ala Lys Asp Val Phe Leu Gly Met Phe Leu Tyr Glu Tyr Ala
            435                 440                 445

Arg Arg His Pro Asp Tyr Ser Val Val Leu Leu Arg Leu Ala Lys
        450                 455                 460

Thr Tyr Glu Thr Thr Leu Glu Lys Cys Cys Ala Ala Ala Asp Pro His
465                 470                 475                 480

Glu Cys Tyr Ala Lys Val Phe Asp Glu Phe Lys Pro Leu Val Glu Glu
                485                 490                 495

Pro Gln Asn Leu Ile Lys Gln Asn Cys Glu Leu Phe Glu Gln Leu Gly
                500                 505                 510

Glu Tyr Lys Phe Gln Asn Ala Leu Leu Val Arg Tyr Thr Lys Lys Val
                515                 520                 525

Pro Gln Val Ser Thr Pro Thr Leu Val Glu Val Ser Arg Asn Leu Gly
                530                 535                 540

Lys Val Gly Ser Lys Cys Cys Lys His Pro Glu Ala Lys Arg Met Pro
545                 550                 555                 560

Cys Ala Glu Asp Tyr Leu Ser Val Val Leu Asn Gln Leu Cys Val Leu
                565                 570                 575

His Glu Lys Thr Pro Val Ser Asp Arg Val Thr Lys Cys Cys Thr Glu
                580                 585                 590

Ser Leu Val Asn Arg Arg Pro Cys Phe Ser Ala Leu Glu Val Asp Glu
                595                 600                 605

Thr Tyr Val Pro Lys Glu Phe Asn Ala Glu Thr Phe Thr Phe His Ala
                610                 615                 620

Asp Ile Cys Thr Leu Ser Glu Lys Glu Arg Gln Ile Lys Lys Gln Thr
625                 630                 635                 640

Ala Leu Val Glu Leu Val Lys His Lys Pro Lys Ala Thr Lys Glu Gln
                645                 650                 655

Leu Lys Ala Val Met Asp Asp Phe Ala Ala Phe Val Glu Lys Cys Cys
                660                 665                 670

Lys Ala Asp Asp Lys Glu Thr Cys Phe Ala Glu Glu Gly Lys Lys Leu
                675                 680                 685

Val Ala Ala Ser Gln Ala Ala Leu Gly Leu
                690                 695

<210> SEQ ID NO 36
<211> LENGTH: 698
<212> TYPE: PRT
<213> ORGANISM: Artificial Sequence
<220> FEATURE:
<223> OTHER INFORMATION: fusion protein

<400> SEQUENCE: 36

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65              70                  75                  80

Arg Glu Thr Tyr Gly Glu Met Ala Asp Cys Cys Ala Lys Gln Glu Pro
                85                  90                  95
```

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

```
Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Ala Ala Ala Lys Glu
                580                 585                 590

Ala Ala Ala Lys Glu Ala Ala Lys Glu Ala Ala Lys Ala Leu
            595                 600                 605

Glu Ala Glu Ala Ala Ala Lys Glu Ala Ala Lys Glu Ala Ala
    610                 615                 620

Lys Glu Ala Ala Ala Lys Ala Ala Asn His Lys Gly Arg Gly Arg Pro
625                 630                 635                 640

Ala Lys Cys Lys Leu Pro Pro Asp Asp Gly Pro Cys Arg Ala Arg Ile
                645                 650                 655

Pro Ser Tyr Tyr Phe Asp Arg Lys Thr Lys Thr Cys Lys Glu Phe Met
                660                 665                 670

Tyr Gly Gly Cys Glu Gly Asn Glu Asn Asn Phe Glu Gln Ile Thr Thr
                675                 680                 685

Cys Gln Glu Glu Cys Arg Ala Lys Lys Val
            690                 695

<210> SEQ ID NO 37
<211> LENGTH: 666
<212> TYPE: PRT
<213> ORGANISM: Artificial Sequence
<220> FEATURE:
<223> OTHER INFORMATION: fusion protein

<400> SEQUENCE: 37

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175
```

-continued

```
Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Ala Asn His Lys Gly Arg Gly Arg Pro
```

```
            595                 600                 605
Ala Lys Cys Lys Leu Pro Pro Asp Asp Gly Pro Cys Arg Ala Arg Ile
    610                 615                 620

Pro Ser Tyr Tyr Phe Asp Arg Lys Thr Lys Thr Cys Lys Glu Phe Met
625                 630                 635                 640

Tyr Gly Gly Cys Glu Gly Asn Glu Asn Asn Phe Glu Gln Ile Thr Thr
                645                 650                 655

Cys Gln Glu Glu Cys Arg Ala Lys Lys Val
            660                 665

<210> SEQ ID NO 38
<211> LENGTH: 680
<212> TYPE: PRT
<213> ORGANISM: Artificial Sequence
<220> FEATURE:
<223> OTHER INFORMATION: fusion protein

<400> SEQUENCE: 38

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Glu Cys Arg Ala
    50                  55                  60

Lys Lys Val Ala Pro Ala Pro Ala Pro Ala Pro Ala Pro Ala Pro Ala
65                  70                  75                  80

Pro Ala Pro Ala Pro Ala Pro Ala Pro Ala Pro Ala Pro Ala Pro Asp
                85                  90                  95

Ala His Lys Ser Glu Val Ala His Arg Phe Lys Asp Leu Gly Glu Glu
            100                 105                 110

Asn Phe Lys Ala Leu Val Leu Ile Ala Phe Ala Gln Tyr Leu Gln Gln
        115                 120                 125

Cys Pro Phe Glu Asp His Val Lys Leu Val Asn Glu Val Thr Glu Phe
130                 135                 140

Ala Lys Thr Cys Val Ala Asp Glu Ser Ala Glu Asn Cys Asp Lys Ser
145                 150                 155                 160

Leu His Thr Leu Phe Gly Asp Lys Leu Cys Thr Val Ala Thr Leu Arg
                165                 170                 175

Glu Thr Tyr Gly Glu Met Ala Asp Cys Cys Ala Lys Gln Glu Pro Glu
            180                 185                 190

Arg Asn Glu Cys Phe Leu Gln His Lys Asp Asp Asn Pro Asn Leu Pro
        195                 200                 205

Arg Leu Val Arg Pro Glu Val Asp Val Met Cys Thr Ala Phe His Asp
210                 215                 220

Asn Glu Glu Thr Phe Leu Lys Lys Tyr Leu Tyr Glu Ile Ala Arg Arg
225                 230                 235                 240

His Pro Tyr Phe Tyr Ala Pro Glu Leu Leu Phe Phe Ala Lys Arg Tyr
                245                 250                 255

Lys Ala Ala Phe Thr Glu Cys Cys Gln Ala Ala Asp Lys Ala Ala Cys
            260                 265                 270

Leu Leu Pro Lys Leu Asp Glu Leu Arg Asp Glu Gly Lys Ala Ser Ser
        275                 280                 285

Ala Lys Gln Arg Leu Lys Cys Ala Ser Leu Gln Lys Phe Gly Glu Arg
```

```
            290                 295                 300
Ala Phe Lys Ala Trp Ala Val Ala Arg Leu Ser Gln Arg Phe Pro Lys
305                 310                 315                 320

Ala Glu Phe Ala Glu Val Ser Lys Leu Val Thr Asp Leu Thr Lys Val
                325                 330                 335

His Thr Glu Cys Cys His Gly Asp Leu Leu Glu Cys Ala Asp Asp Arg
                340                 345                 350

Ala Asp Leu Ala Lys Tyr Ile Cys Glu Asn Gln Asp Ser Ile Ser Ser
                355                 360                 365

Lys Leu Lys Glu Cys Cys Glu Lys Pro Leu Leu Glu Lys Ser His Cys
370                 375                 380

Ile Ala Glu Val Glu Asn Asp Glu Met Pro Ala Asp Leu Pro Ser Leu
385                 390                 395                 400

Ala Ala Asp Phe Val Glu Ser Lys Asp Val Cys Lys Asn Tyr Ala Glu
                405                 410                 415

Ala Lys Asp Val Phe Leu Gly Met Phe Leu Tyr Glu Tyr Ala Arg Arg
                420                 425                 430

His Pro Asp Tyr Ser Val Val Leu Leu Leu Arg Leu Ala Lys Thr Tyr
                435                 440                 445

Glu Thr Thr Leu Glu Lys Cys Cys Ala Ala Ala Asp Pro His Glu Cys
                450                 455                 460

Tyr Ala Lys Val Phe Asp Glu Phe Lys Pro Leu Val Glu Glu Pro Gln
465                 470                 475                 480

Asn Leu Ile Lys Gln Asn Cys Glu Leu Phe Glu Gln Leu Gly Glu Tyr
                485                 490                 495

Lys Phe Gln Asn Ala Leu Leu Val Arg Tyr Thr Lys Lys Val Pro Gln
                500                 505                 510

Val Ser Thr Pro Thr Leu Val Glu Val Ser Arg Asn Leu Gly Lys Val
                515                 520                 525

Gly Ser Lys Cys Cys Lys His Pro Glu Ala Lys Arg Met Pro Cys Ala
530                 535                 540

Glu Asp Tyr Leu Ser Val Val Leu Asn Gln Leu Cys Val Leu His Glu
545                 550                 555                 560

Lys Thr Pro Val Ser Asp Arg Val Thr Lys Cys Cys Thr Glu Ser Leu
                565                 570                 575

Val Asn Arg Arg Pro Cys Phe Ser Ala Leu Glu Val Asp Glu Thr Tyr
                580                 585                 590

Val Pro Lys Glu Phe Asn Ala Glu Thr Phe Thr Phe His Ala Asp Ile
                595                 600                 605

Cys Thr Leu Ser Glu Lys Glu Arg Gln Ile Lys Lys Gln Thr Ala Leu
610                 615                 620

Val Glu Leu Val Lys His Lys Pro Lys Ala Thr Lys Glu Gln Leu Lys
625                 630                 635                 640

Ala Val Met Asp Asp Phe Ala Ala Phe Val Glu Lys Cys Cys Lys Ala
                645                 650                 655

Asp Asp Lys Glu Thr Cys Phe Ala Glu Glu Gly Lys Lys Leu Val Ala
                660                 665                 670

Ala Ser Gln Ala Ala Leu Gly Leu
                675                 680

<210> SEQ ID NO 39
<211> LENGTH: 680
<212> TYPE: PRT
<213> ORGANISM: Artificial Sequence
```

<220> FEATURE:
<223> OTHER INFORMATION: fusion protein

<400> SEQUENCE: 39

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

```
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Ala Pro Ala Pro Ala Pro Ala Pro Ala
        595                 600                 605

Pro Ala Pro Ala Pro Ala Asn His Lys Gly Arg Gly Arg Pro Ala Lys
    610                 615                 620

Cys Lys Leu Pro Pro Asp Asp Gly Pro Cys Arg Ala Arg Ile Pro Ser
625                 630                 635                 640

Tyr Tyr Phe Asp Arg Lys Thr Lys Thr Cys Lys Glu Phe Met Tyr Gly
                645                 650                 655

Gly Cys Glu Gly Asn Glu Asn Asn Phe Glu Gln Ile Thr Thr Cys Gln
            660                 665                 670

Glu Glu Cys Arg Ala Lys Lys Val
        675                 680

<210> SEQ ID NO 40
<211> LENGTH: 657
<212> TYPE: PRT
<213> ORGANISM: Artificial Sequence
<220> FEATURE:
<223> OTHER INFORMATION: fusion protein

<400> SEQUENCE: 40

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Glu Cys Arg Ala
    50                  55                  60

Lys Lys Val Pro Ala Pro Ala Pro Asp Ala His Lys Ser Glu Val Ala
65                  70                  75                  80
```

```
His Arg Phe Lys Asp Leu Gly Glu Glu Asn Phe Lys Ala Leu Val Leu
             85                   90                  95

Ile Ala Phe Ala Gln Tyr Leu Gln Gln Cys Pro Phe Glu Asp His Val
            100                 105                 110

Lys Leu Val Asn Glu Val Thr Glu Phe Ala Lys Thr Cys Val Ala Asp
            115                 120                 125

Glu Ser Ala Glu Asn Cys Asp Lys Ser Leu His Thr Leu Phe Gly Asp
        130                 135                 140

Lys Leu Cys Thr Val Ala Thr Leu Arg Glu Thr Tyr Gly Glu Met Ala
145                 150                 155                 160

Asp Cys Cys Ala Lys Gln Glu Pro Glu Arg Asn Glu Cys Phe Leu Gln
                165                 170                 175

His Lys Asp Asp Asn Pro Asn Leu Pro Arg Leu Val Arg Pro Glu Val
            180                 185                 190

Asp Val Met Cys Thr Ala Phe His Asp Asn Glu Glu Thr Phe Leu Lys
        195                 200                 205

Lys Tyr Leu Tyr Glu Ile Ala Arg Arg His Pro Tyr Phe Tyr Ala Pro
    210                 215                 220

Glu Leu Leu Phe Phe Ala Lys Arg Tyr Lys Ala Ala Phe Thr Glu Cys
225                 230                 235                 240

Cys Gln Ala Ala Asp Lys Ala Ala Cys Leu Leu Pro Lys Leu Asp Glu
                245                 250                 255

Leu Arg Asp Glu Gly Lys Ala Ser Ser Ala Lys Gln Arg Leu Lys Cys
            260                 265                 270

Ala Ser Leu Gln Lys Phe Gly Glu Arg Ala Phe Lys Ala Trp Ala Val
        275                 280                 285

Ala Arg Leu Ser Gln Arg Phe Pro Lys Ala Glu Phe Ala Glu Val Ser
    290                 295                 300

Lys Leu Val Thr Asp Leu Thr Lys Val His Thr Glu Cys Cys His Gly
305                 310                 315                 320

Asp Leu Leu Glu Cys Ala Asp Asp Arg Ala Asp Leu Ala Lys Tyr Ile
                325                 330                 335

Cys Glu Asn Gln Asp Ser Ile Ser Ser Lys Leu Lys Glu Cys Cys Glu
            340                 345                 350

Lys Pro Leu Leu Glu Lys Ser His Cys Ile Ala Glu Val Glu Asn Asp
        355                 360                 365

Glu Met Pro Ala Asp Leu Pro Ser Leu Ala Ala Asp Phe Val Glu Ser
    370                 375                 380

Lys Asp Val Cys Lys Asn Tyr Ala Glu Ala Lys Asp Val Phe Leu Gly
385                 390                 395                 400

Met Phe Leu Tyr Glu Tyr Ala Arg Arg His Pro Asp Tyr Ser Val Val
                405                 410                 415

Leu Leu Leu Arg Leu Ala Lys Thr Tyr Glu Thr Thr Leu Glu Lys Cys
            420                 425                 430

Cys Ala Ala Ala Asp Pro His Glu Cys Tyr Ala Lys Val Phe Asp Glu
        435                 440                 445

Phe Lys Pro Leu Val Glu Glu Pro Gln Asn Leu Ile Lys Gln Asn Cys
    450                 455                 460

Glu Leu Phe Glu Gln Leu Gly Glu Tyr Lys Phe Gln Asn Ala Leu Leu
465                 470                 475                 480

Val Arg Tyr Thr Lys Lys Val Pro Gln Val Ser Thr Pro Thr Leu Val
                485                 490                 495
```

```
Glu Val Ser Arg Asn Leu Gly Lys Val Gly Ser Lys Cys Cys Lys His
            500                 505                 510
Pro Glu Ala Lys Arg Met Pro Cys Ala Glu Asp Tyr Leu Ser Val Val
            515                 520                 525
Leu Asn Gln Leu Cys Val Leu His Glu Lys Thr Pro Val Ser Asp Arg
        530                 535                 540
Val Thr Lys Cys Cys Thr Glu Ser Leu Val Asn Arg Arg Pro Cys Phe
545                 550                 555                 560
Ser Ala Leu Glu Val Asp Glu Thr Tyr Val Pro Lys Glu Phe Asn Ala
                565                 570                 575
Glu Thr Phe Thr Phe His Ala Asp Ile Cys Thr Leu Ser Glu Lys Glu
            580                 585                 590
Arg Gln Ile Lys Lys Gln Thr Ala Leu Val Glu Leu Val Lys His Lys
            595                 600                 605
Pro Lys Ala Thr Lys Glu Gln Leu Lys Ala Val Met Asp Asp Phe Ala
        610                 615                 620
Ala Phe Val Glu Lys Cys Cys Lys Ala Asp Asp Lys Glu Thr Cys Phe
625                 630                 635                 640
Ala Glu Glu Gly Lys Lys Leu Val Ala Ala Ser Gln Ala Ala Leu Gly
                645                 650                 655
Leu

<210> SEQ ID NO 41
<211> LENGTH: 657
<212> TYPE: PRT
<213> ORGANISM: Artificial Sequence
<220> FEATURE:
<223> OTHER INFORMATION: fusion protein

<400> SEQUENCE: 41

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
```

-continued

```
            195                 200                 205
Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
                275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
                355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                    565                 570                 575

Ala Ala Ser Gln Ala Ala Leu Gly Leu Pro Ala Pro Ala Pro Ala Asn
                580                 585                 590

His Lys Gly Arg Gly Arg Pro Ala Lys Cys Lys Leu Pro Pro Asp Asp
                595                 600                 605

Gly Pro Cys Arg Ala Arg Ile Pro Ser Tyr Tyr Phe Asp Arg Lys Thr
                610                 615                 620
```

```
Lys Thr Cys Lys Glu Phe Met Tyr Gly Gly Cys Glu Gly Asn Glu Asn
625                 630                 635                 640

Asn Phe Glu Gln Ile Thr Thr Cys Gln Glu Cys Arg Ala Lys Lys
            645                 650                 655

Val

<210> SEQ ID NO 42
<211> LENGTH: 668
<212> TYPE: PRT
<213> ORGANISM: Artificial Sequence
<220> FEATURE:
<223> OTHER INFORMATION: fusion protein

<400> SEQUENCE: 42

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
                35                  40                  45

Glu Asn Asn Phe Glu Gln Ile Thr Thr Cys Gln Glu Cys Arg Ala
50                  55                  60

Lys Lys Val Gly Gly Gly Ser Gly Gly Gly Ser Gly Gly Gly
65                  70                  75                  80

Gly Ser Ala Asp Ala His Lys Ser Glu Val Ala His Arg Phe Lys Asp
                85                  90                  95

Leu Gly Glu Glu Asn Phe Lys Ala Leu Val Leu Ile Ala Phe Ala Gln
                100                 105                 110

Tyr Leu Gln Gln Cys Pro Phe Glu Asp His Val Lys Leu Val Asn Glu
            115                 120                 125

Val Thr Glu Phe Ala Lys Thr Cys Val Ala Asp Glu Ser Ala Glu Asn
130                 135                 140

Cys Asp Lys Ser Leu His Thr Leu Phe Gly Asp Lys Leu Cys Thr Val
145                 150                 155                 160

Ala Thr Leu Arg Glu Thr Tyr Gly Glu Met Ala Asp Cys Cys Ala Lys
                165                 170                 175

Gln Glu Pro Glu Arg Asn Glu Cys Phe Leu Gln His Lys Asp Asp Asn
            180                 185                 190

Pro Asn Leu Pro Arg Leu Val Arg Pro Glu Val Asp Val Met Cys Thr
            195                 200                 205

Ala Phe His Asp Asn Glu Glu Thr Phe Leu Lys Lys Tyr Leu Tyr Glu
210                 215                 220

Ile Ala Arg Arg His Pro Tyr Phe Tyr Ala Pro Glu Leu Leu Phe Phe
225                 230                 235                 240

Ala Lys Arg Tyr Lys Ala Ala Phe Thr Glu Cys Cys Gln Ala Ala Asp
                245                 250                 255

Lys Ala Ala Cys Leu Leu Pro Lys Leu Asp Glu Leu Arg Asp Glu Gly
            260                 265                 270

Lys Ala Ser Ser Ala Lys Gln Arg Leu Lys Cys Ala Ser Leu Gln Lys
            275                 280                 285

Phe Gly Glu Arg Ala Phe Lys Ala Trp Ala Val Ala Arg Leu Ser Gln
            290                 295                 300

Arg Phe Pro Lys Ala Glu Phe Ala Glu Val Ser Lys Leu Val Thr Asp
305                 310                 315                 320
```

Leu Thr Lys Val His Thr Glu Cys Cys His Gly Asp Leu Leu Glu Cys
                325                 330                 335

Ala Asp Asp Arg Ala Asp Leu Ala Lys Tyr Ile Cys Glu Asn Gln Asp
            340                 345                 350

Ser Ile Ser Ser Lys Leu Lys Glu Cys Cys Glu Lys Pro Leu Leu Glu
        355                 360                 365

Lys Ser His Cys Ile Ala Glu Val Glu Asn Asp Glu Met Pro Ala Asp
    370                 375                 380

Leu Pro Ser Leu Ala Ala Asp Phe Val Glu Ser Lys Asp Val Cys Lys
385                 390                 395                 400

Asn Tyr Ala Glu Ala Lys Asp Val Phe Leu Gly Met Phe Leu Tyr Glu
                405                 410                 415

Tyr Ala Arg Arg His Pro Asp Tyr Ser Val Val Leu Leu Leu Arg Leu
            420                 425                 430

Ala Lys Thr Tyr Glu Thr Thr Leu Glu Lys Cys Cys Ala Ala Ala Asp
        435                 440                 445

Pro His Glu Cys Tyr Ala Lys Val Phe Asp Glu Phe Lys Pro Leu Val
    450                 455                 460

Glu Glu Pro Gln Asn Leu Ile Lys Gln Asn Cys Glu Leu Phe Glu Gln
465                 470                 475                 480

Leu Gly Glu Tyr Lys Phe Gln Asn Ala Leu Leu Val Arg Tyr Thr Lys
                485                 490                 495

Lys Val Pro Gln Val Ser Thr Pro Thr Leu Val Glu Val Ser Arg Asn
            500                 505                 510

Leu Gly Lys Val Gly Ser Lys Cys Cys Lys His Pro Glu Ala Lys Arg
        515                 520                 525

Met Pro Cys Ala Glu Asp Tyr Leu Ser Val Val Leu Asn Gln Leu Cys
    530                 535                 540

Val Leu His Glu Lys Thr Pro Val Ser Asp Arg Val Thr Lys Cys Cys
545                 550                 555                 560

Thr Glu Ser Leu Val Asn Arg Arg Pro Cys Phe Ser Ala Leu Glu Val
                565                 570                 575

Asp Glu Thr Tyr Val Pro Lys Glu Phe Asn Ala Glu Thr Phe Thr Phe
            580                 585                 590

His Ala Asp Ile Cys Thr Leu Ser Glu Lys Glu Arg Gln Ile Lys Lys
        595                 600                 605

Gln Thr Ala Leu Val Glu Leu Val Lys His Lys Pro Lys Ala Thr Lys
    610                 615                 620

Glu Gln Leu Lys Ala Val Met Asp Asp Phe Ala Ala Phe Val Glu Lys
625                 630                 635                 640

Cys Cys Lys Ala Asp Asp Lys Glu Thr Cys Phe Ala Glu Glu Gly Lys
                645                 650                 655

Lys Leu Val Ala Ala Ser Gln Ala Ala Leu Gly Leu
            660                 665

<210> SEQ ID NO 43
<211> LENGTH: 668
<212> TYPE: PRT
<213> ORGANISM: Artificial Sequence
<220> FEATURE:
<223> OTHER INFORMATION: fusion protein

<400> SEQUENCE: 43

Asp Ala His Lys Ser Glu Val Ala His Arg Phe Lys Asp Leu Gly Glu
1               5                   10                  15

-continued

```
Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
```

-continued

```
                435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                    485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gly Gly Gly Ser Gly Gly
                580                 585                 590
Gly Gly Ser Gly Gly Gly Gly Ser Ala Ala Asn His Lys Gly Arg Gly
            595                 600                 605
Arg Pro Ala Lys Cys Lys Leu Pro Pro Asp Gly Pro Cys Arg Ala
610                 615                 620
Arg Ile Pro Ser Tyr Tyr Phe Asp Arg Lys Thr Lys Thr Cys Lys Glu
625                 630                 635                 640
Phe Met Tyr Gly Gly Cys Gly Gly Asn Glu Asn Asn Phe Glu Gln Ile
                    645                 650                 655
Thr Thr Cys Gln Glu Glu Cys Arg Ala Lys Lys Val
            660                 665
```

<210> SEQ ID NO 44
<211> LENGTH: 683
<212> TYPE: PRT
<213> ORGANISM: Artificial Sequence
<220> FEATURE:
<223> OTHER INFORMATION: fusion protein

<400> SEQUENCE: 44

```
Ala Asn His Lys Gly Arg Gly Arg Pro Ala Lys Cys Lys Leu Pro Pro
1               5                   10                  15
Asp Asp Gly Pro Cys Arg Ala Arg Ile Pro Ser Tyr Tyr Phe Asp Arg
                20                  25                  30
Lys Thr Lys Thr Cys Lys Glu Phe Met Tyr Gly Gly Cys Glu Gly Asn
            35                  40                  45
Glu Asn Asn Phe Glu Gln Ile Thr Thr Cys Gln Glu Glu Cys Arg Ala
50                  55                  60
Lys Lys Val Gly Ser Gly Gly Ser Gly Gly Ser Gly Gly Ser Gly Gly
65                  70                  75                  80
Ser Gly Gly Ser Gly Gly Ser Gly Gly Ser Gly Gly Ser Gly Gly Ser
                85                  90                  95
Gly Ser Asp Ala His Lys Ser Glu Val Ala His Arg Phe Lys Asp Leu
                100                 105                 110
Gly Glu Glu Asn Phe Lys Ala Leu Val Leu Ile Ala Phe Ala Gln Tyr
            115                 120                 125
Leu Gln Gln Cys Pro Phe Glu Asp His Val Lys Leu Val Asn Glu Val
```

```
            130                 135                 140
Thr Glu Phe Ala Lys Thr Cys Val Ala Asp Glu Ser Ala Glu Asn Cys
145                 150                 155                 160

Asp Lys Ser Leu His Thr Leu Phe Gly Asp Lys Leu Cys Thr Val Ala
                165                 170                 175

Thr Leu Arg Glu Thr Tyr Gly Glu Met Ala Asp Cys Cys Ala Lys Gln
            180                 185                 190

Glu Pro Glu Arg Asn Glu Cys Phe Leu Gln His Lys Asp Asp Asn Pro
                195                 200                 205

Asn Leu Pro Arg Leu Val Arg Pro Glu Val Asp Val Met Cys Thr Ala
210                 215                 220

Phe His Asp Asn Glu Glu Thr Phe Leu Lys Lys Tyr Leu Tyr Glu Ile
225                 230                 235                 240

Ala Arg Arg His Pro Tyr Phe Tyr Ala Pro Glu Leu Leu Phe Phe Ala
                245                 250                 255

Lys Arg Tyr Lys Ala Ala Phe Thr Glu Cys Cys Gln Ala Ala Asp Lys
                260                 265                 270

Ala Ala Cys Leu Leu Pro Lys Leu Asp Glu Leu Arg Asp Glu Gly Lys
                275                 280                 285

Ala Ser Ser Ala Lys Gln Arg Leu Lys Cys Ala Ser Leu Gln Lys Phe
                290                 295                 300

Gly Glu Arg Ala Phe Lys Ala Trp Ala Val Ala Arg Leu Ser Gln Arg
305                 310                 315                 320

Phe Pro Lys Ala Glu Phe Ala Glu Val Ser Lys Leu Val Thr Asp Leu
                325                 330                 335

Thr Lys Val His Thr Glu Cys Cys His Gly Asp Leu Leu Glu Cys Ala
                340                 345                 350

Asp Asp Arg Ala Asp Leu Ala Lys Tyr Ile Cys Glu Asn Gln Asp Ser
                355                 360                 365

Ile Ser Ser Lys Leu Lys Glu Cys Cys Glu Lys Pro Leu Leu Glu Lys
                370                 375                 380

Ser His Cys Ile Ala Glu Val Glu Asn Asp Glu Met Pro Ala Asp Leu
385                 390                 395                 400

Pro Ser Leu Ala Ala Asp Phe Val Glu Ser Lys Asp Val Cys Lys Asn
                405                 410                 415

Tyr Ala Glu Ala Lys Asp Val Phe Leu Gly Met Phe Leu Tyr Glu Tyr
                420                 425                 430

Ala Arg Arg His Pro Asp Tyr Ser Val Val Leu Leu Leu Arg Leu Ala
                435                 440                 445

Lys Thr Tyr Glu Thr Thr Leu Glu Lys Cys Cys Ala Ala Ala Asp Pro
                450                 455                 460

His Glu Cys Tyr Ala Lys Val Phe Asp Glu Phe Lys Pro Leu Val Glu
465                 470                 475                 480

Glu Pro Gln Asn Leu Ile Lys Gln Asn Cys Glu Leu Phe Glu Gln Leu
                485                 490                 495

Gly Glu Tyr Lys Phe Gln Asn Ala Leu Leu Val Arg Tyr Thr Lys Lys
                500                 505                 510

Val Pro Gln Val Ser Thr Pro Thr Leu Val Glu Val Ser Arg Asn Leu
                515                 520                 525

Gly Lys Val Gly Ser Lys Cys Cys Lys His Pro Glu Ala Lys Arg Met
                530                 535                 540

Pro Cys Ala Glu Asp Tyr Leu Ser Val Val Leu Asn Gln Leu Cys Val
545                 550                 555                 560
```

```
Leu His Glu Lys Thr Pro Val Ser Asp Arg Val Thr Lys Cys Cys Thr
                565                 570                 575
Glu Ser Leu Val Asn Arg Arg Pro Cys Phe Ser Ala Leu Glu Val Asp
                580                 585                 590
Glu Thr Tyr Val Pro Lys Glu Phe Asn Ala Glu Thr Phe Thr Phe His
                595                 600                 605
Ala Asp Ile Cys Thr Leu Ser Glu Lys Glu Arg Gln Ile Lys Lys Gln
            610                 615                 620
Thr Ala Leu Val Glu Leu Val Lys His Lys Pro Lys Ala Thr Lys Glu
625                 630                 635                 640
Gln Leu Lys Ala Val Met Asp Asp Phe Ala Ala Phe Val Glu Lys Cys
                645                 650                 655
Cys Lys Ala Asp Asp Lys Glu Thr Cys Phe Ala Glu Glu Gly Lys Lys
                660                 665                 670
Leu Val Ala Ala Ser Gln Ala Ala Leu Gly Leu
                675                 680

<210> SEQ ID NO 45
<211> LENGTH: 683
<212> TYPE: PRT
<213> ORGANISM: Artificial Sequence
<220> FEATURE:
<223> OTHER INFORMATION: fusion protein

<400> SEQUENCE: 45

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
            35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
```

```
Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Ser Gly Gly Ser Gly Gly
            580                 585                 590

Ser Gly Gly Ser Gly Gly Ser Gly Gly Ser Gly Gly Ser Gly Gly Ser
        595                 600                 605

Gly Gly Ser Gly Gly Ser Gly Ser Ala Asn His Lys Gly Arg Gly Arg
    610                 615                 620

Pro Ala Lys Cys Lys Leu Pro Pro Asp Asp Gly Pro Cys Arg Ala Arg
625                 630                 635                 640

Ile Pro Ser Tyr Tyr Phe Asp Arg Lys Thr Lys Thr Cys Lys Glu Phe
                645                 650                 655
```

```
Met Tyr Gly Gly Cys Glu Gly Asn Glu Asn Asn Phe Glu Gln Ile Thr
            660                 665                 670

Thr Cys Gln Glu Glu Cys Arg Ala Lys Lys Val
            675                 680

<210> SEQ ID NO 46
<211> LENGTH: 761
<212> TYPE: PRT
<213> ORGANISM: Artificial Sequence
<220> FEATURE:
<223> OTHER INFORMATION: fusion protein

<400> SEQUENCE: 46

Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Glu Cys Arg Ala
    50                  55                  60

Lys Lys Val Ala Pro Ala Pro Ala Pro Ala Pro Ala Pro Ala Pro Ala
65                  70                  75                  80

Pro Ala Asn His Lys Gly Arg Gly Arg Pro Ala Lys Cys Lys Leu Pro
                85                  90                  95

Pro Asp Asp Gly Pro Cys Arg Ala Arg Ile Pro Ser Tyr Tyr Phe Asp
            100                 105                 110

Arg Lys Thr Lys Thr Cys Lys Glu Phe Met Tyr Gly Gly Cys Glu Gly
        115                 120                 125

Asn Glu Asn Asn Phe Glu Gln Ile Thr Thr Cys Gln Glu Glu Cys Arg
    130                 135                 140

Ala Lys Lys Val Ala Pro Ala Pro Ala Pro Ala Pro Ala Pro Ala Pro
145                 150                 155                 160

Ala Pro Ala Pro Ala Pro Ala Pro Ala Pro Ala Pro Ala Pro Ala Pro
                165                 170                 175

Asp Ala His Lys Ser Glu Val Ala His Arg Phe Lys Asp Leu Gly Glu
            180                 185                 190

Glu Asn Phe Lys Ala Leu Val Leu Ile Ala Phe Ala Gln Tyr Leu Gln
        195                 200                 205

Gln Cys Pro Phe Glu Asp His Val Lys Leu Val Asn Glu Val Thr Glu
    210                 215                 220

Phe Ala Lys Thr Cys Val Ala Asp Glu Ser Ala Glu Asn Cys Asp Lys
225                 230                 235                 240

Ser Leu His Thr Leu Phe Gly Asp Lys Leu Cys Thr Val Ala Thr Leu
                245                 250                 255

Arg Glu Thr Tyr Gly Glu Met Ala Asp Cys Cys Ala Lys Gln Glu Pro
            260                 265                 270

Glu Arg Asn Glu Cys Phe Leu Gln His Lys Asp Asp Asn Pro Asn Leu
        275                 280                 285

Pro Arg Leu Val Arg Pro Glu Val Asp Val Met Cys Thr Ala Phe His
    290                 295                 300

Asp Asn Glu Glu Thr Phe Leu Lys Lys Tyr Leu Tyr Glu Ile Ala Arg
305                 310                 315                 320

Arg His Pro Tyr Phe Tyr Ala Pro Glu Leu Leu Phe Phe Ala Lys Arg
                325                 330                 335
```

```
Tyr Lys Ala Ala Phe Thr Glu Cys Cys Gln Ala Ala Asp Lys Ala Ala
                340                 345                 350

Cys Leu Leu Pro Lys Leu Asp Glu Leu Arg Asp Glu Gly Lys Ala Ser
        355                 360                 365

Ser Ala Lys Gln Arg Leu Lys Cys Ala Ser Leu Gln Lys Phe Gly Glu
    370                 375                 380

Arg Ala Phe Lys Ala Trp Ala Val Ala Arg Leu Ser Gln Arg Phe Pro
385                 390                 395                 400

Lys Ala Glu Phe Ala Glu Val Ser Lys Leu Val Thr Asp Leu Thr Lys
                405                 410                 415

Val His Thr Glu Cys Cys His Gly Asp Leu Leu Glu Cys Ala Asp Asp
        420                 425                 430

Arg Ala Asp Leu Ala Lys Tyr Ile Cys Glu Asn Gln Asp Ser Ile Ser
    435                 440                 445

Ser Lys Leu Lys Glu Cys Cys Glu Lys Pro Leu Leu Glu Lys Ser His
    450                 455                 460

Cys Ile Ala Glu Val Glu Asn Asp Glu Met Pro Ala Asp Leu Pro Ser
465                 470                 475                 480

Leu Ala Ala Asp Phe Val Glu Ser Lys Asp Val Cys Lys Asn Tyr Ala
                485                 490                 495

Glu Ala Lys Asp Val Phe Leu Gly Met Phe Leu Tyr Glu Tyr Ala Arg
                500                 505                 510

Arg His Pro Asp Tyr Ser Val Val Leu Leu Leu Arg Leu Ala Lys Thr
        515                 520                 525

Tyr Glu Thr Thr Leu Glu Lys Cys Cys Ala Ala Ala Asp Pro His Glu
    530                 535                 540

Cys Tyr Ala Lys Val Phe Asp Glu Phe Lys Pro Leu Val Glu Glu Pro
545                 550                 555                 560

Gln Asn Leu Ile Lys Gln Asn Cys Glu Leu Phe Glu Gln Leu Gly Glu
                565                 570                 575

Tyr Lys Phe Gln Asn Ala Leu Leu Val Arg Tyr Thr Lys Lys Val Pro
                580                 585                 590

Gln Val Ser Thr Pro Thr Leu Val Glu Val Ser Arg Asn Leu Gly Lys
        595                 600                 605

Val Gly Ser Lys Cys Cys Lys His Pro Glu Ala Lys Arg Met Pro Cys
    610                 615                 620

Ala Glu Asp Tyr Leu Ser Val Val Leu Asn Gln Leu Cys Val Leu His
625                 630                 635                 640

Glu Lys Thr Pro Val Ser Asp Arg Val Thr Lys Cys Cys Thr Glu Ser
                645                 650                 655

Leu Val Asn Arg Arg Pro Cys Phe Ser Ala Leu Glu Val Asp Glu Thr
                660                 665                 670

Tyr Val Pro Lys Glu Phe Asn Ala Glu Thr Phe Thr Phe His Ala Asp
        675                 680                 685

Ile Cys Thr Leu Ser Glu Lys Glu Arg Gln Ile Lys Lys Gln Thr Ala
    690                 695                 700

Leu Val Glu Leu Val Lys His Lys Pro Lys Ala Thr Lys Glu Gln Leu
705                 710                 715                 720

Lys Ala Val Met Asp Asp Phe Ala Ala Phe Val Glu Lys Cys Cys Lys
                725                 730                 735

Ala Asp Asp Lys Glu Thr Cys Phe Ala Glu Glu Gly Lys Lys Leu Val
                740                 745                 750

Ala Ala Ser Gln Ala Ala Leu Gly Leu
```

-continued

```
            755                 760
```

<210> SEQ ID NO 47
<211> LENGTH: 658
<212> TYPE: PRT
<213> ORGANISM: Artificial Sequence
<220> FEATURE:
<223> OTHER INFORMATION: fusion protein

<400> SEQUENCE: 47

```
Ala Asn His Lys Gly Arg Gly Arg Pro Ala Lys Cys Lys Leu Pro Pro
1               5                   10                  15

Asp Asp Gly Pro Cys Arg Ala Arg Ile Pro Ser Tyr Tyr Phe Asp Arg
            20                  25                  30

Lys Thr Lys Thr Cys Lys Glu Phe Met Tyr Gly Gly Cys Glu Gly Asn
        35                  40                  45

Glu Asn Asn Phe Glu Gln Ile Thr Thr Cys Gln Glu Cys Arg Ala
    50                  55                  60

Lys Lys Val Gly Gly Gly Ser Ala Asp Ala His Lys Ser Glu Val
65                  70                  75                  80

Ala His Arg Phe Lys Asp Leu Gly Glu Glu Asn Phe Lys Ala Leu Val
                85                  90                  95

Leu Ile Ala Phe Ala Gln Tyr Leu Gln Gln Cys Pro Phe Glu Asp His
            100                 105                 110

Val Lys Leu Val Asn Glu Val Thr Glu Phe Ala Lys Thr Cys Val Ala
        115                 120                 125

Asp Glu Ser Ala Glu Asn Cys Asp Lys Ser Leu His Thr Leu Phe Gly
    130                 135                 140

Asp Lys Leu Cys Thr Val Ala Thr Leu Arg Glu Thr Tyr Gly Glu Met
145                 150                 155                 160

Ala Asp Cys Cys Ala Lys Gln Glu Pro Glu Arg Asn Glu Cys Phe Leu
                165                 170                 175

Gln His Lys Asp Asp Asn Pro Asn Leu Pro Arg Leu Val Arg Pro Glu
            180                 185                 190

Val Asp Val Met Cys Thr Ala Phe His Asp Asn Glu Glu Thr Phe Leu
        195                 200                 205

Lys Lys Tyr Leu Tyr Glu Ile Ala Arg Arg His Pro Tyr Phe Tyr Ala
    210                 215                 220

Pro Glu Leu Leu Phe Phe Ala Lys Arg Tyr Lys Ala Ala Phe Thr Glu
225                 230                 235                 240

Cys Cys Gln Ala Ala Asp Lys Ala Ala Cys Leu Leu Pro Lys Leu Asp
                245                 250                 255

Glu Leu Arg Asp Glu Gly Lys Ala Ser Ser Ala Lys Gln Arg Leu Lys
            260                 265                 270

Cys Ala Ser Leu Gln Lys Phe Gly Glu Arg Ala Phe Lys Ala Trp Ala
        275                 280                 285

Val Ala Arg Leu Ser Gln Arg Phe Pro Lys Ala Glu Phe Ala Glu Val
    290                 295                 300

Ser Lys Leu Val Thr Asp Leu Thr Lys Val His Thr Glu Cys Cys His
305                 310                 315                 320

Gly Asp Leu Leu Glu Cys Ala Asp Asp Arg Ala Asp Leu Ala Lys Tyr
                325                 330                 335

Ile Cys Glu Asn Gln Asp Ser Ile Ser Ser Lys Leu Lys Glu Cys Cys
            340                 345                 350

Glu Lys Pro Leu Leu Glu Lys Ser His Cys Ile Ala Glu Val Glu Asn
```

```
              355                 360                 365
Asp Glu Met Pro Ala Asp Leu Pro Ser Leu Ala Ala Asp Phe Val Glu
    370                 375                 380

Ser Lys Asp Val Cys Lys Asn Tyr Ala Glu Ala Lys Asp Val Phe Leu
385                 390                 395                 400

Gly Met Phe Leu Tyr Glu Tyr Ala Arg Arg His Pro Asp Tyr Ser Val
                405                 410                 415

Val Leu Leu Leu Arg Leu Ala Lys Thr Tyr Glu Thr Thr Leu Glu Lys
            420                 425                 430

Cys Cys Ala Ala Ala Asp Pro His Glu Cys Tyr Ala Lys Val Phe Asp
            435                 440                 445

Glu Phe Lys Pro Leu Val Glu Glu Pro Gln Asn Leu Ile Lys Gln Asn
            450                 455                 460

Cys Glu Leu Phe Glu Gln Leu Gly Glu Tyr Lys Phe Gln Asn Ala Leu
465                 470                 475                 480

Leu Val Arg Tyr Thr Lys Lys Val Pro Gln Val Ser Thr Pro Thr Leu
                485                 490                 495

Val Glu Val Ser Arg Asn Leu Gly Lys Val Gly Ser Lys Cys Cys Lys
            500                 505                 510

His Pro Glu Ala Lys Arg Met Pro Cys Ala Glu Asp Tyr Leu Ser Val
            515                 520                 525

Val Leu Asn Gln Leu Cys Val Leu His Glu Lys Thr Pro Val Ser Asp
            530                 535                 540

Arg Val Thr Lys Cys Cys Thr Glu Ser Leu Val Asn Arg Arg Pro Cys
545                 550                 555                 560

Phe Ser Ala Leu Glu Val Asp Glu Thr Tyr Val Pro Lys Glu Phe Asn
                565                 570                 575

Ala Glu Thr Phe Thr Phe His Ala Asp Ile Cys Thr Leu Ser Glu Lys
            580                 585                 590

Glu Arg Gln Ile Lys Lys Gln Thr Ala Leu Val Glu Leu Val Lys His
            595                 600                 605

Lys Pro Lys Ala Thr Lys Glu Gln Leu Lys Ala Val Met Asp Asp Phe
610                 615                 620

Ala Ala Phe Val Glu Lys Cys Cys Lys Ala Asp Asp Lys Glu Thr Cys
625                 630                 635                 640

Phe Ala Glu Glu Gly Lys Lys Leu Val Ala Ala Ser Gln Ala Ala Leu
                645                 650                 655

Gly Leu

<210> SEQ ID NO 48
<211> LENGTH: 658
<212> TYPE: PRT
<213> ORGANISM: Artificial Sequence
<220> FEATURE:
<223> OTHER INFORMATION: fusion protein

<400> SEQUENCE: 48

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60
```

```
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480
```

```
Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Ala Ala
            580                 585                 590

Asn His Lys Gly Arg Gly Arg Pro Ala Lys Cys Lys Leu Pro Pro Asp
            595                 600                 605

Asp Gly Pro Cys Arg Ala Arg Ile Pro Ser Tyr Tyr Phe Asp Arg Lys
        610                 615                 620

Thr Lys Thr Cys Lys Glu Phe Met Tyr Gly Gly Cys Glu Gly Asn Glu
625                 630                 635                 640

Asn Asn Phe Glu Gln Ile Thr Thr Cys Gln Glu Cys Arg Ala Lys
                645                 650                 655

Lys Val

<210> SEQ ID NO 49
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: 3..4
<223> OTHER INFORMATION: n wherein n is a number from 1 to 20

<400> SEQUENCE: 49

Ala Pro Ala Pro
1

<210> SEQ ID NO 50
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: 1
<223> OTHER INFORMATION: n wherein n is a number from 1 to 7

<400> SEQUENCE: 50

Gly Gly Gly Ser
1

<210> SEQ ID NO 51
<211> LENGTH: 4
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: 1
```

```
<223> OTHER INFORMATION: n wherein n is a number from 1 to 10
<220> FEATURE:
<221> NAME/KEY: REPEAT
<222> LOCATION: 3
<223> OTHER INFORMATION: n wherein n is a number from 1 to 10, similar
      to the number of repeat in position 1
<220> FEATURE:
<221> NAME/KEY: REPEAT
<222> LOCATION: 3..4
<223> OTHER INFORMATION: m wherein m is a number from 1 to 10

<400> SEQUENCE: 51

Gly Ser Gly Ser
1

<210> SEQ ID NO 52
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: 1
<223> OTHER INFORMATION: n wherein n is a number from 1 to 10
<220> FEATURE:
<221> NAME/KEY: REPEAT
<222> LOCATION: 3
<223> OTHER INFORMATION: n wherein n is a number from 1 to 10, similar
      to the number of repeat in postion 1
<220> FEATURE:
<221> NAME/KEY: REPEAT
<222> LOCATION: 3..4
<223> OTHER INFORMATION: m wherein m is a number from 1 to 10

<400> SEQUENCE: 52

Gly Ser Gly Ser Ala
1               5
```

ANTICOAGULANT FUSION PROTEINS AND USES THEREOF

CROSS-REFERENCE TO RELATED APPLICATIONS

This application is the U.S. national phase of International Application No. PCT/EP2019/057914 filed Mar. 28, 2019 which designated the U.S. and claims priority to European Application No. 18164570.6 filed Mar. 28, 2018, the entire contents of each of which are hereby incorporated by reference.

FIELD OF INVENTION

The present invention relates to anticoagulant fusion proteins and their use for treating or preventing thrombus formation and/or thrombus growth, cardiovascular diseases, neurological diseases, cancer and metastasis. In particular, the present invention relates to anticoagulant fusion proteins comprising an *Ixodes ricinus* salivary gland polypeptide.

BACKGROUND OF INVENTION

Hemostasis is a vital function that stops bleeding and protects the integrity of blood circulation on both molecular and macroscopic levels. Hemostasis includes a coagulation cascade traditionally divided into two converting enzymatic cascades that are triggered either by exposure of blood to a damaged vessel wall (the extrinsic pathway) or by blood-borne components of the vascular system (the intrinsic pathway).

The extrinsic coagulation pathway is triggered by the binding of tissue factor produced by exposed subendothelial cells to plasma factor VII. The resulting complex initiates the coagulation cascade, activates factor X to factor Xa which ultimately leads to thrombin generation. Thrombin activates platelets and converts fibrinogen into fibrin. Both platelets and fibrin are essential elements of the hemostatic plug that is responsible for sealing the vascular breach.

The intrinsic pathway is initiated by contact phase proteins including the zymogens factor XII, factor XI and prekallikrein, as well as the cofactor high molecular weight kininogen (HK). Factor XII undergoes autoactivation when bound to negatively charged surfaces, generating activated factor XII by a conformation change. Activated factor XII then converts prekallikrein into kallikrein. Once small amounts of kallikrein are formed, they catalyze the conversion of surface-bound factor XII into factor XIIa leading to strong positive feedback on the system. During this process, the activation of factor XII leads to a succession of proteolysis steps leading to the production of a series of different active enzymes (XIa, IXa, VIIIa, Xa) which ultimately leads to activation of pro-thrombin in thrombin and formation of fibrin.

The intrinsic and extrinsic coagulation pathways may interact each with the other. The activation of factor VII occurs through the action of thrombin or factor Xa. An additional link between the two pathways exists through the ability of tissue factor and factor VIIa to activate factor IX. Furthermore, thrombin can activate factor XI into factor XIa creating a positive feedback loop of amplification of the intrinsic pathway to sustain coagulation.

Current anticoagulant drugs inhibit factors from the extrinsic pathway of coagulation: heparin (via antithrombin III) inhibits thrombin, factors Xa and IXa, antivitamins K inhibit the synthesis of prothrombin, factors VII, IX and X, whereas Low Molecular Weight Heparin (LMWH) mainly inhibits factor Xa. The therapeutic window of these drugs is narrow, requiring careful monitoring of patients. Moreover, these drugs are linked to a risk of hemorrhage. Thus, the search for new anticoagulants preventing thrombus formation without increasing hemorrhage risk is a major challenge in medicine.

The discovery that FXI and FXII deficiency protects against thrombosis without causing spontaneous bleeding in mice makes them unique and ideal targets for drug design. FXII−/− deficient mice are protected from experimental cerebral ischemia and pulmonary embolism. Moreover, it was shown that FXII-deficient (partial or severe) patients and animals do not exhibit a clinically relevant bleeding phenotype. However, human congenital FXI deficiency is generally accompanied by mild injury-related bleeding. In these patients, spontaneous bleedings are rare and bleeding typically occurs after surgery or injury and particularly affects tissues with high fibrinolytic activity (oral and nasal cavities, tonsils, genitourinary tract). In contrast to its mild hemostatic activities, FXI is known to play a significant role in thrombosis and has been demonstrated to be an independent risk factor for deep vein thrombosis, ischemic stroke, and myocardial infarction.

The Applicant already shows that a polypeptide of the salivary gland of *Ixodes ricinus* (IrCPI) simultaneously inhibits Factor XI and Factor XII (U.S. Ser. No. 14/883,217) (Decrem et al., 2009). Moreover, the Applicant has found that IrCPI inhibits platelet recruitment, neutrophil recruitment, neutrophil activation and neutrophil extracellular trap formation (NETosis) after activation of the extrinsic pathway of the coagulation (PCT/EP2019/052542).

Here, the Applicant shows fusion proteins comprising such *Ixodes ricinus* salivary gland polypeptide with improved blood circulatory half-life.

Examples of IrCPI-base fusion-proteins exist in the state-of-the-art, e.g. US 2013/0129741, WO 2009/141382, Leboulle et al. (2002), which disclose the fusion of IrCPI with a marker sequence, such as 6His peptide, HA tag, GST, MBP, in order to facilitate the purification of the fused polypeptide after synthesis using a recombinant method. This marker sequence is cleaved and released from the final IrCPI product after the affinity purification process to obtain a pure recombinant protein.

In another example of IrCPI-based fusion-protein, IrCPI was fused to serum albumin to generate antibodies against the protein of interest (WO 00/77198).

However, none of these state-of-the-art documents reported that the resulting fusion protein would achieve improvement of the circulatory half-life compared to an unfused IrCPI polypeptide.

The present invention thus relates to anticoagulant fusion proteins and their use for preventing or treating thrombus formation and/or growth, cardiovascular diseases, neurological diseases, cancer and metastasis.

SUMMARY

The present invention relates to a fusion protein comprising at least one *Ixodes ricinus* salivary gland (IrCPI) polypeptide, wherein the fusion protein has an increased circulatory half-life compared to an unfused IrCPI polypeptide. In one embodiment, said IrCPI polypeptide has an amino sequence at least 75% identical to SEQ ID NO: 1.

In one embodiment, the fusion protein as described hereinabove comprises at least one IrCPI polypeptide and at least one other polypeptide selected from the group comprising albumin, linear or branched-chain monomethoxy poly-ethylene glycol (PEG), hyaluronic acid, Fc domain of IgG, human IgG, transferrin, homo-amino acid polymer (HAP), proline-alanine-serine polymer (PAS), elastin-like peptide (ELP), negatively charged highly sialylated peptide and hybrid repetitive motif (HRM). In one embodiment, said at least one other polypeptide is a serum albumin polypeptide, preferably a human serum albumin polypeptide. In one embodiment, said serum albumin polypeptide has an amino sequence comprising the sequence of SEQ ID NO: 3.

In one embodiment, the fusion protein as described hereinabove further comprises at least one peptide linker. In one embodiment, the fusion protein as described hereinabove further comprises at least one peptide linker selected from the group comprising Gly-rich linkers, Ser-rich linkers, Gly-rich and Ser-rich linkers, Pro-rich linkers, helical linkers, linkers cleavable by a protease and a combination thereof.

In one embodiment, the Gly-rich and Ser-rich linker is selected from the group comprising $(G_nS)_m$ linker wherein "n" is a number from 1 to 10, preferably from 2 to 7, more preferably from 3 to 5 and wherein "m" is a number from 1 to 10, preferably from 2 to 7, more preferably from 3 to 5; $(G_nS)_mA$ linker, wherein "n" is a number from 1 to 10, preferably from 2 to 7, more preferably from 3 to 5 and wherein "m" is a number from 1 to 10, preferably from 2 to 7, more preferably from 3 to 5; and a $GS(GGS)_nGS$ linker wherein "n" is a number from 1 to 20.

In one embodiment, the Pro-rich linker is selected from the group comprising $(AP)_n$ and $P(AP)_n$ linker; wherein "n" is a number from 1 to 20. In one embodiment, said at least one peptide linker has the amino acid sequence $(AP)_n$, wherein "n" is a number from 1 to 20. In one embodiment, the peptide linker has the amino acid sequence $(AP)_7$. In one embodiment, the peptide linker has the amino acid sequence $(AP)_{14}$.

In one embodiment, the helical linker is selected from the group comprising $(EAAAK)_n$ linker, wherein "n" is a number from 1 to 10 (SEQ ID NO: 14); $[A(EAAAK)_nA]_m$, wherein "n" is a number from 2 to 10 and "m" is a number from 1 to 5 (SEQ ID NO: 15); and $A(EAAAK)_nALEA(EAAAK)_mA$ wherein "n" is a number from 1 to 10 and "m" is a number from 1 to 10 (SEQ ID NO: 22).

In one embodiment, the fusion protein is selected from the group of fusion proteins having an amino acid sequence comprising or consisting in the sequence of SEQ ID NO: 4, SEQ ID NO: 5, SEQ ID NO: 6, SEQ ID NO: 7, SEQ ID NO: 13, SEQ ID NO: 17, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 and SEQ ID NO: 48.

The present invention further relates to a fusion protein comprising (i) at least one *Ixodes ricinus* salivary gland (IrCPI) polypeptide, having an amino sequence at least 75% identical to SEQ ID NO: 1, (ii) at least one serum albumin polypeptide and (iii) at least one peptide linker, wherein the fusion protein has an increased circulatory half-life compared to an unfused IrCPI polypeptide.

Another object of the invention is a polynucleotide encoding a fusion protein as described hereinabove.

Another object of the invention is a vector comprising at least one polynucleotide as described hereinabove.

Another object of the invention is a composition comprising a fusion protein, a polynucleotide or a vector as described hereinabove.

Another object of the invention is a pharmaceutical composition comprising a fusion protein, a polynucleotide or a vector as described hereinabove and at least one pharmaceutically acceptable excipient.

Another object of the invention is a medicament comprising a fusion protein, a polynucleotide, a vector or a pharmaceutical composition as described hereinabove.

Still another object of the invention is a medical device coated with a fusion protein as described hereinabove.

The present invention also relates to a fusion protein, a pharmaceutical composition, a medicament or a medical device as described hereinabove for use for preventing thrombus formation and/or growth; for treating or preventing cardiovascular and/or neurological diseases; and for treating or preventing cancer and metastasis. The present invention also relates to a fusion protein, a pharmaceutical composition, a medicament or a medical device as described hereinabove for use for preventing thrombus formation and/or growth associated to or due to cardiovascular disease, neurological diseases, cancer and/or metastasis.

A further object of the invention is a fusion protein, a pharmaceutical composition, a medicament or a medical device as described hereinabove for inhibiting platelet recruitment, neutrophil recruitment, neutrophil activation and/or neutrophil extracellular trap formation (NETosis).

Another object of the invention is a kit comprising a fusion protein, a polynucleotide, a vector, a composition, a pharmaceutical composition, a medicament or a medical device as described hereinabove, and optionally means to administer the fusion protein, polynucleotide, vector, composition, pharmaceutical composition, medicament or medical device to a subject in need thereof.

Definitions

In the present invention, the following terms have the following meanings:

The term "about" preceding a value means plus or less 10% of said value.

The term "amino acid substitution" refers to the replacement in a polypeptide of one amino acid with another amino acid. In one embodiment, an amino acid is replaced with another amino acid having similar structural and/or chemical properties, e.g. conservative amino acid replacements. "Conservative amino acid substitution" may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic). Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful.

The term "identity" refers to a measure of the identity of nucleotide sequences or amino acid sequences. In general, the sequences are aligned so that the highest order match is obtained. "Identity" per se has an art-recognized meaning and can be calculated using published techniques. See, e.g.: Computational Molecular Biology, Lesk, A. M., ed., Oxford University Press, New York, 1988; Biocomputing: Informatics And Genome Projects, Smith, D. W., ed., Academic Press, New York, 1993; Computer Analysis Of Sequence Data, Part I, Griffin, A. M., and Griffin, H. G., eds, Humana Press, New Jersey, 1994; Sequence Analysis In Molecular Biology, von Heijne, G., Academic Press, 1987; and Sequence Analysis Primer, Gribskov, M. and Devereux, J., eds, M Stockton Press, New York, 1991. While there exist a number of methods to measure identity between two polynucleotide or polypeptide sequences, the term "identity" is well known to skilled artisans (Carillo and Lipton, SIAM J Applied Math, 1998, 48:1073). Methods commonly employed to determine identity or similarity between two sequences include, but are not limited to, those disclosed in Guide to Huge Computers, Martin J. Bishop, ed., Academic Press, San Diego, 1994; and Carillo and Lipton, SIAM J Applied Math, 1998, 48:1073. Methods to determine identity and similarity are codified in computer programs. Preferred computer program methods to determine identity and similarity between two sequences include, but are not limited to, GCG program package (Devereux et al., J Molec Biol, 1990, 215:403). Most preferably, the program used to determine identity levels was the GAP program, as was used in the Examples below.

As an illustration, by a polynucleotide having a nucleotide sequence having at least, for example, 95% "identity" to a reference nucleotide sequence is intended that the nucleotide sequence of the polynucleotide is identical to the reference sequence except that the polynucleotide sequence may include an average up to five-point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

The term "peptide linker" or "linker peptide", also called "spacer peptide", refers to a peptide used to link 2 peptides or polypeptides together. These terms are considered as being equivalent. In one embodiment, a peptide linker of the invention comprises from 3 to 50 amino acids. Peptide linkers are known in the art or are described herein. In one embodiment of the present invention, the peptide linker is also referred to as "L".

The term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like.

A pharmaceutically acceptable carrier or excipient refers to a non-toxic solid, semi-solid or liquid filler, diluent, encapsulating material or formulation auxiliary of any type. For human administration, preparations should meet sterility, pyrogenicity, general safety and purity standards as required by FDA Office of Biologics standards.

The term "polynucleotide" refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "Polynucleotide" refers to triple-stranded regions comprising RNA or DNA or both RNA and DNA. The term Polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "Polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

The term "polypeptide" refers to refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

The term "protein" refers to a sequence of more than 100 amino acids and/or to a multimeric entity. The proteins of the invention are not limited to a specific length of the product. The term "polypeptide" or "protein" does not refer to or exclude post-expression modifications of the protein, for example, glycosylation, acetylation, phosphorylation and the like, as well as other modifications known in the art, both naturally occurring and non-naturally occurring. Such modifications are well described in basic texts and in more detailed monographs, as well as in a voluminous research literature. Modifications can occur anywhere in a polypeptide or protein, including the peptide backbone, the amino acid side-chains and the amino or carboxyl termini. It will be appreciated that the same type of modification may be present in the same or varying degrees at several sites in a given polypeptide or protein. Also, a given polypeptide or protein may contain many types of modifications. Polypeptides or proteins may be branched as a result of ubiquitination, and they may be cyclic, with or without branching. Cyclic, branched and branched cyclic polypeptides or proteins may result from posttranslational natural processes or may be made by synthetic methods. Modifications include acetylation, acylation, ADP-ribosylation, amidation, covalent attachment of flavin, covalent attachment of a hem moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-linkings, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino of amino acids to proteins such as arginylation, and ubiquitination. See, for instance, "Proteins-structure and molecular properties", 2nd Ed., T. E. Creighton, W. H. Freeman and Company, New York, 1993; Wolt, F., "Post-translational Protein Modifications: Perspectives and Prospects", Posttranslational covalent modification of proteins, B. C. Johnson, Ed., Academic Press, New York, 1983, pgs. 1-12; Seifter et al., "Analysis for protein modifications and nonprotein cofactors", Meth Enzymol, 1990, 182:626-646; Rattan et al, "Protein Synthesis: Posttranslational Modifications and Aging", Ann NY Acad Sci, 1992, 663:48-62. A protein may be an entire protein, or a subsequence thereof. An "isolated protein" is one that has been identified and separated and/or recovered from a component of its natural environment. In a preferred embodiment, the isolated protein will be purified:

(1) to greater than 80, 85, 90, 95% by weight of protein as determined by the Lowry method, and most preferably more than 96, 97, 98, or 99% by weight,
(2) to a degree sufficient to obtain at least 15 residues of N-terminal or internal amino acid sequence by use of a spinning cup sequenator, or
(3) to homogeneity by SDS-PAGE under reducing or non-reducing conditions using Coomassie blue or, preferably, silver staining.

Isolated protein includes the protein in situ within recombinant cells since at least one component of the protein's natural environment will not be present. Ordinarily, however, isolated protein will be prepared by at least one purification step.

The term "fusion protein" refers to a molecule comprising two or more proteins or fragments thereof linked by a covalent bond via their individual peptide backbones, most preferably generated through genetic expression of a polynucleotide molecule encoding those proteins. In one embodiment, a fusion protein according to the invention comprises an anticoagulant polypeptide, preferably IrCPI, and a serum albumin polypeptide, wherein the components of the fusion protein are linked to each other by peptidebonds, either directly or through peptide linkers. The polypeptides forming the fusion protein are typically linked C-terminus to N-terminus, although they can also be linked C-terminus to C-terminus, N-terminus to N-terminus, or N-terminus to C-terminus. The polypeptides of the fusion proteins may be fused in any order.

The term "fused" refers to components that are linked by peptide bonds, either directly or through one or more peptide linkers.

The term "native IrCPI" refers to naturally occurring IrCPI, as opposed to a "modified IrCPI", which has been modified from a naturally occurring IrCPI, e.g. to alter one or more of its properties such as stability. A modified IrCPI polypeptide may for example comprise modifications in the amino acid sequence, e.g. amino acid substitutions, deletions or insertions.

The term "subject" refers to a mammal, preferably a human. In one embodiment, the subject is a man. In another embodiment, the subject is a woman. In one embodiment, a subject may be a "patient", i.e. a warm-blooded animal, more preferably a human, who/which is awaiting the receipt of, or is receiving medical care or was/is/will be the object of a medical procedure, or is monitored for the development of inflammation. In one embodiment, the subject is an adult (for example a subject above the age of 18). In another embodiment, the subject is a child (for example a subject below the age of 18).

The term "therapeutically effective amount" means the level or amount of agent that is aimed at, without causing significant negative or adverse side effects to the target, (1) delaying or preventing the onset of thrombus; (2) slowing down or stopping the progression, aggravation, or deterioration of one or more symptoms of thrombus; (3) bringing about ameliorations of the symptoms of thrombus; (4) reducing the severity or incidence of thrombus; or (5) preventing thrombus formation. In one embodiment, a therapeutically effective amount is administered prior to the onset of thrombus formation, for a prophylactic or preventive action.

The term "variant" refers to a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions identical. A variant and reference polypeptide may differ in amino acid sequence by one or more substitutions (preferably conservative), additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. Variants should retain one or more of the biological activities of the reference polypeptide. For instance, they should have similar antigenic or immunogenic activities as the reference polypeptide. Antigenicity can be tested using standard immunoblot experiments, preferably using polyclonal sera against the reference polypeptide. The immunogenicity can be tested by measuring antibody responses (using polyclonal sera generated against the variant polypeptide) against purified reference polypeptide in a standard ELISA test. Preferably, a variant would retain all of the above biological activities.

The term "at least one" refers to a number encompassing 1, 2, 3, 4, 5, 6, 7, 8, 9, 10, 12, 14, 16, 18, 20, 25, 30, 35, 40, 45, 50 or more. In some embodiments, "at least one" refers to any number comprised from 1 to 50, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50.

DETAILED DESCRIPTION

This invention relates to a fusion protein comprising at least one *Ixodes ricinus* (*I. ricinus*) salivary gland polypeptide, fragment or variant thereof.

As used herein, the *I. ricinus* salivary gland polypeptide of the invention may also be called IrCPI, Ir-CPI or $R_1$.

According to one embodiment, the IrCPI polypeptide of the invention has an amino sequence comprising or consisting in the sequence SEQ ID NO: 1. In one embodiment, the IrCPI polypeptide of the invention is encoded by the cDNA corresponding to the amino acid sequence SEQ ID NO: 1.

In one embodiment, the amino acid sequence of the IrCPI polypeptide of the invention is at least 75% identical to SEQ ID NO: 1, preferably at least 80%, 85% 90%, 95%, 96%, 97%, 98%, 99% or 100% identical to SEQ ID NO: 1.

In one embodiment, fragments of IrCPI polypeptide are also included in the present invention. As used herein, the term "fragment" means a polypeptide having an amino acid sequence that is the same as part, but not all, of the amino acid sequence of the aforementioned IrCPI polypeptides. As with IrCPI polypeptides, fragment may be "free-standing" or comprised within a larger polypeptide of which they form a part or region, most preferably as a single continuous region. Representative examples of polypeptide fragments of the invention, include, for example, fragments from about amino acid number 1-20, 21-40, 41-60, 61-80, 81-100, and 101 to the end of the polypeptide. In this context "about" includes the particularly recited ranges larger or smaller by several, 5, 4, 3, 2 or 1 amino acid at either extreme or at both extremes.

Preferred fragments include, but are not limited to, truncation polypeptides having the amino acid sequence of the IrCPI polypeptides, except for deletion of a continuous series of residues that includes the amino terminus, or a continuous series of residues that includes the carboxyl terminus and/or transmembrane region or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate IrCPI polypeptide activity, including those with a similar activity or an improved activity, or with a decreased undesirable activity.

In one embodiment, all of these polypeptide fragments retain parts of the biological activity of the IrCPI polypeptides.

In one embodiment, variants of IrCPI polypeptide are also included in the present invention. Preferred variants are those that vary from the referents by conservative amino acid substitutions, i.e. those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, or 1-2 amino acids are substituted, deleted, or added in any combination. Most preferred variants are naturally occurring allelic variants of the IrCPI polypeptide present in *I. ricinus* salivary glands.

In one embodiment, the IrCPI polypeptide of the invention has an amino sequence comprising a mutation leading to the replacement of Asparagine in a position corresponding to position 54 in the amino acid sequence of SEQ ID NO: 1 by Glutamine in order to prevent N-glycosylation. In one embodiment, the IrCPI polypeptide of the invention has an amino sequence comprising or consisting in the sequence of SEQ ID NO: 2.

In one embodiment, the amino acid sequence of the IrCPI polypeptide of the invention is at least 75% identical to SEQ ID NO: 2, preferably at least 80%, 85% 90%, 95%, 96%, 97%, 98%, 99% or 100% identical to SEQ ID NO: 2.

In one embodiment, the fusion protein of the invention comprises more than one IrCPI polypeptide. In one embodiment, the fusion protein of the invention comprises at least two IrCPI polypeptides.

In one embodiment, the IrCPI polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

As used herein, the term "fusion protein" refers to a fusion of IrCPI polypeptide and at least one other polypeptide. As used herein, the fusion protein of the invention may also be called IrCPI-fusion protein, and the at least one other polypeptide of the invention may be referred as $R_2$.

The present invention relates to a fusion protein comprising an *Ixodes ricinus* salivary gland (IrCPI) polypeptide having an increased circulatory half-life compared to an unfused IrCPI polypeptide. In one embodiment, IrCPI is linked to at least one other polypeptide in such a manner as to produce a single protein which retains the biological activity of IrCPI.

In one embodiment, the fusion proteins of the invention have improved blood half-life without increasing hemorrhagic risks.

In one embodiment, the at least one other polypeptide is selected from the group comprising or consisting of albumin, preferably serum albumin, more preferably human serum albumin, linear or branched-chain monomethoxy poly-ethylene glycol (PEG), hyaluronic acid, Fc domain of IgG, human IgG, transferrin, homo-amino acid polymer (HAP), proline-alanine-serine polymer (PAS), elastin-like peptide (ELP), negatively charged highly sialylated peptide (e.g., carboxy-terminal peptide, CTP, from human CG β-subunit) and hybrid repetitive motif (HRM).

In a preferred embodiment, the at least one other polypeptide is selected from the group consisting of human serum albumin, PEG, Fe domain of IgG, and human IgG. In a more preferred embodiment, the at least one other polypeptide is human serum albumin or PEG.

In one embodiment, the polypeptides of the fusion protein are linked C-terminus to N-terminus. In another embodiment, the components of the fusion protein are linked C-terminus to C-terminus. In another embodiment, the components of the fusion protein are linked N-terminus to N-terminus. In another embodiment, the components of the fusion protein are linked N-terminus to C-terminus.

In one embodiment, the polypeptides of the fusion protein may be fused in any order.

In one embodiment, the polypeptides are disposed in a single, contiguous polypeptide chain.

Specific fusion protein constructs are named by listing IrCPI and $R_2$ in the fusion protein in their order of occurrence (with the N terminal domain specified first, followed by the C-terminal domain). Thus, in one embodiment, IrCPI-$R_2$ refers to a fusion protein comprising IrCPI followed by $R_2$ (i.e., the C-terminus of IrCPI is linked to the N-terminus of $R_2$).

In one embodiment, the fusion protein of the invention comprises at least one serum albumin polypeptide, fragments or variants thereof. As used herein, the serum albumin polypeptide may also be referred as SA.

Therefore, in one embodiment, the fusion protein of the invention comprises at least one IrCPI polypeptide and at least one serum albumin polypeptide. In one embodiment, the fusion protein of the invention comprises a first polypeptide fused to a second polypeptide, wherein the first polypeptide comprises an IrCPI polypeptide, and wherein the second polypeptide comprises a serum albumin polypeptide.

In one embodiment, the fusion protein of the invention is a fusion protein of a serum albumin polypeptide and an IrCPI polypeptide.

In one embodiment, the fusion protein comprises (i) at least one IrCPI polypeptide, having an amino sequence at least 75% identical to SEQ ID NO: 1, (ii) at least one serum albumin polypeptide and (iii) at least one peptide linker, wherein the fusion protein has an increased circulatory half-life compared to an unfused IrCPI polypeptide.

In one embodiment, the serum albumin polypeptide of the invention is a human serum albumin. As used herein, the human serum albumin polypeptide may also be referred as HSA.

According to one embodiment, the serum albumin polypeptide of the invention has an amino sequence comprising or consisting in the sequence of SEQ ID NO: 3.

In one embodiments, fragments and variants of serum albumin polypeptide are also included in the present invention.

In one embodiment, the variant of the serum albumin polypeptide of the invention does not comprise a substitution in a position corresponding to position 573 in the amino acid sequence of SEQ ID NO: 3, wherein the substitution is selected from the group consisting of K573A, C, D, F, G, H, I, L, M, N, P, Q, R, S, V, W, and Y.

In another embodiment, the variant of the serum albumin polypeptide of the invention does not comprise a substitution in positions corresponding to the positions in SEQ ID NO: 3 selected among: 573, 500, 550, 492, 580, 574, 417, 440, 464, 490, 493, 494, 495, 496, 499, 501, 503, 504, 505, 506, 510, 535, 536, 537, 538, 540, 541, 542, 575, 577, 578, 579, 581, 582 and 584. In a particular embodiment, the variant of serum albumin polypeptide of the invention is not the variant consisting of SEQ ID NO: 3 with the substitution D494N, E501K, K541E, D550G, D550A, K573E or K574N.

In another embodiment, the variant of the serum albumin polypeptide of the invention does not comprise an alteration at one or more positions corresponding to 104, 106, 108, 109, 110, and 120 in SEQ ID NO: 3 with one or more of A, C, D, E, F, G, H, I, K, L, M, N, P, Q, R, S, T, V, W, Y.

In one embodiment, the fusion protein of the invention comprises more than one serum albumin polypeptide. In one embodiment, the fusion protein of the invention comprises two serum albumin polypeptides or more.

In one embodiment, the N-terminus of a serum albumin polypeptide (SA), preferably a human serum albumin polypeptide (HSA), is fused to the C-terminus of an *I. ricinus* salivary gland polypeptide (IrCPI). The obtained fusion protein is called SA-IrCPI, preferably HSA-IrCPI.

In another embodiment, the N-terminus of an IrCPI polypeptide is fused to the C-terminus of a SA polypeptide, preferably a HSA. The obtained fusion protein is called IrCPI-SA, preferably IrCPI-HSA.

In one embodiment, the fusion protein of the invention has an amino sequence comprising or consisting in the sequence of SEQ ID NO: 4 (IrCPI-HSA, called V1 fusion protein). In another embodiment, the fusion protein of the invention has an amino sequence comprising or consisting in the sequence of SEQ ID NO: 5 (HSA-IrCPI, called V2 fusion protein). In another embodiment, the fusion protein of the invention has an amino sequence comprising or consisting in the sequence of SEQ ID NO: 6 (IrCPI-IrCPI-HSA, called V5 fusion protein). In another embodiment, the fusion protein of the invention has an amino sequence comprising or consisting in the sequence of SEQ ID NO: 7 (HSA IrCPI-IrCPI, called V10 fusion protein).

In one embodiment, the fusion protein of the invention further comprises at least one peptide linker. In one embodiment, the polypeptides of the fusion protein of the invention are linked to each other through one or more peptide linkers.

In one embodiment, the fusion proteins of the invention have a general formula selected from the group consisting of $R_1$-$R_2$, $R_1$-$R_1$-$R_2$, $R_2$-$R_1$, $R_2$-$R_1$-$R_1$, $R_1$-L-$R_2$, $R_1$-$R_1$-L-$R_2$, $R_1$-L-$R_1$-L-$R_2$, $R_1$-L-$R_2$-L-$R_1$, $R_2$-L-$R_1$, $R_2$-L-$R_1$-$R_1$, $R_2$-L-$R_1$-L-$R_1$, wherein $R_1$ is IrCPI, $R_2$ is serum albumin and L is a linker peptide sequence.

In one embodiment, the term "IrCPI-fusion proteins" or "fusion proteins" indiscriminately refers to fusion proteins without a peptide linker sequence added or with a peptide linker sequence added.

In one embodiment, the linker peptide provides a greater physical separation between the two moieties and thus maximizes the availability of the *I. ricinus* salivary gland polypeptide. The linker peptide may consist of amino acids such that it is flexible or more rigid.

In about one embodiment, the peptide linker of the invention comprises from 1 to 60 amino acids, preferably from 2 to 50 amino acids, more preferably from 4 to 40 amino acids. In one embodiment, the peptide linker of the invention comprises from 5 to 50 amino acids, from 10 to 50 amino acids, from 15 to 50 amino acids, or from 20 to 50 amino acids. In another embodiment, the peptide linker of the invention comprises from 6 to 20 amino acids, from 8 to 20 amino acids, or from 10 to 20 amino acids. In another embodiment, the peptide linker of the invention comprises from 2 to 10 amino acids, from 5 to 20 amino acids, from 10 to 30 amino acids, or from 15 to 40 amino acids.

In one embodiment, the peptide linker of the invention comprises at least 4, 5, 6, 7, 8, 9, 10, 11, 12 or 15 amino acids. In one embodiment, the peptide linker of the invention comprises at most 20, 19, 18, 17, 16, 15, 14, 13 or 12 amino acids. In another embodiment, the peptide linker of the invention comprises at most 50, 45, 40 or 35 amino acids.

In another embodiment, the peptide linker of the invention comprises from 4 to 50 amino acids.

In one embodiment, the peptide linker of the invention comprises 3, 4, 5, 6, 7, 8 or 9 amino acids. In another embodiment, the peptide linker of the invention comprises 10, 11, 12, 13, 14, 15, 16 or more amino acids. In another embodiment, the peptide linker of the invention comprises 20, 25, 30, 35, 40, 45 or more amino acids.

In one embodiment, the peptide linker of the invention comprises 5 amino acids. In another embodiment, the peptide linker of the invention comprises 7 amino acids. In another embodiment, the peptide linker of the invention comprises 12 amino acids. In another embodiment, the peptide linker of the invention comprises 14 amino acids. In another embodiment, the peptide linker of the invention comprises 16 amino acids. In another embodiment, the peptide linker of the invention comprises 22 amino acids. In another embodiment, the peptide linker of the invention comprises 28 amino acids. In another embodiment, the peptide linker of the invention comprises 31 amino acids. In another embodiment, the peptide linker of the invention comprises 46 amino acids.

In some embodiments, the at least one peptide linker is selected from a group comprising Gly-rich linkers, Ser-rich linkers, Gly-rich and Ser-rich linkers, Pro-rich linkers, helical linkers, linkers non-cleavable by a protease, linkers cleavable by a protease and a combination thereof.

Examples of peptide linkers include, but are not limited to, Gly-rich linkers such as poly-Gly linkers, i.e., a (Gly-Gly-Gly-Gly)$_n$ linker, (SEQ ID NO: 8), wherein "n" is a number from 1 to 10; Ser-rich linkers such as a (Ser-Ser-Ser-Gly)$_n$ linker, (SEQ ID NO: 9), wherein "n" is a number from 1 to 10, KESGSVSSEQLAQFRSLD (SEQ ID NO: 18) and EGKSSGSGSESKST (SEQ ID NO: 19); Gly-rich and Ser-rich linkers comprising stretches of Gly and Ser residues (also called "GS linkers") such as a (Gly-Gly-Gly-Gly-Ser)$_n$ linker, (SEQ ID NO: 10), wherein "n" is a number from 1 to 10, or GSAGSAAGSGEF (SEQ ID NO: 11), or a GS(GGS)$_n$GS linker wherein "n" is a number from 1 to 20 (SEQ ID NO: 12); Pro-rich linkers, which are sequences such as (XP)$_n$ with X designating any amino acid, preferably Ala, Lys, or Glu, and "n" is a number from 1 to 10, in particular (Ala-Pro)$_n$ linkers wherein "n" is a number from 1 to 20; helical linkers such as a (EAAAK)$_n$ linker, (SEQ ID NO: 14), wherein "n" is a number from 1 to 10, [A(EAAAK)$_n$A]$_m$, (SEQ ID NO: 15), wherein n is a number from 2 to 10 and m is a number from 1 to 5, or the linker called (H4)$_2$: A(EAAAK)$_4$ALEA(EAAAK)$_4$A (SEQ ID NO: 16).

In one embodiment, the peptide linker of the invention is not an in vivo cleavable linker. In one embodiment, the peptide linker of the invention is an in vivo cleavable linker.

In one embodiment, the in vivo cleavable linker is a linker cleavable by a protease. In a particular embodiment, the in vivo cleavable linker is a linker cleavable by a protease of blood. Examples of proteases of blood include, but are not limited to, FVIIa, FIXa, FXa, FXIa, prothrombin, and protein C.

In one embodiment, the peptide linker of the invention is a (EAAAK)$_n$ peptide linker wherein "n" is a number from 1 to 10, preferably from 2 to 5 (SEQ ID NO: 14). In a particular embodiment, the peptide linker of the invention is [A(EAAAK)$_n$A]$_m$ wherein "n" is a number from 1 to 10, preferably from 2 to 5, and "m" is a number from 1 to 5 (SEQ ID NO: 15). In a preferred embodiment, the peptide linker of the invention comprises or consists of the amino acid sequence [A(EAAAK)$_n$A]$_m$, wherein "n" is 2 and "m" is 1 (A(EAAAK)$_2$A, SEQ ID NO: 20). In another particular embodiment, the peptide linker of the invention comprises or consists of the amino acid sequence [A(EAAAK)$_n$A]$_m$, wherein "n" is 4 and "m" is 1 (A(EAAAK)$_4$A, SEQ ID NO: 21).

In another embodiment, the peptide linker of the invention is A(EAAAK)$_n$ALEA-(EAAAK)$_m$A, wherein "n" is a number from 1 to 10, preferably from 2 to 5, and "m" is a number from 1 to 10, preferably from 2 to 5 (SEQ ID NO: 22). In a particular embodiment, the peptide linker of the invention comprises or consists of the amino acid sequence A(EAAAK)$_n$ALEA-(EAAAK)$_m$A, wherein "n" is 4 and "m" is 4 (A(EAAAK)$_4$ALEA-(EAAAK)$_4$A, SEQ ID NO: 16).

In another embodiment, the peptide linker of the invention is an (Ala-Pro)$_n$ peptide linker, also called (AP)$_n$ linker, wherein "n" is a number from 1 to 20, preferably from 2 to 17, more preferably from 2 to 15, more preferably from 5 to 15, even more preferably from 10 to 15. In one embodiment, the peptide linker of the invention is an (AP)$_n$ linker, wherein "n" is 2, 3, 4, 5, 6, 7, 8, 9, 10, 11, 12, 13, 14 or 15.

In one embodiment, the peptide linker of the invention is an AP(AP)$_n$ linker, wherein "n" is a number from 1 to 20, preferably from 2 to 17, more preferably from 2 to 15, more preferably from 5 to 15, even more preferably from 10 to 15 (SEQ ID NO: 49). In one embodiment, the peptide linker of the invention is an AP(AP)$_n$ linker, wherein "n" is 1, 2, 3, 4, 5, 6, 7, 8, 9, 10, 11, 12, 13, 14, 15, 16, 17, 18, 19 or 20 (SEQ ID NO: 49).

In another embodiment, the peptide linker of the invention is a Pro-(Ala-Pro)$_n$ peptide linker, also called P(AP)$_n$ linker, wherein "n" is a number from 1 to 20, preferably from 2 to 17, more preferably from 2 to 15, more preferably from 5 to 15, even more preferably from 10 to 15. In one embodiment, the peptide linker of the invention is a P(AP)$_n$ linker, wherein "n" is 1, 2, 3, 4, 5, 6, 7, 8, 9, 10, 11, 12, 13, 14 or 15.

In one embodiment, the peptide linker of the invention is a PAP(AP)$_n$ linker, wherein "n" is a number from 1 to 20, preferably from 2 to 17, more preferably from 2 to 15, more preferably from 5 to 15, even more preferably from 10 to 15 (SEQ ID NO: 23). In one embodiment, the peptide linker of the invention is a PAP(AP)$_n$ linker, wherein "n" is 1, 2, 3, 4, 5, 6, 7, 8, 9, 10, 11, 12, 13, 14, 15, 16, 17, 18, 19 or 20 (SEQ ID NO: 23).

In a particular embodiment, the peptide linker of the invention comprises or consists of the amino acid sequence P(AP)$_2$ (SEQ ID NO: 24). In another particular embodiment, the peptide linker of the invention comprises or consists of the amino acid sequence (AP)$_7$ (SEQ ID NO: 25). In another particular embodiment, the peptide linker of the invention comprises or consists of the amino acid sequence (AP)$_{14}$ (SEQ ID NO: 26).

In another embodiment, the peptide linker of the invention is a Pro-rich linker selected from a group comprising (AP)$_n$ and P(AP)$_n$ linker wherein "n" is a number from 1 to 20, preferably from 2 to 17, more preferably from 2 to 15, more preferably from 5 to 15, even more preferably from 10 to 15.

In another embodiment, the peptide linker of the invention is a so-called "GS" peptide linker. In one embodiment, the peptide linker of the is a G$_1$S linker wherein "n" is a number from 1 to 10, preferably from 2 to 7, more preferably from 3 to 5. In one embodiment, the peptide linker of the is a G$_n$GGS linker wherein "n" is a number from 1 to 7, preferably from 1 to 5, more preferably from 1 to 3 (SEQ ID NO: 50). In one embodiment, the peptide linker of the invention is a G$_n$S(G$_n$S)$_m$ linker wherein "n" is a number from 1 to 10, preferably from 2 to 7, more preferably from 3 to 5 and wherein "m" is a number from 1 to 10, preferably from 2 to 7, more preferably from 3 to 5 (SEQ ID NO: 51). In a particular embodiment, the peptide linker of the invention is a (G$_4$S)$_m$ linker wherein "m" is a number from 1 to 10, preferably from 2 to 7, more preferably from 3 to 5 (SEQ ID NO: 10).

In one embodiment, the peptide linker of the invention is a G$_n$S(G$_n$S)$_m$A linker, wherein "n" is a number from 1 to 10, preferably from 2 to 7, more preferably from 3 to 5 and wherein "m" is a number from 1 to 10, preferably from 2 to 7, more preferably from 3 to 5 (SEQ ID NO: 52). In a particular embodiment, the peptide linker of the invention comprises or consists of the amino acid sequence (G$_4$S)$_3$A (SEQ ID NO: 27). In one embodiment, the peptide linker of the invention is a GS(GGS)$_n$GS linker, wherein "n" is a number from 1 to 20, preferably from 2 to 17, more preferably from 5 to 15 (SEQ ID NO: 12). In another particular embodiment, the peptide linker of the invention comprises or consists of the amino acid sequence GS(GGS)$_n$GS linker, wherein "n" is 4 (GS(GGS)$_4$GS, SEQ ID NO: 28). In another particular embodiment, the peptide linker of the invention comprises or consists of the amino acid sequence GS(GGS)$_n$GS linker, wherein "n" is 9 (GS (GGS)$_9$GS, SEQ ID NO: 29).

In one embodiment, the peptide linker of the invention is used to link the at least one *I. ricinus* salivary gland polypeptide and the at least one other polypeptide, preferably a serum albumin polypeptide, more preferably a human serum albumin polypeptide.

In one embodiment, the N-terminus of the peptide linker is fused to the C-terminus of the at least one other polypeptide, preferably a serum albumin polypeptide, and the C-terminus of the peptide linker is fused to the N-terminus of a IrCPI polypeptide. The obtained fusion protein is called R$_2$-L-IrCPI, preferably SA-L-IrCPI, more preferably HSA-L-IrCPI.

In another embodiment, the N-terminus of the peptide linker is fused to the C-terminus of a IrCPI polypeptide and the C-terminus of the peptide linker is fused to the N-terminus of the at least one other polypeptide, preferably a serum albumin polypeptide. The obtained fusion protein is called IrCPI-L-R$_2$, preferably IrCPI-L-SA, more preferably IrCPI-L-HSA.

In one embodiment, the fusion protein of the invention comprises, from N-terminus to C-terminus, the at least one other polypeptide, preferably a serum albumin polypeptide, a peptide linker, and an IrCPI polypeptide.

In another embodiment, the fusion protein of the invention comprises, from N-terminus to C-terminus, an IrCPI polypeptide, a peptide linker, and at least one other polypeptide, preferably a serum albumin polypeptide.

In one embodiment, the fusion protein of the invention has an amino sequence comprising or consisting in the sequence of SEQ ID NO: 32 (IrCPI-AEAAAKEAAAKA-HSA, called V8 fusion protein). In another embodiment, the fusion protein of the invention has an amino sequence comprising or consisting in the sequence of SEQ ID NO: 30 (HSA-AEAAAKEAAAKA-IrCPI, called V9 fusion protein).

In one embodiment, the fusion protein of the invention has an amino sequence comprising or consisting in the sequence of SEQ ID NO: 33 (IrCPI-A(EAAAK)$_4$A-HSA, called V16 fusion protein). In another embodiment, the fusion protein of the invention has an amino sequence comprising or consisting in the sequence of SEQ ID NO: 34 (HSA-A(EAAAK)$_4$A-IrCPI, called V22 fusion protein).

In one embodiment, the fusion protein of the invention has an amino sequence comprising or consisting in the sequence of SEQ ID NO: 35 (IrCPI-A(EAAAK)$_4$ALEA-(EAAAK)$_4$A-HSA, called V17 fusion protein). In another embodiment, the fusion protein of the invention has an amino sequence comprising or consisting in the sequence of SEQ ID NO: 36 (HSA-A(EAAAK)$_4$ALEA-(EAAAK)$_4$A-IrCPI, called V23 fusion protein).

In one embodiment, the fusion protein of the invention has an amino sequence comprising or consisting in the sequence of SEQ ID NO: 31 (IrCPI-(AP)$_7$—HSA, called V12 fusion protein). In another embodiment, the fusion protein of the invention has an amino sequence comprising or consisting in the sequence of SEQ ID NO: 37 (HSA-(AP)$_7$—IrCPI, called V18 fusion protein).

In one embodiment, the fusion protein of the invention has an amino sequence comprising or consisting in the sequence of SEQ ID NO: 38 (IrCPI-(AP)$_{14}$—HSA, called V13 fusion protein). In another embodiment, the fusion protein of the invention has an amino sequence comprising or consisting in the sequence of SEQ ID NO: 39 (HSA-(AP)$_{14}$-IrCPI, called V19 fusion protein).

In one embodiment, the fusion protein of the invention has an amino sequence comprising or consisting in the sequence of SEQ ID NO: 40 (IrCPI-PAPAP-HSA, called V6 fusion protein). In another embodiment, the fusion protein of the invention has an amino sequence comprising or consisting in the sequence of SEQ ID NO: 41 (HSA-PAPAP-IrCPI, called V7 fusion protein).

In one embodiment, the fusion protein of the invention has an amino sequence comprising or consisting in the sequence of SEQ ID NO: 47 (IrCPI-(G$_4$S)-HSA, called V3 fusion protein). In another embodiment, the fusion protein of the invention has an amino sequence comprising or consisting in the sequence of SEQ ID NO: 48 (HSA-(G$_4$S)-IrCPI, called V4 fusion protein).

In one embodiment, the fusion protein of the invention has an amino sequence comprising or consisting in the sequence of SEQ ID NO: 42 (IrCPI-(G$_4$S)$_3$A-HSA, called V14 fusion protein). In another embodiment, the fusion protein of the invention has an amino sequence comprising or consisting in the sequence of SEQ ID NO: 43 (HSA-(G$_4$S)$_3$A-IrCPI, called V20 fusion protein).

In one embodiment, the fusion protein of the invention has an amino sequence comprising or consisting in the sequence of SEQ ID NO: 44 (IrCPI-GS(GGS)$_9$GS-HSA, called V15 fusion protein). In another embodiment, the fusion protein of the invention has an amino sequence comprising or consisting in the sequence of SEQ ID NO: 45 (HSA-GS(GGS)$_9$GS-IrCPI, called V21 fusion protein).

In one embodiment, the fusion protein of the invention has an amino sequence comprising or consisting in the sequence of SEQ ID NO: 46 (IrCPI-(AP)$_7$—IrCPI-(AP)$_{14}$—HSA, called V27 fusion protein).

In one embodiment, the fusion protein of the invention has an amino sequence comprising or consisting in the sequence of SEQ ID NO: 13 (IrCPI-(G4S)$_3$A-HSA-(G4S)$_3$A-IrCPI, called V25 fusion protein).

In one embodiment, the fusion protein of the invention has an amino sequence comprising or consisting in the sequence of SEQ ID NO: 17 (IrCPI-(AP)$_{14}$-HSA-(AP)$_{14}$-IrCPI, called V26 fusion protein).

In one embodiment, the fusion protein of the invention is selected from a group of fusion proteins having an amino acid sequence comprising or consisting in the sequence of SEQ ID NO: 4, SEQ ID NO: 5, SEQ ID NO: 6, SEQ ID NO: 7, SEQ ID NO: 13, SEQ ID NO: 17, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47 and SEQ ID NO: 48.

In one embodiment, the fusion polypeptide of the invention may be in the form of the "mature" protein or may be a part of a larger protein. It may be advantageous to include an additional amino acid sequence which contains secretory or leader sequences, pro-sequences, sequences which help in purification such as multiple histidine residues, or an additional sequence for stability during recombinant production.

Fusion proteins of the invention may be obtained, for example, by solid-state peptide synthesis (e.g. Merrifield solid phase synthesis) or recombinant production. For recombinant production one or more polynucleotide encoding the fusion protein (fragment), e.g., as described above, is isolated and inserted into one or more vectors for further cloning and/or expression in a host cell. Such polynucleotide may be readily isolated and sequenced using conventional procedures.

Methods which are well known to those skilled in the art can be used to construct expression vectors containing the coding sequence of a fusion protein (fragment) along with appropriate transcriptional/translational control signals. These methods include in vitro recombinant DNA techniques, synthetic techniques and in vivo recombination/genetic recombination. See, for example, the techniques described in Maniatis et al, MOLECULAR CLONING: A LABORATORY MANUAL, Cold Spring Harbor Laboratory, N.Y. (1989); and Ausubel et al, CURRENT PROTOCOLS IN MOLECULAR BIOLOGY, Greene Publishing Associates and Wiley Interscience, N.Y (1989). The expression vector can be part of a plasmid, virus, or may be a nucleic acid fragment. The expression vector includes an expression cassette into which the polynucleotide encoding the fusion protein (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the fusion protein (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells.

Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit a-globin, as well as other sequences capable of controlling gene expression in eukaryotic cells. Additional suitable transcription control regions include tissue-specific promoters and enhancers as well as inducible promoters (e.g. promoters inducible tetraclyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Fusion proteins prepared as described herein may be purified by art-known techniques such as high-performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the fusion protein binds. The purity of the fusion protein can be determined by any of a variety of well-known analytical methods including gel electrophoresis, high pressure liquid chromatography, and the like.

The invention further relates to a polynucleotide or nucleic acid encoding a fusion protein as described hereinabove.

The polynucleotides encoding fusion proteins of the invention may be expressed as a single polynucleotide that encodes the entire fusion protein or as multiple (e.g., two or more) polynucleotides that are co-expressed. Polypeptides encoded by polynucleotides that are co-expressed may associate through, e.g., disulfide bonds or other means to form a functional fusion protein.

In one embodiment, the polynucleotide or nucleic acid is DNA. In another embodiment, the polynucleotide of the invention is RNA, for example, in the form of messenger RNA (mRNA). RNA of the present invention may be single stranded or double stranded.

Another object of the present invention is a vector comprising one or more polynucleotides encoding a fusion protein of the invention. In a preferred embodiment, the vector of the invention is an expression vector.

An object of the invention is a composition comprising a fusion protein, a polynucleotide or a vector of the invention as described hereinabove.

The present invention also relates to pharmaceutical compositions comprising a fusion protein, a polynucleotide or a vector as described hereinabove and at least one pharmaceutically acceptable excipient.

Pharmaceutically acceptable excipients that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

Another object of the invention is a medicament comprising a fusion protein, a polynucleotide, a vector, a composition or a pharmaceutical composition according to the present invention.

A further object of the invention relates to the use of a fusion protein, a polynucleotide, a vector, a composition or a pharmaceutical composition according to the present invention in the manufacture of a medicament.

In one embodiment, the pharmaceutical composition or the medicament of the invention comprises a therapeutically effective amount of the fusion protein or polynucleotide according to the invention.

A further object of the present invention is a medical device coated with a fusion protein as described hereinabove.

Furthermore, another object of the present invention is the use of a fusion protein as described hereinabove for coating a medical device. Still another object of the present invention is a fusion protein as described hereinabove for coating a medical device.

Accordingly, the present invention also relates to a medical device coated with a fusion protein as described hereinabove.

Examples of medical devices that may be coated with the fusion protein of the invention include, but are not limited to, cardiovascular stents and related devices such as coronary stents, drug-eluting stents, bare-metal coronary stents, stent-related implants, synthetic grafts, vascular grafts, peripheral grafts and vena cava filters, artificial hearts, artificial heart valves, arterial stents for stenosis and aneurysm, ventricular assist devices (for example left ventricular assist devices, implantable heart monitors, cardiac valves, pacing devices such as cardiac resynchronization therapy devices, implantable cardioverter-defibrillators, and implantable cardiac pacemakers, central venous lines, cardioplegia delivery systems, dilators, tunneling devices, stent grafts cannulae, catheters, extracorporeal circulation systems including but not limited to extracorporeal membrane oxygenation systems, (auto)transfusion systems, arterial filters, hemodialysis systems, plasmapheresis systems, medical devices used for collection of blood outside the body, and accessories for any one of said devices including but not limited to tubing, cannulae, centrifugal pump, valve, port, and/or diverter.

Another object of the present invention is a fusion protein, a polynucleotide, a vector, a pharmaceutical composition, a medicament or a medical device coated with a fusion protein as described hereinabove for preventing, or for use in preventing, thrombus formation and/or thrombus growth. In one embodiment, the fusion protein, a polynucleotide, a vector, a pharmaceutical composition, a medicament or a medical device coated with a fusion protein of the invention is for use for significantly reducing the risk of thrombus formation in a subject in need thereof. In a particular embodiment, the fusion protein, a polynucleotide, a vector, a pharmaceutical composition, a medicament or a medical device coated with a fusion protein of the invention is for preventing, or for use for preventing, thrombus formation in a subject in need thereof. In another particular embodiment, the fusion protein, a polynucleotide, a vector, a pharmaceutical composition or a medicament of the invention is for preventing, or for use for preventing, thrombus growth in a subject in need thereof.

In a particular embodiment, the fusion protein, a polynucleotide, a vector, a pharmaceutical composition, a medicament or a medical device coated with a fusion protein of the invention is for preventing, or for use for preventing, restenosis following invasive procedures such as angioplasty in a subject in need thereof.

In one embodiment, thrombus is due to venous thrombosis. In a particular embodiment, thrombus is associated, but not limited, to deep vein thrombosis, portal vein thrombosis, renal vein thrombosis, jugular vein thrombosis, Budd-Chiari syndrome, Paget-Schroetter disease, cerebral venous sinus thrombosis, cavernous sinus thrombosis, thromboangiitis obliterans (Buerger disease), cancer, hypercoagulopathy, venous embolism including but not limited to thromboembolism, and/or hereditary thrombophilia.

In another embodiment, thrombus is due to arterial thrombosis. In a particular embodiment, thrombus is associated, but not limited, to arterial thrombosis, atherosclerosis, arteriosclerosis, cerebral ischemia, transient ischemic attacks, strokes, cardiac ischemia, unstable angina, acute myocardial infarction, arterial embolism including but not limited to thromboembolism, preeclampsia, disseminated coagulopathy, carotid endarterectomy, thromboangiitis obliterans (Buerger disease), atrial fibrillation, mitral stenosis, endocarditis, hypercoagulability, cancer, metastasis and/or chemotherapy.

In another embodiment, thrombus is due to medical device. In a particular embodiment, thrombus is due to a medical device used in arteries during angioplasty, including but not limited to catheters, cardiovascular guidewires, dilators, tunneling devices, stents, stent grafts; medical device including intra-cardiac devices and devices used in the coronary and peripheral vasculature; extracorporeal circulation systems including but not limited to extracorporeal membrane oxygenation systems, (auto)transfusion systems, arterial filters, hemodialysis systems, plasmapheresis systems; medical device used for collection of blood outside the body; and/or accessories for any one of said devices including but not limited to tubing, cannulae, centrifugal pump, valve, port, and/or diverter.

In another embodiment, thrombus is due to organ transplantations or grafts. The origin of the organ transplanted or the graft can be a tissue-engineered organ or graft, an autograft, an isograft, an allograft or a xenograft.

In one embodiment, thrombus is due to a disease or condition associated with the activation of the extrinsic coagulation pathway. Examples of diseases or conditions associated with the activation of the extrinsic coagulation pathway include thrombosis, inflammatory diseases with thrombotic tendency (also referred to as thrombotic complications in inflammatory diseases), thromboinflammation, device-induced thromboinflammation, diseases and conditions associated with cardiac surgical interventions, and cancer and metastasis.

According to an embodiment, thrombus is due to thrombosis associated with the activation of the extrinsic coagulation pathway. Examples of thrombosis associated with the activation of the extrinsic coagulation pathway include venous thrombosis, cancer-associated thrombosis and stroke-associated thrombosis. According to another embodiment, thrombus is due to an inflammatory disease with thrombotic tendency associated with the activation of the extrinsic coagulation pathway. Examples of such inflammatory diseases with thrombotic tendency include, without being limited to, Beheet's disease (BD), antineutrophil cytoplasmic antibody-associated (ANCA) vasculitides, Takayasu arteritis, rheumatoid arthritis, systemic lupus erythematosus, antiphospholipid syndrome, familial Mediterranean fever, thromboangiitis obliterans (TAO), sepsis and inflammatory bowel disease.

In a particular embodiment, the fusion protein, a polynucleotide, a vector, a pharmaceutical composition, a medicament or a medical device coated with a fusion protein of the invention is for treating or preventing, or for use for treating or preventing thromboinflammation or device-induced thromboinflammation.

According to one embodiment, thrombus is or is due to thromboinflammation. Examples of thromboinflammation are stroke-associated thrombosis, atherosclerosis and plaque rupture, coronary artery disease, acute myocardial infraction, thrombus formation following cerebral injuries, heparin-induced thrombocytopenia (HIT), immunothrombosis, thrombosis associated with preeclampsia, thrombotic complication in cell and cell cluster transplantation and in whole organ transplantation or grafts, venous thromboembolism, aneurysms, and skeletal muscle ischemia-reperfusion syndrome.

According to another embodiment, thrombus is or is due to device-induced thromboinflammation associated with the activation of the extrinsic coagulation pathway. Examples of such device-induced thromboinflammation includes inflammations induced by catheterism (such as, for example, percutaneous transluminal angioplasty) and/or stent positioning procedures at the site of local vascular stenosis, and extracorporeal circulation such as extracorporeal circulation with membrane oxygenation (ECMO). According to another embodiment, thrombus is due to diseases and conditions associated with cardiac surgical interventions and with the activation of the extrinsic coagulation pathway, such as thrombosis and/or coagulation associated to the extracorporeal circulation done within the context of a cardiac surgical intervention. According to yet another embodiment, thrombus is due to cancer- and/or metastasis-associated thrombosis, associated with the activation of the extrinsic coagulation pathway.

According to another embodiment, thrombus is due to a cardiovascular disease, a neurological disease and/or a cancer or metastasis.

Another object of the present invention is a fusion protein, a polynucleotide, a vector, a pharmaceutical composition, a medicament or a medical device coated with a fusion protein as described hereinabove for treating or preventing, or for use in treating or preventing, cardiovascular and/or neurological diseases.

In a particular embodiment, the fusion protein, polynucleotide, vector, pharmaceutical composition medicament or a medical device coated with a fusion protein of the invention is for treating or preventing, or for use in treating or preventing, cardiovascular diseases in a subject in need thereof. In another particular embodiment, the fusion protein, polynucleotide, vector, pharmaceutical composition, medicament or a medical device coated with a fusion protein of the invention is for treating or preventing, or for use in treating or preventing, neurological diseases in a subject in need thereof.

Examples of cardiovascular diseases include, but are not limited to, thromboembolism, stroke, myocardial infarction, cerebrovascular diseases, cerebral ischemia, pulmonary embolism, renal vein thrombosis and hepatic vein thrombosis.

Examples of neurological diseases include, but are not limited to, Huntington's disease, Parkinson's disease, Alzheimer's disease, stroke, epilepsy and brain tumor. In one embodiment, the neurological disease is a disease of the blood vessels that supply the brain, such as for example stroke.

In one embodiment, cardiovascular and/or neurological diseases of the invention are associated with thrombosis.

Advantageously, the fusion protein, polynucleotide, vector, pharmaceutical composition, medicament or a medical device coated with a fusion protein of the invention of the present invention, while preventing thrombosis and/or treating or preventing cardiovascular and/or neurological diseases, does not affect blood clotting of the treated subject.

Another object of the present invention is a fusion protein, a polynucleotide, a vector, a pharmaceutical composition, a medicament or a medical device coated with a fusion protein as described hereinabove for treating or preventing, or for use in treating or preventing, cancer and metastasis.

In a particular embodiment, the fusion protein, polynucleotide, vector, pharmaceutical composition, medicament or a medical device coated with a fusion protein of the invention is for treating or preventing, or for use in treating or preventing, cancer and metastasis in a subject in need thereof. In one embodiment, cancer and metastasis are associated with thrombosis.

The Applicant has demonstrated that *Ixodes ricinus* salivary gland polypeptides inhibit the recruitment of polymorphonuclear neutrophils (PMNs) and platelets at the sites of lesion in an experimental mouse arteriolar laser injury model reported to be strictly dependent of TF and independent of FXII (Darbousset et al., 2012). In addition, the Applicant also found that *Ixodes ricinus* salivary gland polypeptides inhibit in vitro the activation of PMNs and the formation of neutrophil extracellular traps (also called NETosis). While not willing to be bound by any theory, the Applicant thus concludes that IrCPI inhibits the recruitment and activation of neutrophils at the site of lesion and thus plays a role in the recruitment and activation of cells involved when the extrinsic coagulation pathway is activated.

Therefore, another object of the present invention is a fusion protein, a polynucleotide, a vector, a pharmaceutical composition, a medicament or a medical device coated with a fusion protein as described hereinabove for inhibiting platelet recruitment, neutrophil recruitment, neutrophil activation and/or neutrophil extracellular trap formation (NETosis).

In one embodiment, inhibiting platelet recruitment, neutrophil recruitment, neutrophil activation and/or NETosis treats and/or prevents diseases or conditions associated with platelet recruitment, neutrophil recruitment, neutrophil activation and/or NETosis.

In one embodiment, the disease or condition associated with platelet recruitment, neutrophil recruitment, neutrophil activation and/or NETosis is selected from the group comprising thrombosis (including venous and arterial thrombosis), thromboinflammation (including devices-induced thromboinflammation), diseases and conditions associated to cardiac surgical interventions, cardiovascular diseases, cancer and metastasis. In one embodiment, the disease or condition associated with platelet recruitment, neutrophil recruitment, neutrophil activation and/or NETosis is thromboinflammation.

A further object of the present invention is a fusion protein, a polynucleotide, a vector, a pharmaceutical composition, a medicament or a medical device coated with a fusion protein as described hereinabove for inhibiting the extrinsic coagulation pathway. In one embodiment, the fusion protein, a polynucleotide, a vector, a pharmaceutical composition, a medicament or a medical device coated with a fusion protein as described hereinabove is for inhibiting the cellular part of the extrinsic coagulation pathway.

In one embodiment, inhibiting the extrinsic coagulation pathway treats and/or prevents diseases and conditions associated to the extrinsic coagulation pathway, in particular thrombus associated to the activation of the extrinsic coagulation pathway.

In one embodiment, inhibiting platelet recruitment, neutrophil recruitment, neutrophil activation and/or NETosis includes inhibiting the extrinsic coagulation pathway.

In one embodiment, treating and/or preventing diseases and conditions associated with the recruitment of platelets, activation of neutrophils, recruitment of neutrophils and/or NET formation in a subject in need thereof consists of treating and/or preventing diseases and conditions associated with the activation of the extrinsic coagulation pathway.

In one embodiment, the subject is susceptible to form thrombus. In one embodiment, the subject is at risk of developing thrombus. In another embodiment, the subject suffers or have suffered from thrombus.

Examples of risks of developing thrombus include, but are not limited to, trauma or fractures, recent myocardial infarction or stroke, major orthopaedic surgery, oncological or non-oncological surgery, respiratory or heart failure, inflammatory bowel disease (e.g. ulcerative colitis or Crohn's disease), severe infection, oral contraceptives and hormone replacement therapy, pregnancy and postpartum, hypercoagulability, cancer, personal/family history of thrombus, age (especially >60 years), obesity (body mass index >30 kg/m$^2$), immobility (including lower extremity paralysis), prolonged travel, metabolic syndrome, dehydration, air pollution and the like.

In one embodiment, the subject is susceptible to develop cardiovascular and/or neurological diseases. In one embodiment, the subject is at risk of developing cardiovascular and/or neurological diseases. In another embodiment, the subject suffers or have suffered from cardiovascular and/or neurological diseases.

In one embodiment, the subject is susceptible to develop cancer and/or metastasis. In one embodiment, the subject is at risk of developing cancer and/or metastasis. In one embodiment, the subject suffers or have suffered from a cancer and/or metastasis.

In one embodiment, the subject recently underwent a surgery. By "recently", it is meant in one embodiment within 1 day, 2 days, 3 days, 4 days, 5 days, 6 days or more. In another embodiment, the term "recently" means within 2 hours, 4 hours, 6 hours, 12 hours, 18 hours or 24 hours.

In another embodiment, the subject is planned undergo a surgery. By "is planned to", it is meant in one embodiment within 2 hours, 4 hours, 6 hours, 12 hours, 18 hours or 24 hours. In another embodiment, the term "is planned to" means within 1 day, 2 days, 3 days, 4 days, 5 days, 6 days or more.

In one embodiment, the subject was not previously treated for thrombus. In another embodiment, the subject previously received one, two or more other treatments for thrombus.

In one embodiment, the subject was not previously treated for a cardiovascular and/or neurological disease. In another embodiment, the subject previously received one, two or more other treatments for cardiovascular and/or neurological diseases.

As used herein, the term "treatment" encompasses prophylactic and therapeutic treatments.

In one embodiment, the subject of the invention is elderly. As used herein, the term "elderly" means that the subject is at least 50 years old, at least 55, 60, 65, 70, 75, 80, 85 or 90 years old.

In another embodiment, the subject of the invention is young. As used herein, the term "young" means that the subject is at most 25 years old, at most 20, 18, 16, 14, 12, 10 or 8 years old. In one embodiment, the subject of the invention is a child, i.e. is below 18 years old.

In one embodiment, the subject is a man. In another embodiment, the subject is a woman.

It will be understood that the total daily usage of the fusion protein of the invention, polynucleotide, vector, composition, pharmaceutical composition, medicament and medical devices coated with the fusion protein of the present invention will be decided by the attending physician within the scope of sound medical judgment. The specific therapeutically effective dose level for any particular patient will depend upon a variety of factors including the disorder being treated and the severity of the disorder; activity of the specific agent employed; the specific composition employed, the age, body weight, general health, sex and diet of the patient; the time of administration, route of administration, and rate of excretion of the specific agent employed; the duration of the treatment; drugs used in combination or coincidental with the specific agent employed; and like factors well known in the medical arts. For example, it is well within the skill of the art to start doses of the agent at levels lower than those required to achieve the desired therapeutic effect and to gradually increase the dosage until the desired effect is achieved. However, the daily dosage of the products may be varied over a wide range from about 10 to about 10000 mg per adult per day, preferably 100 to about 5000, more preferably from about 200 to about 2000 mg per adult per day. Preferably, the compositions contain 10, 50, 100, 250, 500, 1000 and 2,000 mg of the active ingredient for the symptomatic adjustment of the dosage to the patient to be treated. A medicament typically contains from about 10 to about 10000 mg of the active ingredient, preferably 5 to about 5000, more preferably from about 10 to about 2000 mg of the active ingredient. An effective amount of the drug is ordinarily supplied at a dosage level from 0.01 mg/kg to about 100 mg/kg of body weight per day, preferably from about 0.05 mg/kg to 40 mg/kg of body weight per day, more preferably from about 0.1 mg/kg to 20 mg/kg of body weight per day, more preferably from about 0.2 mg/kg to 1 mg/kg of body weight per day.

For use in administration to a subject, the composition, pharmaceutical composition, medicament of the invention will be formulated for administration to the subject. The composition, pharmaceutical composition, medicament of the present invention may be administered orally, parenterally, topically, by inhalation spray, rectally, nasally, buccally, vaginally or via an implanted reservoir. The term administration used herein includes subcutaneous, intravenous, intramuscular, intraocular, intra-articular, intra-synovial, intrasternal, intrathecal, intrahepatic, intralesional and intracranial injection or infusion techniques.

In a preferred embodiment, the composition, pharmaceutical composition, medicament of the present invention is administered parenterally, subcutaneously, intravenously, or via an implanted reservoir.

In one embodiment, the composition, pharmaceutical composition, medicament of the invention is in a form adapted for topical administration.

Examples of forms adapted for topical administration include, but are not limited to, liquid, paste or solid compositions, and more particularly in form of aqueous solutions, drops, eye drops, ophthalmic solutions, dispersions, sprays, microcapsules, micro- or nanoparticles, polymeric patch, or controlled-release patch.

In one embodiment, the composition, pharmaceutical composition, or medicament of the invention comprises one or more pharmaceutical acceptable carrier for a formulation adapted for topical administration.

In one embodiment, the composition, pharmaceutical composition, or medicament of the invention is in a form adapted for injection, such as, for example, for intraocular, intramuscular, subcutaneous, intradermal, transdermal or intravenous injection or infusion.

Examples of forms adapted for injection include, but are not limited to, solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

Sterile injectable forms of the composition, pharmaceutical composition, medicament of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as TWEENs® (polysorbate), SPANs™ (sorbitan ester) and other emulsifying agents or bioavailability enhancers which are commonly used in the manufacture of pharmaceutically acceptable solid, liquid, or other dosage forms may also be used for the purposes of formulation.

In a particular embodiment, the composition, pharmaceutical composition, or medicament of the invention is in a form adapted for intraocular administration.

In one embodiment, the composition, pharmaceutical composition, or medicament of the invention is administered to the subject in need thereof at least once a day. For example, the composition, pharmaceutical composition, or medicament of the invention may be administered once a day, twice a day, or three times a day. In a preferred embodiment, the composition, pharmaceutical composition, or medicament of the invention is administered to the subject in need thereof once a day.

In another embodiment, the composition, pharmaceutical composition, or medicament of the invention is administered to the subject in need thereof at least once a week. For example, the composition, pharmaceutical composition, or medicament of the invention may be administered once a week, twice a week, three times a week, four times a week or up to seven times a week.

In another embodiment, the composition, pharmaceutical composition, or medicament of the invention is administered to the subject in need thereof once a month, two times a month, every two months, every two or three months, two times a year or once a year.

In one embodiment, the composition, pharmaceutical composition, or medicament of the invention is administered to the subject in need thereof before being exposed to a risk to develop thrombus. In one embodiment, the term "before" means at least a week before the exposure. In another embodiment, the term "before" means five days, four days, three days, two days or one day before the exposure. In another embodiment, the term "before" means 24 hours, 18 hours, 15 hours, 12 hours, 6 hours, 4 hours, 2 hours or 1 hour before the exposure. In another embodiment, the term "before" means less than one hour before the exposure, such as 45 minutes, 30 minutes, 15 minutes, 10 minutes, 5 minutes before the exposure or at the moment of the exposure. As an illustration, the composition, pharmaceutical composition, or medicament of the invention may be administered to the subject 24 hours, 12 hours, 6 hours or 1 hour before a prolonged travel, or at the beginning of the prolonged travel.

In another embodiment, the composition, pharmaceutical composition, or medicament of the invention is administered to the subject in need thereof after being exposed to a risk to develop thrombus. In one embodiment, the term "after" means 5 minutes, 10 minutes, 15 minutes, 30 minutes, or 45 minutes after the exposure. In another embodiment, the term "after" means 1 hour, 2, 4, 6, 12, 15, 18 or 14 hours after the exposure. In another embodiment, the term "after" means 1 day, 2, 3, 4 or five days after the exposure. In another embodiment, the term "after" means a week or more after the exposure. As an illustration, the composition, pharmaceutical composition, or medicament of the invention may be administered to the subject immediately after a prolonged travel, 1 hour, 2 hours, 6 hours, or 12 hours after the prolonged travel.

In one embodiment, the medical device coated with the fusion protein of the invention is formulated for administration to the subject. The medical device coated with the fusion protein of the present invention may be administered parenterally or topically, or may be implanted.

In one embodiment, the medical device coated with the fusion protein of the invention is implanted or is to be implanted in the cardiovascular system, comprising the heart and blood vessels. In one embodiment, the medical device coated with the fusion protein of the invention is implanted or is to be implanted in, to, or on the heart, such as, for example, on a heart ventricle. In another embodiment, the medical device coated with the fusion protein of the invention is implanted or is to be implanted in a blood vessel such as, for example, in a vein or in an artery.

In one embodiment, the composition, pharmaceutical composition, medicament or medical device of the invention is administered to the subject in need thereof in combination with at least another or supplemental therapeutic agent. In one embodiment, the at least one supplemental therapeutic agent is another therapeutic agent for treating or preventing thrombus. In another embodiment, the at least one supplemental therapeutic agent is a therapeutic agent for treating or preventing cardiovascular diseases. In another embodiment, the at least supplemental therapeutic agent is a therapeutic agent for treating or preventing neurodegenerative diseases. In another embodiment, the at least supplemental therapeutic agent is a therapeutic agent for treating or preventing cancer and/or metastasis.

In one embodiment, the composition, pharmaceutical composition, medicament or medical device of the invention is administered to the subject simultaneously, separately or sequentially with the at least one supplemental therapeutic agent.

Another object of the invention is a method of preventing thrombus formation and/or growth in a subject in need thereof, comprising administering to said subject a therapeutically effective amount of a fusion protein, polynucleotide, vector, pharmaceutical composition, medicament or medical device coated with a fusion protein of the invention.

Another object of the invention is a method of treating thrombus in a subject in need thereof, comprising administering to said subject a therapeutically effective amount of a fusion protein, polynucleotide, vector, pharmaceutical composition, medicament or medical device coated with a fusion protein of the invention.

A further object of the invention is a method of treating thrombus due to cardiovascular diseases, neurological diseases, cancer and/or metastasis in a subject in need thereof, comprising administering to said subject a therapeutically effective amount of a fusion protein, polynucleotide, vector, pharmaceutical composition, medicament or medical device coated with a fusion protein of the invention.

Another object of the invention is a method of treating or preventing cardiovascular diseases, neurological diseases, cancer and/or metastasis in a subject in need thereof, comprising administering to said subject a therapeutically effective amount of a fusion protein, polynucleotide, vector, pharmaceutical composition, medicament or medical device coated with a fusion protein of the invention.

The invention also relates to a method of reducing thrombus weight in a subject in need thereof, comprising administering to said subject a therapeutically effective amount of a fusion protein, polynucleotide, vector, pharmaceutical composition, medicament or medical device coated with a fusion protein of the invention.

The invention also relates to a method of inhibiting Factor XI and/or Factor XII in a subject in need thereof, comprising administering to said subject a therapeutically effective amount of a fusion protein, polynucleotide, vector, pharmaceutical composition, medicament or medical device coated with a fusion protein of the invention.

In one embodiment, the method comprises simultaneously inhibiting Factor XI and Factor XII in the subject in need thereof.

The invention further relates to a method of inhibiting extrinsic pathway of coagulation in a subject in need thereof, comprising administering to said subject a therapeutically effective amount of a fusion protein, polynucleotide, vector, pharmaceutical composition, medicament or medical device coated with a fusion protein of the invention. The invention also relates to a method of inhibiting platelet recruitment, neutrophil recruitment, neutrophil activation and neutrophil extracellular trap formation (NETosis) in a subject in need thereof, comprising administering to said subject a therapeutically effective amount of a fusion protein, polynucleotide, vector, pharmaceutical composition, medicament or medical device coated with a fusion protein of the invention.

The present invention also relates to a kit comprising a fusion protein, polynucleotide, vector, composition, pharmaceutical composition, medicament or medical device coated with a fusion protein according to the invention.

In one embodiment, the kit of the invention further comprises means to administer the fusion protein, polynucleotide, vector, composition, pharmaceutical composition, medicament or medical device to a subject in need thereof.

In one embodiment, the kit of the invention further comprises instructions for the administration of the fusion protein, polynucleotide, vector, composition, pharmaceutical composition, medicament or medical device to said subject. In one embodiment, the kit of the invention is a kit of parts wherein the first part is the fusion protein, polynucleotide, vector, composition, pharmaceutical composition, medicament or medical device and the second part comprises instructions for the administration of the fusion protein, polynucleotide, vector, composition, pharmaceutical composition, medicament or medical device to said subject.

In one embodiment, the kit of the invention is a kit of parts wherein the first part is the fusion protein, polynucleotide, vector, composition, pharmaceutical composition, medicament or medical device to said subject and the second part is at least one supplemental therapeutic agent.

In one embodiment, the kit of the invention is used for preventing thrombus formation and/or thrombus growth. In one embodiment, the kit of the invention is used for treating or preventing cardiovascular diseases, neurological diseases, cancer and/or metastasis.

BRIEF DESCRIPTION OF THE DRAWINGS

FIGS. 2A and 2B show effect of purified yeast recombinant IrCPI-fusion proteins on aPTT ratio in human plasma: effect of IrCPI-fusion proteins V2, V9, V13 and native IrCPI (A); effect of IrCPI-fusion proteins V12, V13, V15, V18, V19, V20, V27 and native IrCPI (B). Percentage of purity obtained and purification method used are indicated in brackets.

FIGS. 3A, 3B and 3C show pharmacokinetic and pharmacodynamic profiles of V13 in rabbits. V13 was administered at 260 nmol/kg (i.v.). (A) The pharmacokinetic profile was determined by measuring V13 concentrations by ELISA. (B) Pharmacodynamics were measured by aPTT on samples from the same animals. aPTT ratios correspond to the clotting time measured post-administration divided by the clotting time measured before administration. (C) The pharmacokinetic-pharmacodynamics relationship of V13 in rabbits. Results are expressed as mean±SEM. N=2 per time point.

FIGS. 7A, 7B, 7C and 7D show effect of V13 on thrombin generation. Human plasma was incubated with various concentrations of V13. Thrombin production was monitored after activation by Actin FS (A) or by tissue factor (TF, three concentrations: 1 pM, 5 pM and 20 pM, B-D), i.e. activators of the intrinsic and of the extrinsic coagulation pathway, respectively.

FIGS. 8A, 8B, 8C and 8D show effect of V13 on thrombin generation: Analysis of dose-response curves. Endogenous Thrombin Potential (ETP, A) i.e. area under the curve of thrombin generation; Maximal amplitude of thrombin generation (Peak, B); Delay up to start and up to maximal generation of thrombin (Lag time and time to Peak, C and D respectively).

FIGS. 9A and 9B show effect of V13 and synthetic IrCPI on thrombin generation in the presence of Actin FS or tissue factor (5 pM): peak (A) and lag time (B). Results are expressed as percentage compared to control (i.e. absence of V13 or IrCPI).

EXAMPLES

Figure 1:
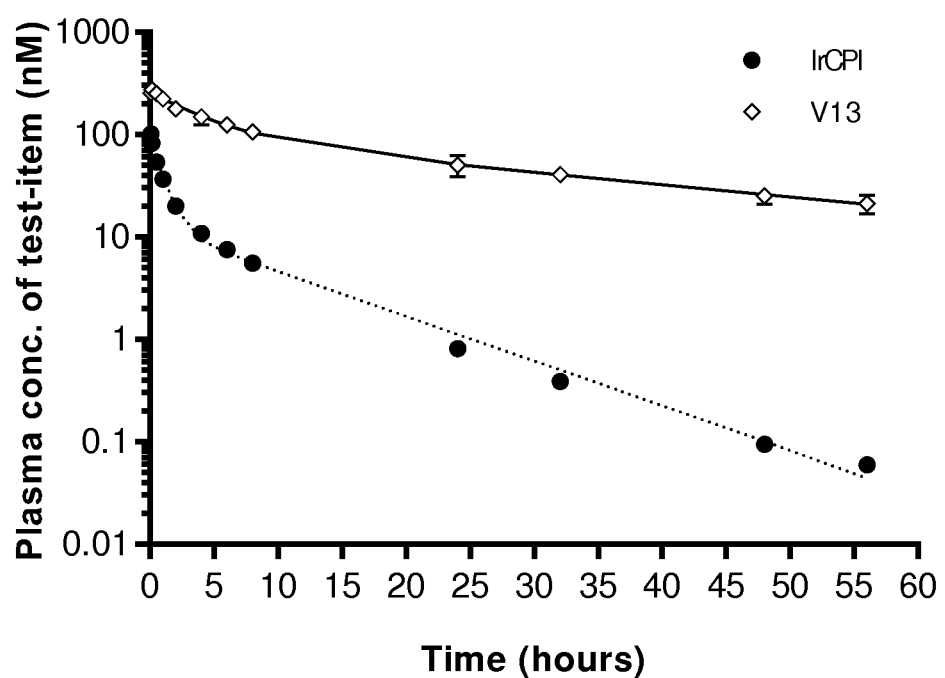
FIG. 1 shows pharmacokinetic profile of V13 and IrCPI in rabbits. Test-items were administered at 65 nmol/kg (iv). V13 and IrCPI concentrations were measured by ELISA except for time point T=0 h which corresponds to the theoretical administered dose. Results are expressed as mean±SEM. N=2 per time point.

The present invention is further illustrated by the following examples.

Example 1: Construction of the Fusion Proteins

Twenty-three constructions of IrCPI in fusion with human serum albumin (HSA) were investigated (Table 1).

TABLE 1

Constructions of fusion proteins comprising Ir-CPI and human serum albumin

| Fusion protein name | Constructions | MW (kDa) |
|---|---|---|
| V1 | IrCPI-HSA | 74.13 |
| V2 | HSA-IrCPI | 74.13 |
| V3 | IrCPI-GGGGS-HSA | 74.44 |
| V4 | HSA-GGGGS-IrCPI | 74.44 |
| V5 | IrCPI-IrCPI-HSA | 81.78 |
| V10 | HSA-IrCPI-IrCPI | 81.78 |
| V7 | IrCPI-PAPAP-HSA | 74.56 |
| V6 | HSA-PAPAP-IrCPI | 74.56 |
| V8 | IrCPI-AEAAAKEAAAKA-HSA | 75.21 |
| V9 | HSA-AEAAAKEAAAKA-IrCPI | 75.21 |
| V12 | IrCPI-(AP)$_7$-HSA | 75.3 |
| V18 | HSA-(AP)$_7$-IrCPI | 75.3 |
| V13 | IrCPI-(AP)$_{14}$-HSA | 76.5 |
| V19 | HSA-(AP)$_{14}$-IrCPI | 76.5 |
| V14 | IrCPI-(G$_4$S)$_3$A-HSA | 75.1 |
| V20 | HSA-(G$_4$S)$_3$A-IrCPI | 75.1 |
| V15 | IrCPI-GS(GGS)$_9$GS-HSA | 76.2 |
| V21 | HSA-GS(GGS)$_9$GS-IrCPI | 76.2 |
| V16 | IrCPI-A(EAAAK)$_4$A-HSA | 76.2 |
| V22 | HSA-A(EAAAK)$_4$A-IrCPI | 76.2 |
| V17 | IrCPI-A(EAAAK)$_4$ALEA-(EAAAK)$_4$A-HSA | 78.4 |
| V23 | HSA-A(EAAAK)$_4$ALEA-(EAAAK)$_4$A-IrCPI | 78.4 |
| V27 | IrCPI-(AP)$_7$-IrCPI-(AP)$_{14}$-HSA | 85.3 |

These differentiate by the presence or absence of peptide linker between the HSA and IrCPI molecule, the nature and the size of the linker used and the position of HSA relative to the IrCPI molecule (amino terminal or carboxy terminal of IrCPI). IrCPI-fusion proteins and IrCPI were produced in yeast *Pichia pastoris* with an expression vector under the control of AOX1 promoter. A point mutation in the oligonucleotide coding sequence of IrCPI was introduced in all constructions, leading to the replacement of Asparagine (Asp54) by Glutamine in order to prevent N-glycosylation. This modification in the amino acid sequence of IrCPI has been proven to have no consequence on the pharmacological activity of the molecule.

Example 2: Pharmacokinetic Profile of Fusion Proteins in Rabbits

Material and Methods

Male New-Zealand white rabbits (3-4 kg), received IrCPI-fusion protein (65 nmol/kg or 260 nmol/kg) or IrCPI (65 nmol/kg or 130 nmol/kg) under a volume of administration of 1 mL/kg (for 65 nmol/kg V2, V9, V13 and V20 variants) or 2 mL/kg (for 65 nmol/kg V13 and for 260 nmol/kg V12, V13, V18 and V19 variants) as a slow bolus, by intravenous route (marginal ear vein). The day before administration, a catheter was introduced into a carotid artery under isoflurane anesthesia for blood sampling. Blood samples were collected 5 min, 10 min, 30 min, 45 min, 1 h, 2 h, 4 h, 6 h, 8 h, 10 h, 24 h, 32 h, 48 h and 56 h after intravenous administration of the test items. Blood was collected from the catheter at each time-point in 0.109 M 3.2% sodium citrate tubes (citrate/blood, v/v 1/9) and plasma prepared after two consecutive centrifugations at 2500 g for 15 min.

Concentrations of IrCPI and of IrCPI-fusion proteins in the rabbit plasma were determined by sandwich ELISA using an anti-IrCPI monoclonal antibody (as capture antibody) and an anti-IrCPI polyclonal antibody (as detection antibody). As shown in Table 2, IrCPI and some IrCPI-fusion proteins were measured by an ELISA technique in which the anti-IrCPI polyclonal antibody was coupled to acetylcholinesterase to allow spectrophotometric monitoring using acetylthiocholine as the substrate and DTNB as the chromophore. The other IrCPI-fusion proteins were measured by an ELISA technique in which the anti-IrCPI polyclonal antibody is biotinylated and used in association with streptavidin-HRP to allow a spectrophotometric monitoring using 3, 3', 5, 5'-tetra-methylbenzidine (TMB SURE-BLUE™) as the substrate.

TABLE 2

Dose administered and ELISA method used for native IrCPI and IrCPI fusion protein tested

| IrCPI or IrCPI-fusion protein | Dose (nmol/kg) | ELISA method (detection antibody) |
|---|---|---|
| IrCPI | 65 | Polyclonal coupled to acetylcholinesterase |
|  | 130 | Polyclonal coupled to acetylcholinesterase |
| V2 | 65 | Polyclonal coupled to acetylcholinesterase |
| V9 | 65 | Polyclonal coupled to acetylcholinesterase |
| V12 | 260 | Polyclonal biotinylated + streptavidin-HRP |
| V13 | 65 | Polyclonal biotinylated + streptavidin-HRP |
|  | 260 | Polyclonal biotinylated + streptavidin-HRP |
| V15 | 65 | Polyclonal biotinylated + streptavidin-HRP |
| V18 | 260 | Polyclonal coupled to acetylcholinesterase |
| V19 | 260 | Polyclonal coupled to acetylcholinesterase |
| V20 | 65 | Polyclonal biotinylated + streptavidin-HRP |
| V27 | 260 | Polyclonal biotinylated + streptavidin-HRP |

Pharmacokinetic parameters were estimated using the PK SOLUTIONS© 2.0 software. A compartmental analysis (intravenous bolus and two-compartments) was performed.

The individual plasma concentration data were plotted against time after dosing for each dose.

The pharmacokinetic parameters were derived from these data.

Results

Results are presented in Table 3.

TABLE 3

Pharmacokinetic parameters of IrCPI-fusion proteins and native IrCPI in rabbits

| Parameters | IrCPI | V2 | V9 | V12 | V13 |
|---|---|---|---|---|---|
| Dose (nmol/kg, iv) | 65-130 | 65 | 65 | 260 | 65-260 |
| Dose (mg/kg, iv) | 0.5-1 | 5 | 5 | 20 | 5-20 |
| AUC (min * nmol/kg) | 12116-11430* | 618109 | 344942 | 398165* | 264953-318651* |
| CL (mL/min/kg) | 5.40-5.76 | 0.10 | 0.21 | 0.17 | 0.25-0.22 |
| T1/2 alpha (min) | 39-35 | 211 | 154 | 142 | 185-146 |
| T1/2 beta (min) | 415-474 | 2.792 | 1.072 | 1.115 | 1.579-987 |
| Vc (L/kg) | 0.677-0.878 | 0.087 | 0.122 | 0.099 | 0.236-0.125 |
| Vz (L/kg) | 3.225-3.913 | 0.425 | 0.289 | 0.268 | 0.566-0.292 |

| Parameters | V15 | V18 | V19 | V20 | V27 |
|---|---|---|---|---|---|
| Dose (nmol/kg, iv) | 65 | 260 | 260 | 65 | 260 |
| Dose (mg/kg, iv) | 5 | 20 | 20 | 5 | 20 |
| AUC (min * nmol/kg) | 475274 | 267681* | 177882* | 544296 | 29059* |
| CL (mL/min/kg) | 0.10 | 0.20 | 0.40 | 0.12 | 2.20 |
| T1/2 alpha (min) | 78 | 218 | 190 | 141 | 56 |
| T1/2 beta (min) | 1.047 | 1.020 | 1.012 | 1.082 | 1.010 |
| Vc (L/kg) | 0.106 | 0.191 | 0.253 | 0.092 | 0.268 |
| Vz (L/kg) | 0.209 | 0.366 | 0.552 | 0.190 | 3.233 |

*AUC: Area Under the Curve normalized for a same administered dose of 65 nmol/kg Circulating exposure to the compound (AUC, area under the curve normalized for a same administered dose of 65 nmol/kg) was between 2.5-fold (V27) and 54-fold (V2) higher with fusion proteins than that obtained with native IrCPI. Moreover, fusion proteins have a lower clearance (CL) than native IrCPI and, except for V27, a lower volume of distribution (Vz) which translates also to a longer terminal half-life ($t_{1/2}\beta$), up to 3.8-fold higher than native IrCPI. As $t_{1/2}\beta$ relates to the time for a molecule to be degraded or eliminated from the blood circulation, a longer $t_{1/2}\beta$ means a longer duration of action.

The volume of distribution of the IrCPI-fusion proteins is lower than that of native IrCPI meaning the IrCPI-fusion proteins remain advantageously in the vascular compartment where they may exert their activity.

The study conducted on different IrCPI-fusion proteins indicates that the fusion of IrCPI with human serum albumin improves consistently and whatever the variant, the PK profile of the native IrCPI molecule.

As example, FIG. 1 illustrates the larger and longer exposure obtained with V13 as competed to IrCPI administered at same molar dose.

Example 3: Anticoagulant Activity

Material and Methods

The anticoagulant activities of the IrCPI-fusion proteins were determined by a coagulation test on a human plasma pool using an activator of the contact phase to induce coagulation. IrCPI-fusion proteins were diluted in a buffer of 20 mM Hepes, 140 mM NaCl (pH 7.35). Native IrCPI was used as a comparator in this assay.

Activated Partial Thromboplastin Time (aPTT)

Plasma (platelet poor plasma, PPP) was mixed with different concentrations of an IrCPI fusion protein or synthetic IrCPI to reach final concentrations ranging from 0 to 2 pM. Next, 50 µL of each IrCPI fusion protein-containing plasma or IrCPI-treated plasma, was incubated for 240 seconds with 50 µl of Actin FS (ellagic acid+phospholipids). The clotting reaction was started by adding 50 µl of 25 mM $CaCl_2$) and the clotting time (aPTT) was monitored. aPTT ratios were calculated by dividing the clotting time measured in the presence of test item (i.e. IrCPI-fusion protein or Ir-CPI) by the clotting time obtained without test substance.

Results

FIG. 2 shows that IrCPI fusion proteins prolonged the aPTT in a concentration-dependent manner with variable degree of efficacy. aPTT results were obtained from 2 independent laboratories and divided in 2 separates graphs. On FIG. 2A, by decreasing order, V13 was the most active variant, followed by V9 and V2. V13 increased the time to coagulate (aPTT) by 67% at 0.5 µM, 84% at 1 µM and 106% at 2 µM, respectively. On FIG. 2B, V27 was the most active variant, followed by V13, next V12, V19, V18, V15 and then V20. V27 increased the time to coagulate (aPTT) by 58% at 0.5 µM, 98% at 1 µM and 152% at 2 µM, respectively.

Example 4: Pharmacokinetic and Pharmacodynamics Relationship with V13

Material and Methods Male New Zealand white rabbits (2-3.5 kg), received V13 (20 mg/kg corresponding to 260 nmol/kg) under a volume of administration of 2 mL/kg as a slow bolus, by intravenous route (marginal ear vein).

Blood was collected from the catheter at each time-point in 0.109 M 3.2% sodium citrate tubes (citrate/blood, v/v 1/9) and plasma prepared after two consecutive centrifugations at 2500 g for 15 min.

Concentrations of V13 in rabbit plasma was determined by sandwich ELISA using an anti-IrCPI monoclonal antibody (as capture antibody) and an anti-IrCPI polyclonal antibody (as detection antibody) coupled to acetylcholinesterase to allow spectrophotometric monitoring using acetylthiocholine as the substrate and DTNB as the chromophore.

Pharmacodynamics were measured by aPTT, according to the same protocol as Example 3, at the time points 45 min, 4 h, 10 h and 24 h post-administration.

Results

Similar profiles were observed for V13 plasma concentrations and aPTT ratio in rabbit plasma ex vivo, i.e. both showed a progressive decrease over time after bolus administration (FIGS. 3A, B and C). The time to coagulate was increased by +408%, +220% and +45% at respectively 45 minutes, 4 h and 10 h post-administration and corresponded to mean plasmatic concentrations of 1.87 µM, 0.97 µM and 0.55 µM. The results confirm that amount of the active principle (monitored by aPTT ratio) was consistent with the circulating concentration of V13 (monitored by ELISA method).

Example 5: Evaluation of the Inhibitory Effect of V13 on Factors XI and XII Activities The effect of V13 on the inhibition of factors XI and XII activities was assessed in an aPTT-based coagulation assay using FXII or FXI deficient plasma complemented with diluted normal human plasma. Synthetic IrCPI was used as a comparator in this assay.

Material and Methods

Nine volumes of a human plasma pool were mixed with one volume of V13 or IrCPI and incubated during 30 minutes at 37° C. V13 or ICPI was added as a 10-fold solution and tested using a range of concentrations. Treatments were compared to controls (i.e. absence of V13 or IrCPI) consisting of nine volumes of the human plasma pool to which one volume of Tris (0.05 M), NaCl (0.15 M), BSA (1%) buffer (pH 7.50) was added.

After a 30 min incubation, samples were diluted 1:10 with imidazole buffer. Then, 50 µL of each diluted sample was mixed with 50 µL of Factor XI deficient human plasma or with 50 µL Factor XII deficient human plasma (1 min at 37° C.), followed by an addition of 50 µL of the aPTT reagent CEPHEN™ (cephalin). The contact phase was activated by CEPHEN™ during an incubation of 10 min at 37° C. Clotting was initiated by the addition of 50 µL of 0.025 M $CaCl_2$) (preincubated at 37° C.) and clotting times were recorded.

FXI and FXII calibration curves were made for the calculation of plasma FXI and FXII activities after V13 treatment. Human plasma calibrator (duly titrated with FXI and FXII) was used at successive two-step dilutions with imidazole buffer (1:10 to 1:160 dilution). Each dilution was incubated with FXI or FXII deficient plasma, CEPHEN™ and with 0.025M $CaCl_2$) as described above (ratio 1:1:1:1).

FXI and FXII calibration curves were obtained by plotting clotting times in function of the FXI/FXII activity of the different dilutions of the calibrator using a log-log plot. The 10-fold dilution of the calibrator is considered having 100% activity. There is an inverse linear relationship between the FXI or FXII activity and the corresponding clotting time, when plotted on a log-log-graph. The equations of the calibration curves were used to calculate the FXI and FXII activities in the human plasma pool treated with V13. The residual activity after V13 treatment was calculated as a percentage compared to control (untreated normal human plasma). Results are expressed as the percentage of inhibition of FXI and FXII activities after V13 treatment as compared to control, i.e. absence of V13, and calculated as follows:

$$\% \text{ inhibition } FXI = (1 - FXI_\%^{IrcPI} / FXI_\%^{CTLL}) * 100$$

$$\% \text{ inhibition } FXII = (1 - FXII_\%^{IrCPI} / FXII_\%^{CTL}) * 100.$$

Results

Figure 4:
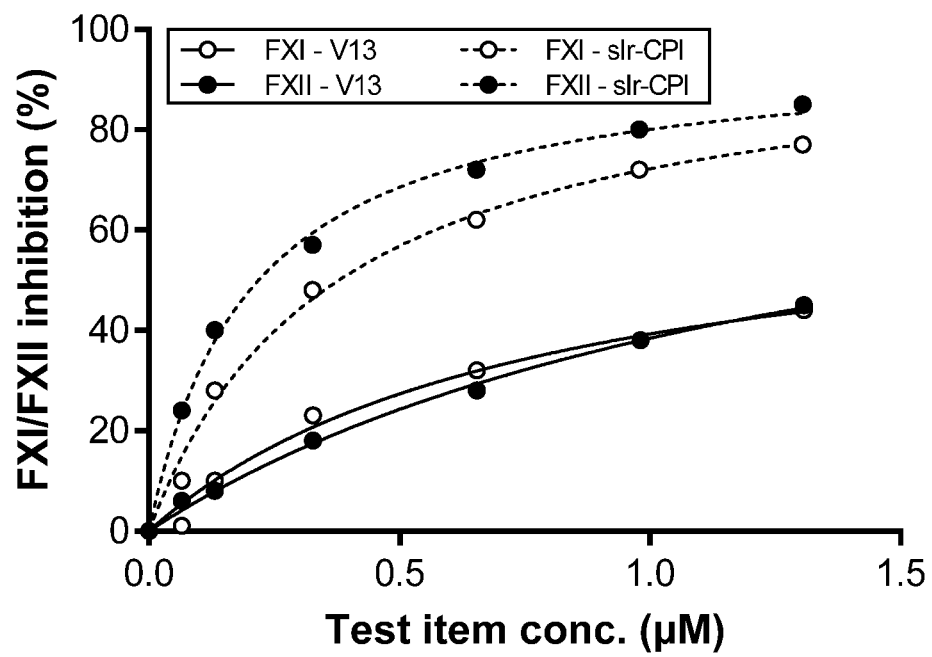
FIG. 4 shows inhibitory effect of V13 and IrCPI on FXI and FXII coagulation activities in human plasma. FXI and FXII curves represent the fitting to a hyperbolic equation. Black and white circles represent individual data.

As shown in FIG. 4, patterns of inhibition of FXI and FXII followed similar hyperbolic curves as function of the concentration of V13. At the highest concentration (1.3 µM), V13 inhibited the FXI and FXII activity by 44% and 45% respectively. Synthetic Ir-CPI inhibited the FXI/FXII activity by 77/85% at the same concentration.

The results indicate that the fusion of Ir-CPI molecule to human serum albumin allows (e.g. V13) a significant preservation of the activity of Ir-CPI keeping a selectivity and specificity of action on the contact phase of coagulation whilst improving the pharmacokinetic profile of the initial molecule.

The PK profiles of the IrCPI-HSA variants should allow administration of lower molar doses and within larger intervals to obtain a pharmacological effect on steady state.

Example 6: Antithrombotic Effect of V13 in the Rat AV-Shunt Model

The antithrombotic efficacy of V13 was evaluated in an extracorporeal arterio-venous (AV) shunt (silk thread) rat model.

Material and Methods

Rats were fasted overnight and were then anesthetized (ketamine/xylazine at 100/16 mg/kg i.m.). An arterio-venous shunt was prepared as follows: two 13 cm-long polyethylene tubes (0.85 mm i.d. and 1.27 mm o.d.) linked to a central part (6 cm-long; 1.14 mm i.d.) containing a 5-cm silk thread (USP 0, EP 3.5) and filled with physiological saline was placed between the left jugular vein and the right carotid artery (inserting the venous side first). After 20 minutes of extracorporeal blood circulation through the shunt, the blood flow was stopped at the arterial side. The central part of the shunt was then removed and the silk thread supporting the thrombus was extracted. The wet weight of the thrombus was immediately determined by subtracting the weight of the wet thread.

The test substances were administered i.v. 5 minutes before the test (shunt), and compared with a respective vehicle control group. Sodium heparin (UFH), administered i.v. 5 minutes before the test (shunt), was used as positive control.

Concentrations used during the experiment were the following: V13: 1.21 or 2.08 µmol/kg and UFH: 100 or 300 IU/kg.

Concentrations of V13 in the rat plasma were determined by sandwich ELISA using an anti-IrCPI monoclonal antibody (as capture antibody) and an anti-IrCPI polyclonal antibody (as detection antibody) biotinylated and used in association with streptavidin-HRP to allow a spectrophotometric monitoring using 3, 3', 5, 5'-tetra-methylbenzidine (TMB SUREBLUE™) as the substrate.

The effect on the activated partial thromboplastin time (aPTT) was measured using Actin FS (ellagic acid and phospholipids) as reagent. The analyzed plasmas were obtained immediately after shunt termination. Results are expressed as the ratio between the individual aPTT value in the presence of V13 divided by the mean aPTT value of the vehicle condition.

Results

Figure 5:
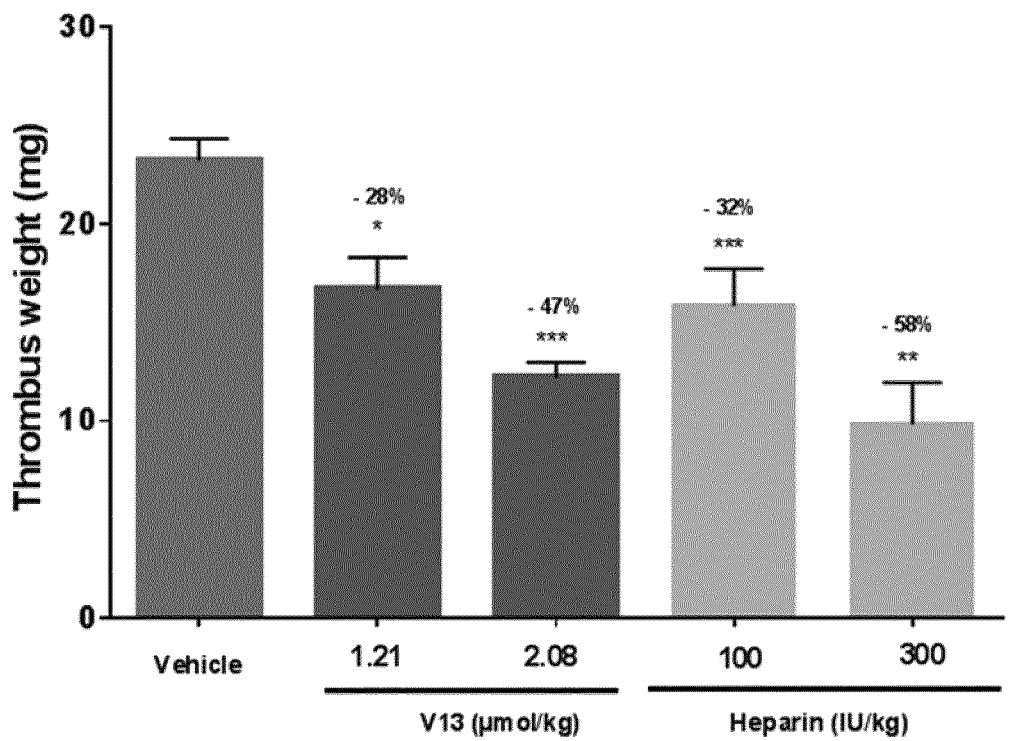
FIG. 5 shows effects of Ir-CPI and V13 on thrombus weight (mg) in the rat AV-shunt. UFH was used as positive control of the test. One-way ANOVA followed by a Dunnett's multiple comparison test was used for statistical analysis (*$p<0.05$; $p<0.01$; *$p<0.001$). All data were compared to the vehicle condition.

As shown in FIG. 5, V13 (1.21 or 2.08 µmol/kg), administered i.v., induced a significant reduction of thrombus weight after 20 min of the AV-shunt procedure.

At 2.08 µmol/kg, V13 (mean thrombus weight: 12.17 mg) significantly reduced by 1.9-fold the thrombus weight when compared to the vehicle (control) condition (mean thrombus weight: 23.16 mg).

The positive control, UFH had a marked antithrombotic activity in this model. At 300 IU/kg, UFH (mean thrombus weight: 9.83 mg) significantly reduced by 2.4-fold the thrombus weight when compared to the vehicle (control) condition (mean thrombus weight: 23.16 mg).

Figure 6:
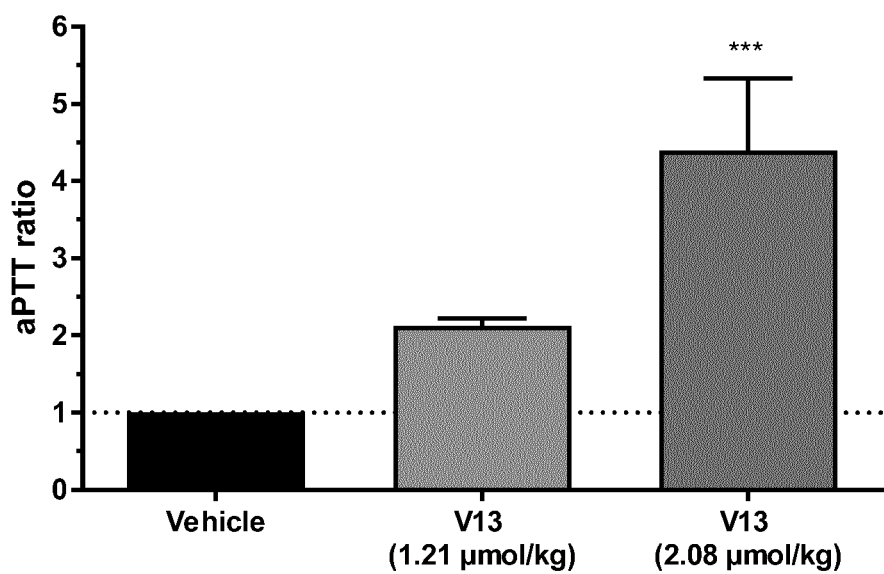
FIG. 6 shows effect of V13 administration on the aPTT ratio after 20 min of rat AV-shunt. V13 was administered as a bolus, 5 min before AV-shunt opening. Vehicle corresponds to a bolus of PBS. Results are expressed as mean±SEM (n≥5 per group). Statistical significance versus corresponding vehicle group as determined by a one-way ANOVA and a Dunnett's multiple comparison post-hoc test (***p<0.001).

Following a single bolus administration of 93 mg/kg (1.21 µmol/kg) of V13, 5 min before the AV-shunt opening, the mean aPTT ratio (±SEM) was 2.1±0.1 (n=6) (FIG. 6).

Following a single bolus administration of 160 mg/kg (2.08 µmol/kg) of V13, 5 min before the AV-shunt opening, the mean aPTT ratio (±SEM) was 4.4±0.9 (n=6). This aPTT ratio was significantly higher than the aPTT ratio of the vehicle group (p<0.001) (FIG. 6).

Example 7: Effect of V13 on Thrombin Generation

Material and Methods

The calibrated automated thrombin activity measurement of V13 was determined on human plasma pool. Synthetic IrCPI was used as a comparator in this assay. Plasma (platelet-poor plasma [PPP]) (450 µL) was mixed with 50 µL of solutions containing different concentrations of V13 or IrCPI (10-times concentrated). Eighty (80) µL of spiked plasma and 20 µL reagent (PPP LOW reagent (PPL1510/02, Thrombinoscope BV); PPP reagent (PPP1509/01, Thrombinoscope BV); PPP HIGH (PPPH1501/01, Thrombinoscope BV) or diluted Actin FS (batch 53851, Siemens, [1/20])) were mixed in a 96-well microtiter plate (IMMULON™ 2HB; Thermo Fisher Scientific) and incubated for 5 min at 37° C. The coagulation process was triggered by the addition of 20 µL of fluorogenic substrate in a calcium chloride buffer pre-warmed at 37° C. A calibration curve was also performed simultaneously using 80 µL of normal pooled plasma, 10 µL of PBS, 20 µL of thrombin calibrator and 20 µL of substrate/calcium chloride-buffered solution at 37° C. The substrate hydrolysis was monitored on a microplate fluorometer FLUOROSCAN ASCENT® FL (Thermo Labsystems) with a 390/460 nm filter set. Fluorescence was measured every 20 sec for 60 min. Eleven concentrations of V13 and IrCPI were tested which ranged from 0 to 2 µM. A dedicated software program (Thrombinoscope 5.0, Synapse BV) calculated thrombin concentration generated in plasma depending on V13 or IrCPI concentrations added and displayed thrombin concentrations as function of time. Moreover, it enabled the calculation of the following TGT (Thrombin Generation Time) parameters:
- endogenous thrombin potential (ETP; [nM]): the sum amount of active thrombin which was present in the system over entire time of experiment (area under the thrombin generation curve),
- maximal thrombin concentration in the sample (Peak thrombin [nM]]),
- time to reach the maximal concentration of thrombin (ttPeak [min]),
- lag-time before beginning of accelerated thrombin production (LagTime [min]).

Results

FIGS. 7 (thrombin generation time curves) and 8 (curves analysis) show the effects of V13 on thrombin generation induced by Actin FS or by tissue factor (TF, tested at 3 concentrations 1, 5 and 20 µM). When using Actin FS as inducer of the thrombin generation (FIG. 7A), V13 showed a concentration-dependent decrease of thrombin generation (Peak: maximum amplitude and ETP: AUC i.e. overall production) and a concentration-dependent delay in the thrombin generation (lag time and time to peak). At the highest concentration (2 µM), V13 inhibited the endogenous thrombin potential (ETP) and peak by 46% and 79% respectively. At the same concentration, V13 increased the time to peak and the lag time by 3-fold and 3.2-fold respectively. When using tissue factor as inducer of the thrombin generation (FIG. 7B-D), V13 inhibited ETP maximally by 20% (2 µM of V13 with TF concentration of 1 µM). V13 (2 µM) decreased the peak thrombin generation by 11 to 41% and increased the lag time or time to peak by 1.3 to 1.5-fold depending on the concentration of tissue factor (relative effects more pronounced at lower than higher concentration of TF: 1>5>20 µM).

The results show that V13 inhibits more specifically the production of thrombin when induced by Actin FS than by TF. They are consistent with V13 inhibiting more specifically the activation of the contact phase (intrinsic coagulation pathway) than the activation of tissue factor pathway (extrinsic coagulation pathway), which was also observed for IrCPI (FIG. 9).

Example 8: Effect of V13 on Prothrombin Time

Material and Methods
Preparation of Human Platelet-Poor Plasma

Fifty-six individuals were included in the study. The exclusion criteria were thrombotic and/or hemorrhagic events, antiplatelet and/or anticoagulant medication, hormonal therapy, pregnancy and uptake of drugs potentially affecting the platelet and/or coagulation factor functions during the two weeks prior to the blood drawn. The study protocol is in accordance with the Declaration of Helsinki. Blood was taken by venipuncture in the antecubital vein and collected into 0.109M sodium citrate (9:1 v/v) tubes (VEOSAFE®, Terumo, Belgium) using a 21-gauge needle (Terumo). The PPP was obtained from the supernatant fraction of blood tubes after a double centrifugation for 15 minutes at 1.500 g at room temperature. Immediately after centrifugation, PPP from the 40 donors were brought together to obtain the NPP which was frozen at −80° C. without any delay. Frozen NPP samples are thawed and heat to 37° C. for 5 minutes just before experiment. All tests were performed within 4 hours after thawing.

Preparation of human spiked samples Human plasma (PPP) (450 µl) obtained was mixed with 50 µl of solutions containing different concentrations of V13 (10-times concentrated) or synthetic IrCPI to reach final concentrations ranging from 0 to 2 µM.

Measurement of anticoagulant activity of IrCPI in spiked samples The prothrombin time consists of the use of calcium thromboplastin, prepared from human recombinant tissue factor and from phospholipids, to measure the clotting time of the plasma sample (as prepared above) and to compare it with that of a normal standard (pre-calibrated reagent). The test is performed according to the recommendations of the manufacturer (STA-NOPLASTIN R® from Diagnostica Stago-application for a STA®-R Evolution analyzer).

Briefly, fifty (50) µL of plasma in presence of V13 or IrCPI was incubated for 240 seconds at 37° C. The clotting reaction was then started by adding 100 µL of STA®-NOPLASTIN R® (STAGO). The measurement was performed on a STA®-R Evolution analyzer (Diagnostica Stago) using viscometric method for clot detection.

Results

Results are presented in Table 4.

TABLE 4

Effect of V13 and native IrCPI on prothrombin time

| Test item concentration | V13 | | IrCPI | |
|---|---|---|---|---|
| (µM) | PT (sec) | % | PT (sec) | % |
| 2 | 14.6 | 105 | 14.3 | 103 |
| 1 | 14.7 | 105 | 14.4 | 103 |
| 0.5 | 14.3 | 103 | 14.0 | 101 |
| 0.25 | 14.1 | 101 | 14.1 | 101 |
| 0.125 | 14.3 | 102 | 14.1 | 101 |
| 0 | 14.0 | 100 | 13.9 | 100 |

The prothrombin time (PT) is an assay evaluating the activity of extrinsic coagulation factors (Factor II (FII), FV, FVII and FX).

The results of Table 4 show that no concentration-dependent effect was found of V13 or IrCPI on the prothrombin time.

The invention claimed is:

1. A fusion protein comprising (i) at least one *Ixodes ricinus* salivary gland (IrCPI) polypeptide, having an amino acid sequence at least 95% identical to SEQ ID NO: 1, (ii) at least one human serum albumin polypeptide and (iii) at least one peptide linker, wherein the fusion protein has an increased circulatory half-life compared to an unfused IrCPI polypeptide, wherein said at least one peptide linker is a Pro-rich linker selected from a group consisting of $(AP)_n$ and $P(AP)_n$ linker, and wherein "n" is a number from 5 to 15.

2. The fusion protein of claim 1, wherein said at least one peptide linker is a Pro-rich linker having the amino acid sequence of $(AP)_{14}$ (SEQ ID NO: 26).

3. The fusion protein of claim 1, wherein the fusion protein is selected from a group consisting of: SEQ ID NO: 17, SEQ ID NO: 31, SEQ ID NO: 37, SEQ ID NO: 38, SEQ ID NO: 39, and SEQ ID NO: 46.

4. A pharmaceutical composition or a medicament comprising a fusion protein comprising (i) at least one *Ixodes ricinus* salivary gland (IrCPI) polypeptide, having an amino sequence at least 95% identical to SEQ ID NO: 1, (ii) at least one human serum albumin polypeptide and (iii) at least one peptide linker, wherein the fusion protein has an increased circulatory half-life compared to an unfused IrCPI polypeptide, and at least one pharmaceutically acceptable excipient, wherein said at least one peptide linker is a Pro-rich linker selected from a group consisting of $(AP)_n$ and $P(AP)_n$ linker, and wherein "n" is a number from 5 to 15.

5. A medical device coated with the fusion protein of claim 1.

6. A method for treating thrombus in a subject in need thereof, said method comprising administering to said subject an effective therapeutic dose of the pharmaceutical composition or medicament of claim 4.

7. A method for inhibiting platelet recruitment, neutrophil recruitment, neutrophil activation and/or neutrophil extracellular trap formation (NETosis) in a subject in need thereof, said method comprising administering to said subject an effective therapeutic dose of the pharmaceutical composition or medicament of claim 4.

* * * * *